(12) United States Patent
Breves et al.

(10) Patent No.: US 7,803,604 B2
(45) Date of Patent: Sep. 28, 2010

(54) **AMYLOLYTIC ENZYME EXTRACTED FROM *BACILLUS* SP. A 7-7 (DSM 12368) AND WASHING AND CLEANING AGENTS CONTAINING THIS NOVEL AMYLOLYTIC ENZYME**

(75) Inventors: Roland Breves, Mettmann (DE); Karl-Heinz Maurer, Erkrath (DE); Beatrix Kottwitz, Erkrath (DE); Laura Polanyi-Bald, Cologne (DE); Angela Hellebrandt, Cologne (DE); Irmgard Schmidt, Solingen (DE); Regina Stehr, Duesseldorf (DE); Angrit Weber, Bergisch-Gladbach (DE)

(73) Assignee: Henkel AG & Co. KGaA (DE)

( * ) Notice: Subject to any disclaimer, the term of this patent is extended or adjusted under 35 U.S.C. 154(b) by 329 days.

(21) Appl. No.: 11/975,898

(22) Filed: Oct. 22, 2007

(65) Prior Publication Data

US 2009/0120555 A1 May 14, 2009

Related U.S. Application Data

(62) Division of application No. 11/590,976, filed on Nov. 1, 2006, now Pat. No. 7,303,905, which is a division of application No. 10/343,212, filed as application No. PCT/EP01/08359 on Jul. 19, 2001, now Pat. No. 7,153,818.

(30) Foreign Application Priority Data

Jul. 28, 2000  (DE) ................................. 100 36 752
Jul. 28, 2000  (DE) ................................. 100 36 753

(51) Int. Cl.
 *C12N 1/20* (2006.01)
(52) U.S. Cl. .............................. 435/252.31; 435/252.3; 435/320.1; 435/204; 536/23.2
(58) Field of Classification Search ................. 435/204, 435/252.3, 320.1, 252.31; 536/23.2
See application file for complete search history.

(56) References Cited

U.S. PATENT DOCUMENTS

| 1,227,374 A | 5/1917 | Bodin et al. |
|---|---|---|
| 3,623,957 A | 11/1971 | Feldman |
| 3,985,923 A | 10/1976 | Basadur |
| 4,116,885 A | 9/1978 | Derstadt et al. |
| 4,264,738 A | 4/1981 | Stepanov et al. |
| 4,501,681 A | 2/1985 | Groult et al. |
| 4,548,727 A | 10/1985 | Shaer |
| 4,568,476 A | 2/1986 | Kielman et al. |
| 4,597,886 A | 7/1986 | Goedhart et al. |
| 4,620,936 A | 11/1986 | Kielman et al. |
| 4,652,394 A | 3/1987 | Inamorato et al. |
| 4,661,287 A | 4/1987 | Crossin |
| 4,664,839 A | 5/1987 | Rieck |
| 4,724,208 A | 2/1988 | Brewer et al. |
| 5,171,673 A | 12/1992 | Sloma et al. |
| 5,208,158 A | 5/1993 | Bech et al. |
| 5,246,612 A | 9/1993 | Van Dijk et al. |
| 5,318,714 A | 6/1994 | Markussen et al. |
| 5,318,733 A | 6/1994 | Carduck et al. |
| 5,389,307 A | 2/1995 | Lindegaard et al. |
| 5,458,810 A | 10/1995 | Fredj et al. |
| 5,470,509 A | 11/1995 | Pancheri |
| 5,472,628 A | 12/1995 | Panandiker |
| 5,501,820 A | 3/1996 | Van den Bergh et al. |
| 5,560,748 A | 10/1996 | Surutzidis et al. |
| 5,591,703 A | 1/1997 | Sadlowski |
| 5,614,161 A | 3/1997 | Wilkens et al. |
| 5,616,550 A | 4/1997 | Kruse et al. |
| 5,705,169 A | 1/1998 | Stein et al. |
| 5,719,112 A | 2/1998 | Gordon et al. |
| 5,726,141 A | 3/1998 | Ofosu-Asante |
| 5,730,960 A | 3/1998 | Stein et al. |
| 5,731,280 A | 3/1998 | Nielsen et al. |
| 5,736,499 A | 4/1998 | Mitchinson et al. |
| 5,739,091 A | 4/1998 | Kiesser et al. |
| 5,753,460 A | 5/1998 | Bisgard-Frantzen et al. |
| 5,763,385 A | 6/1998 | Bott et al. |
| 5,783,540 A | 7/1998 | Secemski et al. |

(Continued)

FOREIGN PATENT DOCUMENTS

CA       958 618       12/1974

(Continued)

OTHER PUBLICATIONS

Boyer et al., Staerke, 3(5):166-171 (1979).

(Continued)

*Primary Examiner*—Tekchand Saidha
(74) *Attorney, Agent, or Firm*—Connolly Bove Lodge & Hutz LLP

(57) ABSTRACT

The invention relates to a novel amylolytic enzyme extracted from the microorganism *Bacillus* sp. A 7-7 (DSM 12368), to sufficiently similar proteins having an amylolytic function, to methods for the production thereof and to diverse fields of application for these proteins. In addition, the aforesaid can be further developed beyond the implemented fields of application for other technical purposes. The invention particularly relates to washing and cleaning agents containing amylolytic proteins of the aforementioned type, to methods for cleaning textiles or hard surfaces that involve the use of the amylolytic proteins or analogous agents, and to their use for cleaning textiles or hard surfaces.

1 Claim, 2 Drawing Sheets

U.S. PATENT DOCUMENTS

| | | | |
|---|---|---|---|
| 5,783,545 A | 7/1998 | Paatz et al. | |
| 5,783,546 A | 7/1998 | Bettiol et al. | |
| 5,789,364 A | 8/1998 | Sells et al. | |
| 5,801,043 A | 9/1998 | Bisgard-Frantzen et al. | |
| 5,824,531 A | 10/1998 | Outtrup et al. | |
| 5,830,837 A | 11/1998 | Bisgard-Frantzen et al. | |
| 5,851,235 A | 12/1998 | Baillely et al. | |
| 5,858,946 A | 1/1999 | Foley et al. | |
| 5,928,381 A | 7/1999 | Toft et al. | |
| 5,929,018 A | 7/1999 | Baillely et al. | |
| 5,939,373 A | 8/1999 | Haeggberg et al. | |
| 5,958,739 A | 9/1999 | Mitchinson et al. | |
| 5,962,613 A | 10/1999 | Schade et al. | |
| 5,965,510 A | 10/1999 | Schneider et al. | |
| 5,968,881 A | 10/1999 | Haeggberg et al. | |
| 5,972,873 A | 10/1999 | Nielsen et al. | |
| 5,998,342 A | 12/1999 | Scoville, Jr. et al. | |
| 6,008,026 A | 12/1999 | Day | |
| 6,008,178 A | 12/1999 | Baillely et al. | |
| 6,015,783 A | 1/2000 | Von der Osten et al. | |
| 6,022,724 A | 2/2000 | Svendsen et al. | |
| 6,034,044 A | 3/2000 | Scheper et al. | |
| 6,046,149 A | 4/2000 | Sorrie et al. | |
| 6,057,277 A | 5/2000 | Crudden et al. | |
| 6,075,001 A | 6/2000 | Wilde | |
| 6,077,316 A | 6/2000 | Lund et al. | |
| 6,080,568 A | 6/2000 | Day et al. | |
| 6,083,898 A | 7/2000 | Meixner et al. | |
| 6,093,562 A | 7/2000 | Bisgärd-Frantzen et al. | |
| 6,136,778 A | 10/2000 | Kamiya | |
| 6,140,292 A | 10/2000 | Randall et al. | |
| 6,140,293 A | 10/2000 | Lappas | |
| 6,143,708 A | 11/2000 | Svendsen et al. | |
| 6,159,918 A | 12/2000 | Bae-Lee et al. | |
| 6,165,770 A | 12/2000 | Sjoholm et al. | |
| 6,172,020 B1 | 1/2001 | Binstock et al. | |
| 6,187,055 B1 | 2/2001 | Kottwitz et al. | |
| 6,187,576 B1 | 2/2001 | Svendsen et al. | |
| 6,193,960 B1 | 2/2001 | Metzger et al. | |
| 6,197,565 B1 | 3/2001 | Svendsen et al. | |
| 6,204,232 B1 | 3/2001 | Borchert et al. | |
| 6,211,134 B1 | 4/2001 | Caldwell et al. | |
| 6,218,164 B1 | 4/2001 | Jones et al. | |
| 6,221,825 B1 | 4/2001 | Williams, Jr. et al. | |
| 6,228,825 B1 | 5/2001 | Gorlin et al. | |
| 6,277,802 B1 | 8/2001 | Chiou et al. | |
| 6,297,038 B1 | 10/2001 | Bisgärd-Frantzen et al. | |
| 6,362,150 B1 | 3/2002 | Lunati | |
| 6,379,394 B1 | 4/2002 | Chilou et al. | |
| 6,417,152 B1 | 7/2002 | Kottwitz et al. | |
| 6,528,298 B1 * | 3/2003 | Svendsen et al. | 435/202 |
| 6,673,589 B2 | 1/2004 | Borchert et al. | |
| 6,867,031 B2 | 3/2005 | Bisgärd-Frantzen et al. | |
| 7,303,905 B2 * | 12/2007 | Breves et al. | 435/204 |
| 2002/0032142 A1 | 3/2002 | Smets et al. | |
| 2002/0037824 A1 | 3/2002 | Smets et al. | |
| 2002/0068352 A1 | 6/2002 | Svendsen et al. | |

FOREIGN PATENT DOCUMENTS

| | | |
|---|---|---|
| CA | 2 306 376 | 10/2000 |
| CN | 1190121 | 8/1998 |
| DE | 19 40 488 | 2/1971 |
| DE | 1 617 141 | 4/1972 |
| DE | 21 21 397 | 11/1972 |
| DE | 2 253 063 | 5/1973 |
| DE | 2 200 911 | 10/1973 |
| DE | 28 57 292 A1 | 2/1980 |
| DE | 33 24 258 A1 | 1/1984 |
| DE | 40 131 42 A1 | 10/1991 |
| DE | 4110764 | 10/1992 |
| DE | 4114956 | 11/1992 |
| DE | 4418487 | 11/1995 |
| DE | 44 43 177 A1 | 6/1996 |
| DE | 196 01 063 A1 | 9/1996 |
| DE | 196 16 693 A1 | 11/1997 |
| DE | 196 16 767 A1 | 11/1997 |
| DE | 196 16 769 A1 | 11/1997 |
| DE | 196 16 770 A1 | 11/1997 |
| DE | 196 50 537 A1 | 6/1998 |
| DE | 197 09 284 A1 | 9/1998 |
| DE | 197 12 033 A1 | 9/1998 |
| DE | 199 18 267 A1 | 10/2000 |
| DE | 199 56 382 A1 | 5/2001 |
| EP | 0 006 638 B1 | 4/1984 |
| EP | 0 080 748 B1 | 7/1985 |
| EP | 0177183 | 4/1986 |
| EP | 0181041 | 5/1986 |
| EP | 0 080 223 BI | 7/1986 |
| EP | 0189838 | 8/1986 |
| EP | 0 066 944 B1 | 11/1986 |
| EP | 0 126 505 B1 | 1/1987 |
| EP | 0208491 | 1/1987 |
| EP | 0214531 | 3/1987 |
| EP | 0218272 | 4/1987 |
| EP | 0224971 | 6/1987 |
| EP | 0238216 | 9/1987 |
| EP | 0 272 033 A2 | 6/1988 |
| EP | 0 028 865 B2 | 3/1989 |
| EP | 0 164 514 B1 | 6/1989 |
| EP | 0322082 | 6/1989 |
| EP | 0322429 | 7/1989 |
| EP | 0351162 | 1/1990 |
| EP | 0368341 | 5/1990 |
| EP | 0 253 567 B1 | 12/1990 |
| EP | 0 241 985 B1 | 1/1991 |
| EP | 0404806 | 1/1991 |
| EP | 0418835 | 3/1991 |
| EP | 0464095 | 1/1992 |
| EP | 0 472 042 A1 | 2/1992 |
| EP | 0 185 427 B1 | 3/1992 |
| EP | 0 274 907 B1 | 8/1992 |
| EP | 0501375 | 9/1992 |
| EP | 0506791 | 10/1992 |
| EP | 0525610 | 2/1993 |
| EP | 0548228 | 6/1993 |
| EP | 0550695 | 7/1993 |
| EP | 0 656 058 B1 | 8/1993 |
| EP | 0561907 | 9/1993 |
| EP | 0 378 262 B1 | 12/1993 |
| EP | 0577973 | 1/1994 |
| EP | 0581839 | 2/1994 |
| EP | 0582478 | 2/1994 |
| EP | 0 241 984 B1 | 3/1994 |
| EP | 0594235 | 4/1994 |
| EP | 0 486 592 B1 | 6/1994 |
| EP | 0601005 | 6/1994 |
| EP | 0 378 261 B1 | 7/1994 |
| EP | 0610321 | 8/1994 |
| EP | 0610808 | 8/1994 |
| EP | 0 636 693 A2 | 2/1995 |
| EP | 0636170 | 2/1995 |
| EP | 0642574 | 3/1995 |
| EP | 0 564 476 B1 | 4/1995 |
| EP | 0 670 367 A1 | 9/1995 |
| EP | 0684304 | 11/1995 |
| EP | 0689589 | 1/1996 |
| EP | 0 357 280 B1 | 2/1996 |
| EP | 0699230 | 3/1996 |
| EP | 0699745 | 3/1996 |
| EP | 0703974 | 4/1996 |
| EP | 0717766 | 6/1996 |
| EP | 0 642 576 B1 | 7/1996 |
| EP | 0 727 485 A1 | 8/1996 |

| | | | | | |
|---|---|---|---|---|---|
| EP | 0726936 | 8/1996 | WO | WO9116424 | 10/1991 |
| EP | 0736085 | 10/1996 | WO | WO9210755 | 6/1992 |
| EP | 0736597 | 10/1996 | WO | WO 92/19707 A1 | 11/1992 |
| EP | 0 583 534 B1 | 3/1997 | WO | WO 93/00418 A1 | 1/1993 |
| EP | 0 525 239 B1 | 7/1997 | WO | WO 94/02597 A1 | 2/1994 |
| EP | 0786515 | 7/1997 | WO | WO 94/18314 A1 | 8/1994 |
| EP | 0 728 749 A2 | 8/1997 | WO | WO 94/19454 A2 | 9/1994 |
| EP | 0806472 | 11/1997 | WO | WO 94/23005 A1 | 10/1994 |
| EP | 0 693 471 B1 | 1/1998 | WO | WO9425577 | 11/1994 |
| EP | 0 694 521 B1 | 1/1998 | WO | WO9426881 | 11/1994 |
| EP | 0 818 450 A1 | 1/1998 | WO | WO 04/28102 A1 | 12/1994 |
| EP | 0 533 239 B1 | 4/1998 | WO | WO 94/27970 A1 | 12/1994 |
| EP | 0832176 | 4/1998 | WO | WO 94/28103 A1 | 12/1994 |
| EP | 0 628 630 B1 | 5/1998 | WO | WO 95/00626 A1 | 1/1995 |
| EP | 0842254 | 5/1998 | WO | WO9510603 | 4/1995 |
| EP | 0 410 498 B1 | 6/1998 | WO | WO 95/12655 A1 | 5/1995 |
| EP | 0 736 084 B1 | 9/1998 | WO | WO 95/14075 A1 | 5/1995 |
| EP | 0874894 | 11/1998 | WO | WO 95/14759 A1 | 6/1995 |
| EP | 0 581 751 B1 | 12/1998 | WO | WO 95/17498 A1 | 6/1995 |
| EP | 0 587 550 B1 | 12/1998 | WO | WO9525790 | 9/1995 |
| EP | 0 702 712 B1 | 12/1998 | WO | WO 95/26397 A1 | 10/1995 |
| EP | 0907713 | 4/1999 | WO | WO9528463 | 10/1995 |
| EP | 0925342 | 6/1999 | WO | WO9528469 | 10/1995 |
| EP | 0 828 762 B1 | 10/1999 | WO | WO 95/32232 A1 | 11/1995 |
| EP | 0 965 268 A1 | 12/1999 | WO | WO9535382 | 12/1995 |
| EP | 0995801 | 4/2000 | WO | WO 96/02633 A1 | 2/1996 |
| EP | 1022334 | 7/2000 | WO | WO9607723 | 3/1996 |
| EP | 1050579 | 11/2000 | WO | WO9621717 | 7/1996 |
| EP | 1065277 | 1/2001 | WO | WO9621718 | 7/1996 |
| EP | 1196530 | 1/2001 | WO | WO 96/23873 A1 | 8/1996 |
| EP | 1196531 | 1/2001 | WO | WO 96/31589 A1 | 10/1996 |
| EP | 0 780 466 B1 | 6/2001 | WO | WO 97/00324 A1 | 1/1997 |
| EP | 0 755 944 B1 | 10/2001 | WO | WO 97/00932 A1 | 1/1997 |
| EP | 1199356 | 4/2002 | WO | WO 97/05227 A1 | 2/1997 |
| EP | 0508034 | 10/2002 | WO | WO 97/18287 A1 | 5/1997 |
| EP | 1288282 | 3/2003 | WO | WO 97/25399 A1 | 7/1997 |
| GB | 1 154 730 | 1/1969 | WO | WO9723606 | 7/1997 |
| GB | 1 263 765 | 2/1972 | WO | WO 97/31085 A1 | 8/1997 |
| GB | 2 123 848 | 2/1984 | WO | WO 97/32958 A1 | 9/1997 |
| GB | 2167758 | 6/1986 | WO | WO 97/43377 A1 | 11/1997 |
| GB | 2200365 | 8/1988 | WO | WO 97/43424 A1 | 11/1997 |
| GB | 2211197 | 6/1989 | WO | WO9743387 | 11/1997 |
| GB | 2213153 | 8/1989 | WO | WO9801526 | 1/1998 |
| GB | 2228945 | 9/1990 | WO | WO9807820 | 2/1998 |
| GB | 2291058 | 1/1996 | WO | WO 98/13459 A1 | 4/1998 |
| GB | 2307695 | 6/1997 | WO | WO 98/13460 A1 | 4/1998 |
| GB | 2354771 | 4/2001 | WO | WO 98/13462 A1 | 4/1998 |
| GB | 2360041 | 9/2001 | WO | WO 98/13481 A1 | 4/1998 |
| JP | 10-095996 | 4/1998 | WO | WO98/15607 | 4/1998 |
| JP | 10-279991 | 10/1998 | WO | WO 98/17764 A1 | 4/1998 |
| JP | 11-021592 | 1/1999 | WO | WO9813481 | 4/1998 |
| JP | 11-050096 | 2/1999 | WO | WO9817767 | 4/1998 |
| JP | 11-061187 | 3/1999 | WO | WO9826078 | 6/1998 |
| JP | 11-181475 | 7/1999 | WO | WO 98/45396 A1 | 10/1998 |
| JP | 11-228992 | 8/1999 | WO | WO9844126 | 10/1998 |
| JP | 2000-023665 | 1/2000 | WO | WO99/00478 | 1/1999 |
| JP | 2000-023666 | 1/2000 | WO | WO 99/02702 A1 | 1/1999 |
| JP | 2000-023667 | 1/2000 | WO | WO9901531 | 1/1999 |
| JP | 2000-060544 | 2/2000 | WO | WO 99/06515 A1 | 2/1999 |
| JP | 2000-060546 | 2/2000 | WO | WO 99/06516 A1 | 2/1999 |
| JP | 2000-060547 | 2/2000 | WO | WO 99/09183 A1 | 2/1999 |
| JP | 2000-169897 | 6/2000 | WO | WO9909130 | 2/1999 |
| JP | 2000-178586 | 6/2000 | WO | WO9909131 | 2/1999 |
| JP | 2000-245466 | 9/2000 | WO | WO 99/20768 A1 | 4/1999 |
| JP | 2001-064693 | 3/2001 | WO | WO9919467 | 4/1999 |
| JP | 2001-064695 | 3/2001 | WO | WO9920723 | 4/1999 |
| JP | 2002-003892 | 1/2002 | WO | WO 99/23211 A1 | 5/1999 |
| RU | 2167193 | 5/2001 | WO | WO9923211 | 5/1999 |
| WO | WO8601831 | 3/1986 | WO | WO9924539 | 5/1999 |
| WO | WO8806183 | 8/1988 | WO | WO9929876 | 6/1999 |
| WO | WO8904842 | 6/1989 | WO | WO 97/24177 A1 | 7/1999 |
| WO | WO9011352 | 10/1990 | WO | WO9932613 | 7/1999 |
| WO | WO 91/02792 A1 | 3/1991 | WO | WO9942567 | 8/1999 |

| | | |
|---|---|---|
| WO | WO 99/43780 A1 | 9/1999 |
| WO | WO 99/43793 A1 | 9/1999 |
| WO | WO9943794 | 9/1999 |
| WO | WO 99/57250 A1 | 11/1999 |
| WO | WO 99/57252 A1 | 11/1999 |
| WO | WO 99/57254 A1 | 11/1999 |
| WO | WO 99/63035 A1 | 12/1999 |
| WO | WO 99/63036 A1 | 12/1999 |
| WO | WO 99/63037 A1 | 12/1999 |
| WO | WO 99/63038 A1 | 12/1999 |
| WO | WO 99/63041 A1 | 12/1999 |
| WO | WO 00/01826 A2 | 1/2000 |
| WO | WO 00/01831 A2 | 1/2000 |
| WO | WO 00/22103 A1 | 4/2000 |
| WO | WO0021504 | 4/2000 |
| WO | WO0024860 | 5/2000 |
| WO | WO0024877 | 5/2000 |
| WO | WO0029535 | 5/2000 |
| WO | WO0029560 | 5/2000 |
| WO | WO 00/39306 A2 | 7/2000 |
| WO | WO 00/42145 A1 | 7/2000 |
| WO | WO0041522 | 7/2000 |
| WO | WO0043476 | 7/2000 |
| WO | WO0043502 | 7/2000 |
| WO | WO0046333 | 8/2000 |
| WO | WO0046334 | 8/2000 |
| WO | WO0046335 | 8/2000 |
| WO | WO 00/60060 A2 | 10/2000 |
| WO | WO0060058 | 10/2000 |
| WO | WO0060059 | 10/2000 |
| WO | WO0075296 | 12/2000 |
| WO | WO0102530 | 1/2001 |
| WO | WO0114532 | 3/2001 |
| WO | WO0118180 | 3/2001 |
| WO | WO0123513 | 4/2001 |
| WO | WO0134784 | 5/2001 |
| WO | WO0147956 | 7/2001 |
| WO | WO 01/66712 A2 | 9/2001 |
| WO | WO0164852 | 9/2001 |
| WO | WO0172942 | 10/2001 |
| WO | WO0177274 | 10/2001 |
| WO | WO 01/88107 A2 | 11/2001 |
| WO | WO0183559 | 11/2001 |
| WO | WO0190393 | 11/2001 |
| WO | WO 01/96537 A2 | 12/2001 |
| WO | WO0202727 | 1/2002 |
| WO | WO0206508 | 1/2002 |
| WO | WO0210355 | 2/2002 |
| WO | WO0231124 | 4/2002 |
| WO | WO0233035 | 4/2002 |
| WO | WO0244313 | 6/2002 |
| WO | WO0248307 | 6/2002 |
| WO | WO02061026 | 8/2002 |
| WO | WO02064723 | 8/2002 |
| WO | WO02068575 | 9/2002 |
| WO | WO02068589 | 9/2002 |
| WO | WO02068597 | 9/2002 |
| WO | WO02077141 | 10/2002 |
| WO | WO02077143 | 10/2002 |
| WO | WO02078737 | 10/2002 |
| WO | WO02086112 | 10/2002 |
| WO | WO02092741 | 11/2002 |
| WO | WO02092797 | 11/2002 |
| WO | WO02096551 | 12/2002 |
| WO | WO03000625 | 1/2003 |
| WO | WO03002700 | 1/2003 |
| WO | WO03006602 | 1/2003 |
| WO | WO03016535 | 2/2003 |
| WO | WO03018734 | 3/2003 |

OTHER PUBLICATIONS

Seffernick et al., J. Bacteriol., 183(8):2405-2410 (2001).
G. Jensen, "The Development and Application of a New Oxidation Stable Detergent Amylase", SOFW-Journal, vol. 123, pp. 723-731 (1997).
D. J. Lipman et al., "Rapid and Sensitive Protein Similarity Searches", Science. vol. 227, pp. 1435-1441 (1985).
Handbuch von Fritsch, Sambrook and Maniatis, "Molecular cioning: a laboratory manual", Cold Spring Harbour Laboratory Press, New York, 1989.
von H. Ihlig, Industrial enzymes and their applications, Wiley-Verlag, New York, (1998).
K. H. Wellhauber, "Praxis der Sterilisation, Desinfektion-Konservierung:Keimidentifizierung-Betriebshygiene", $5^{th}$ Edition, Stuttgart-New York: thieme (1995).
P. Finkel, "Formulierung kosmetischer Sonnenschutzmittel", SOFW-Journal. vol. 11, p. 543 (1996).
Goornall et al., "Determination of Serum Proteins By Means of the Biuret Reaction", J. Biol. Chem, vol. 177, pp. 751-766 (1948).
Verbeek et al., Zur Bestimmung der proteolytischen Aktivitat in Enzymkonzentraten und enzymhaltigen Wasch-, Spul-und Reinigungsmittein, Tenside, vol. 7, pp. 125-132 (1970).
S. F. Altschul et al., "Gapped BLAST and PSI-BLAST: a new generation of protein database search program", Nucleic Acids Research, vol. 25, pp. 3389-3402, (1997).
Tsukamoto et al., "Nucleotide Sequence of the Maltohexaose-Producing Amylase Gene from an Alkalophllic Cacilius sp. #707 and Structural Similarity to Liquiefying Type α-Amylases", Biochemical and Biophysical Research Communications, vol. 151, pp. 25-31 (1988).

* cited by examiner

FIG. 1

```
                                                                                                          70
1  (1)    --MRKRKNGLISILLAFLLVLTSIPFTSANVEAHHNGTNGTMQYFEWYLPNDGNHWNRLRSDASNLKDK
1  (1)    MKMRTGKKGFLSILLAFLLVITSIPFTLVDVEAHHNGTNGTMQYFEWYLPNDGNHWNRLNSDASNLKSK
2  (1)    ------------------------------HHNGTNGTMQYFEWYLPNDGNHWNRLRDDAANLKSK
3  (1)    ------------------------------HHNGTNGTMQYFEWHLPNDGNHWNRLRDDASNLRNR
4  (1)

140
1  (69)   GITAVWIPPAWKGASQNDVGYGAYDLYDLGEFNQKGTVRTKYGTRNQLQAAVTALKSNGIQVYGDVVMNH
1  (71)   GITAVWIPPAWKGASQNDVGYGAYDLYDLGEFNQKGTVRTKYGTRNQLQAAVTALKSNGIQVYGDVVMNH
2  (38)   GITAVWIPPAWKGTSQNDVGYGAYDLYDLGEFNQKGTVRTKYGTRSQLQAAVTSLKNNGIQVYGDVVMNH
3  (38)   GITAIWIPPAWKGTSQNDVGYGAYDLYDLGEFNQKGTVRTKYGTRSQLESAIHALKNNGVQVYGDVVMNH
4

210
1  (139)  KGGADATEMVRAVEVNPSNRNQEVSGDYTIEAWTKFDFPGRGNTHSNFKWRWYHFDGVDWDQSRQLQNRI
1  (141)  KGGADATEMVRAVEVNPNNRNQEVTGEYTIEAWTRFDFPGRGNTHSSFKWRWYHFDGVDWDQSRRLNNRI
2  (108)  KGGADGTEIVNAVEVNRSNRNQETSGEYAIEAWTKFDFPGRGNNHSSFKWRWYHFDGTDWDQSRQLQNKI
3  (108)  KGGADATENVLAVEVNPSNRNQEISGDYTIEAWTKFDFPGRGNTYSDFKWRWYHFDGVDWDQSRQFQNRI
4

280
1  (209)  YKFRGDGKGWDWEVDTENGNYDYLMYADIDMDHPEVVNELRNWGVWYTNTLGLDGFRIGAVKHIKYSFTR
1  (211)  YKFRGHGKAWDWEVDTENGNYDYLMYADIDMDHPEVVNELRNWGVWYTNTLGLDGFRIDAVKHIKYSFTR
2  (178)  YKFRGTGKAWDWEVDTENGNYDYLMYADVDMDHPEVIHELRNWGVWYTNTLNLDGFRIDAVKHIKYSFTR
3  (178)  YKFRGDGKAWDWEVDSENGNYDYLMYADVDMDHPEVVNELRRWGEWYTNTLNLDGFRIDAVKHIKYSFTR
4
```

FIG. 1

```
281                                                                                                      350
1  (279)  DWLTHVRNTTGKNMFAVAEFWKNDIGAIENYLSKTNWNHSVFDVPLHYNLYNASRSGGNYDMRQIFNGTV
2  (281)  DWINHVRSATGKNMFAVAEFWKNDLGAIENYLQKTNWNHSVFDVPLHYNLYNASKSGGNYDMRNIFNGTV
3  (248)  DWLTHVRNTTGKPMFAVAEFWKNDLGAIENYLNKTSWNHSAFDVPLHYNLYNASNSGGYYDMRNILNGSV
4  (248)  DWLTHVRNATGKEMFAVAEFWKNDLGALENYLNKTNWNHSVFDVPLHYNLYNASNSGGNYDVAKLLNGTV 351                                                                                                      420
1  (349)  VQRHPTHAVTFVDNHDSQPEEALESFVEEWFKPLACALTLTRDQGYPSVFYGDYYGIPTHGVPAMKSKID
2  (351)  VQRHPSHAVTFVDNHDSQPEEALESFVEEWFKPLAYALTLTREQGYPSVFYGDYYGIPTHGVPAMRSKID
3  (318)  VQKHPTHAVTFVDNHDSQPGEALESFVQQWFKPLAYALVLTRIQGYPSVFYGDYYGIPTHGVPAMKSKID
4  (318)  VQKHPMHAVTFVDNHDSQPGESLESFVQEWFKPLAYALILTREQGYPSVFYGDYYGIPTHSVPAMKAKID 421                                                                                                      490
1  (419)  PILEARQKYAYGKQNDYLDHHNMIGWTREGNTAHPNSGLATIMSDGPGGNKWMYVGRNKAGQVWRDITGN
2  (421)  PILEARQKYAYGKQNDYLDHHNIIGWTREGNTAHPNSGLATIMSDGAGGSKWMFVGRNKAGQVWSDITGN
3  (388)  PLLQARQTFAYGTQHDYFDHHDIIGWTREGNSSHPNSGLATIMSDGPGGNKWMYVGKNKAGQVWRDITGN
4  (388)  PILEARQNFAYGTQHDYFDHHNIIGWTREGNTHPNSGLATIMSDGPGGEKWMYVGQNKAGQVWHDITGN 491             518
1  (489)  RSGTVTIINADGWGNFSVNGGSVSIWVNN     (SEQ ID NO: 2)
2  (491)  RTGTVTIINADGWGNFSVNGGSVSIWVNK     (SEQ ID NO: 3)
3  (458)  RTGTVTIINADGWGNFSVNGGSVSVWVKQ     (SEQ ID NO: 4)
4  (458)  KPGTVTIINADGWANFSVNGGSVSIWVKR     (SEQ ID NO: 5)
```

AMYLOLYTIC ENZYME EXTRACTED FROM *BACILLUS* SP. A 7-7 (DSM 12368) AND WASHING AND CLEANING AGENTS CONTAINING THIS NOVEL AMYLOLYTIC ENZYME

CROSS-REFERENCE TO RELATED APPLICATIONS

This application is a divisional of U.S. application Ser. No. 11/590,976, filed Nov. 1, 2006, which issued as U.S. Pat. No. 7,303,905 on Dec. 4, 2007, which is a divisional of U.S. application Ser. No. 10/343,212, filed Jan. 28, 2003, which issued as U.S. Pat. No. 7,153,818 on Dec. 26, 2006, which is the National Stage entry under 35 U.S.C. §371 of International Application No. PCT/EP01/08359, filed on Jul. 19, 2001, which claims priority to German Application No. 100 36 752.2, filed on Jul. 28, 2000, and German Application No. 100 36 753.4, filed on Jul. 28, 2000.

SUBMISSION ON COMPACT DISC

The contents of the following submission on compact discs are incorporated herein by reference in its entirety: two copies of the Sequence Listing (COPY 1 and COPY 2) on compact disc and a computer readable form transferred pursuant to 37 C.F.R. §1.821(e) from the last-filed computer readable form of U.S. application Ser. No. 11/590,970, filed Nov. 1, 2006, each containing: file name: Sequence List-H 04713 DIV (13744-50), date recorded: Oct. 22, 2007, size: 27 KB.

This invention relates to a new amylolytic enzyme from the microorganism *Bacillus* sp. A 7-7 (DSM 12368) and sufficiently similar proteins with amylolytic activity, to processes for their production and to various potential applications for these proteins. Over and above the potential applications mentioned, they may be further developed for other, above all industrial purposes. More particularly, the present invention relates to detergents/cleaners containing such amylolytic proteins, to processes for cleaning textiles or hard surfaces in which the amylolytic proteins or corresponding compositions are involved and to their use for cleaning textiles or hard surfaces.

α-Amylases (E.C. 3.2.1.1) hydrolyze internal α-1,4-glycosidic bonds of starch and starch-like polymers, such as amylose, amylopectin or glycogen for example, to form dextrins and β-1,6-branched oligosaccharides. They are among the most important industrially used enzymes. There are two reasons for this. First, like many substrate-degrading enzymes, they are released from microorganisms into the surrounding medium so that they can be isolated from the culture medium relatively easily on an industrial scale by fermentation and purification. Second, amylases are required for a broad range of applications.

One important industrial use of α-amylase is the production of glucose syrup. Other applications are, for example, as active components in detergents/cleaners, the treatment of raw materials in textile manufacture, the production of adhesives and the production of sugar-containing foods or food ingredients.

Enzymes such as proteases, amylases, lipases or cellulases have been used as active components in detergents/cleaners for decades. Their particular contribution to the washing/cleaning performance of the particular composition is, in the case of protease, an ability to degrade protein-containing soils, in the case of amylase the degradation of starch-containing soils and, in the case of lipase, its lipolytic activity. Cellulases are preferably used in detergents, above all by virtue of their contribution to the multiple wash-cycle performance of a detergent and for their fiber effect on textiles. The particular hydrolysis products are attacked, dissolved, emulsified or suspended by the other ingredients of the detergent or, by virtue of their relatively high solubility, are floated out with the wash liquor so that synergistic effects occur between the enzymes and the other constituents.

An α-amylase commonly used in detergents/cleaners is the α-amylase from *Bacillus licheniformis*. For example, the corresponding products of Novo Nordisk A/S, Bagsvaerd, Denmark and Genencor Int., Rochester, N.Y., USA are known commercially as Termamyl® and Purastar®, respectively. The homolog isolated from *B. subtilis* or *B. amyloliquefaciens* and disclosed in US patent application U.S. Pat. No. 1,227,374 is marketed by Novo Nordisk A/S under the name of BAN®.

This amylase molecule or its close relatives have been further developed in numerous inventions which addressed the problem of optimizing their enzymatic properties for specific applications through various molecular-biological modifications. Such optimizations can relate, for example, to the substrate specificities, to the stability of the enzyme under various reaction conditions or to the enzymatic activity itself. The following patent applications are mentioned as examples of such optimizations for specific applications: EP 0 410 498 for the sizing of textiles and WO 96/02633 for the liquefaction of starch.

Above all, however, α-amylases have been further developed in regard to their use in detergents/cleaners. The following patent applications are mentioned as just some examples of this: the amylases of WO 99/02702 are more stable at relatively high temperatures than the starting molecule. The enzymes of WO 99/23211 are stable at high pH values, in the presence of calcium ions and at relatively high temperatures. The α-amylases of WO 97/43424 show a modified binding capacity for calcium ions and hence modified enzymatic properties. The mutagenesis process of WO 99/20768 leads to α-amylase variants which are particularly stable in the presence of detergent ingredients. With modifications of the type in question, a change in individual enzymatic properties almost always has an effect on other properties and on the washing performance of the particular enzyme. One example of an optimization product obtained in this way which is now on the market is Duramyl® (WO 94/02597) with reduced sensitivity to oxidation (Novo Nordisk A/S, Bagsvaerd, Denmark; SÖFW-Journal 123, (1997), pp. 723-731).

Since developments which merely comprise the optimization of only a few known starting enzymes may possibly be limited in the results obtained, there has been a parallel, intensive search for comparable enzymes from other natural sources. This search has identified starch-splitting enzymes, for example from *Pimelobacter, Pseudomonas* and *Thermus* for food production, cosmetic and pharmaceutical products (EP 0 636 693), from *Rhizobium, Arthrobacter, Brevibacterium* and *Micrococcus* (EP 0 628 630), from *Pyrococcus* (WO 94/19454) and *Sulfolobus* for starch liquefaction at high temperatures or under highly acidic reaction conditions (EP 0 727 485 and WO 96/02633). Amylases from *Bacillus* sp. have been found (WO 95/26397 and WO 97/00324) for use at alkaline pH values. By virtue of their low sensitivity to detergents, other amylases from various *Bacilli* (EP 0 670 367) are suitable for use in detergents/cleaners.

By virtue of their origin, enzymes from newly opened organisms are possibly more suitable than the few established enzymes for further development towards specific applications. One example of this is the amylase from *Thermoalcali-*

*bacter* (WO 98/13481) of which the natural activity is largely immune to calcium ions so that, from the outset, it has the right qualifications for use in detergents.

Further optimizations of the enzymes isolated from natural sources for the particular application can be undertaken, for example, by molecular-biological methods (for example according to U.S. Pat. No. 5,171,673 or WO 99/20768) or through chemical modifications (DE 4013142). Patent application WO 99/43793, for example, describes a further development of the known Novamyl® α-amylase. In this document, sequence similarities between Novamyl® and known cyclodextrin glucanotransferases (CGTases) are used to construct a host of related molecules by microbiological techniques. These related molecules are α-amylases with additional CGTase-specific consensus sequences (boxes) and functions or, conversely, CGTases with additional regions and functions typical of α-amylases or chimeras of both molecules. The object of this development is to optimize Novamyl® for these applications.

Patent application WO 99/57250 discloses another method for improving the washing performance of detergent enzymes, such as lipases, cellulases, proteases, amylases or even CGTases. The principle described therein consists in covalently bonding the particular enzymes to cellulose binding domains (CBDs) of bacterial origin via a non-amino acid linker. These ensure that the enzyme acts on the surface of the textile with greater intensity. WO 99/57252 includes other possible linkers in this concept while WO 99/57254 includes other enzymes such as, for example, glycosyl transferases or acyl transferases which are bound to the CBDs either to form a chimeral protein or via the linkers mentioned in WO 99/57252.

Every amylase used for detergents has its own performance profile which is reflected in the fact that some soils are removed more effectively by one enzyme while other soils are removed more effectively by another enzyme. This further demonstrates the necessity to enrich the art with other amylolytic enzymes which also have their own performance spectra. This necessity also arises from the changing habits and demands of the consumer, according to which there is, for example, an increasing demand for detergents for cleaning at low and medium temperatures.

In addition, new enzymes which can be obtained from organisms hitherto undeveloped for this purpose may be used as a starting product for further genetic engineering modifications by "protein engineering". Their objective is to produce properties which the hitherto known enzymes or the detergent enzymes derived from them do not or cannot possess.

On the other hand, however, natural enzymes which, from the outset, show a certain washing or cleaning performance in conjunction with typical detergent ingredients seem to be particularly suitable candidates for such optimizations.

Despite all these developments, however, there is still a need to find other amylolytic enzymes, which a priori have a broad application spectrum and may be used as a starting point for specific further developments, in addition to the few natural amylolytic enzymes which are actually used on an industrial scale either as such or in the form of further developments.

Accordingly, the problem addressed by the present invention was to identify a natural α-amylase hitherto undescribed which would be suitable even for industrial applications, more particularly in detergents/cleaners, or which could be used as a basis for application-specific further developments.

A secondary problem was to obtain the nucleic acid coding for such an α-amylase because this would be essential both for the biotechnological production and for the further development of these enzymes.

Another secondary problem was to find an organism which would naturally produce the particular α-amylase.

Another secondary problem was to enable the α-amylase found to be biotechnologically produced.

Another secondary problem was to provide detergents/cleaners of which the washing or cleaning performance would be improved by the α-amylase found, i.e. of which the washing or cleaning performance could be at least partly attributed to the amylolytic protein according to the invention.

Further secondary problems were to provide corresponding washing/cleaning processes and to point out corresponding potential uses.

Another secondary problem was to define further potential industrial applications for an α-amylase which, primarily, appeared suitable for use in detergents/cleaners.

The solution to the problem stated above and hence a first embodiment of the invention lies in amylolytic proteins of which the amino acid sequence is at least 96%, preferably at least 98% and more preferably 100% identical with the amino acid sequence shown in SEQ ID NO. 2, more particularly over the region which corresponds to amino acids 32 to 516 of SEQ ID NO. 2.

This includes amylolytic proteins derived from a nucleotide sequence which is at least 85%, preferably at least 90% and more preferably 100% identical with the nucleotide sequence shown in SEQ ID NO. 1, more particularly over the region which corresponds to amino acids 32 to 516 of SEQ ID NO. 2. Also included are proteolytic enzymes which are sufficiently similar to these amylolytic proteins or which can be derived by methods known per se. Preferred representatives can naturally be isolated from microorganisms, more particularly gram-positive bacteria of the genus *Bacillus*, especially the species *Bacillus* sp. A 7-7 and more particularly *Bacillus* sp. A 7-7 (DSM 12368).

A second embodiment of the invention are nucleic acids coding for amylolytic proteins of which the nucleotide sequence is at least 85%, preferably at least 90% and more preferably 100% identical with the nucleotide sequence shown in SEQ ID NO. 1, more particularly over the region which corresponds to amino acids 32 to 516 of SEQ ID NO. 2. These preferably include—correspondingly—the nucleic acids which code for the particular proteins of the first embodiment of the invention.

A third embodiment of the invention are the natural organisms which form a protein or derivative of the first embodiment or which contain nucleic acids coding for that protein or derivative. A particularly preferred embodiment is the strain *Bacillus* sp. A 7-7 which has been lodged under the name DSM (12368).

A fourth embodiment of the invention are vectors with the nucleic acids of the second embodiment, host cells transformed with such vectors and any biotechnological processes for the production of a protein or derivative of the first embodiment of the invention.

A fifth embodiment of the invention are detergents/cleaners which are characterized in that they contain a protein or derivative of the first embodiment. These preferably include detergents/cleaners which contain the amylolytic protein or derivative in quantities of 0.000001% by weight to 5% by weight and more particularly 0.00001 to 3% by weight, which contain other enzymes, which are present in supply forms known per se or in which the amylolytic activity performs a function for the release of the ingredients of the detergent/cleaner or is itself controlled.

A sixth embodiment of the invention are processes for cleaning textiles or hard surfaces which are characterized in that an amylolytic protein or derivative of the first embodiment becomes active in at least one of the process steps. Detergents/cleaners of the fifth embodiment are preferably used for this purpose and the amylolytic protein or derivative is preferably used in a quantity of 0.01 mg to 200 mg per application and more particularly in a quantity of 0.02 mg to 100 mg per application in the particular process step.

A seventh embodiment of the invention are corresponding potential applications of the proteins or derivatives of the first embodiment or the detergents/cleaners of the fifth embodiment of the invention for cleaning textiles or hard surfaces or for releasing the ingredients of corresponding detergents/cleaners; preferably in a quantity of 0.01 mg to 200 mg and more particularly 0.02 mg to 100 mg of the amylolytic protein or derivative per application in a dishwasher or washing machine.

An eighth embodiment of the invention are further potential industrial uses for the α-amylases found. These include processes for liquefying starch, more particularly for ethanol production, temporary bonding processes and various potential applications, more particularly for the treatment of raw materials or intermediate products in textile manufacture, more particularly for desizing cotton, for the production of linear and/or short-chain oligosaccharides, for the hydrolysis of cyclodextrins, for the release of low molecular weight compounds from polysaccharide carriers or cyclodextrins, for the production of foods and/or food ingredients, for the production of animal feeds and/or animal feed ingredients and for dissolving starch-containing adhesive bonds.

A protein in the context of the present invention is a substantially linear polymer made up of the natural amino acids which generally assumes a three-dimensional structure for performing its function. In the present specification, the 19 proteinogenic, naturally occurring L-amino acids are designated by the internationally accepted 1- and 3-letter codes.

An enzyme in the context of the present invention is a protein which performs a certain biochemical function. Amylolytic proteins or enzymes with an amylolytic function are understood to be those which hydrolyze α-1,4-glycosidic bonds of polysaccharides, more particularly those which lie within the polysaccharides. Accordingly, they are also referred to as α-1,4-amylases (E.C. 3.2.1.1).

Many proteins are formed as so-called preproteins, i.e. together with a signal peptide. By this is meant the N-terminal part of the protein of which the function generally is to guarantee the release of the protein formed from the producing cell into the periplasm or the surrounding medium and/or its correct folding. The signal peptide is then split off from the rest of the protein under natural conditions by a signal peptidase so that it performs its actual catalytic activity without the N-terminus initially present. The native α-amylase from *Bacillus* sp. A7-7 (DSM 12368), for example, is 516 amino acids long, as shown in SEQ ID NO. 2. As shown in SEQ ID NO. 1, the signal peptide of this enzyme comprises 31 amino acids so that the mature enzyme has a length of 485 amino acids.

By virtue of their enzymatic activity, the mature peptides, i.e. the enzymes processed after their production, are preferred to the preproteins for industrial applications.

Proproteins are inactive precursors of proteins. Their precursors with signal frequency are known as pre-proproteins.

In the context of the present invention, nucleic acids are the molecules naturally made up of nucleotides which serve as information carriers and which code for the linear amino acid sequence in proteins or enzymes. They may be present as a single strand, as a single strand complementary to that single strand or as a double strand. As the naturally more permanent information carrier, the nucleic acid DNA is preferred for molecular biological work. By contrast, for carrying out the invention in a natural environment, for example in an expressing cell, an RNA is formed so that RNA molecules essential to the invention also represent embodiments of the invention.

With DNA, the sequences of both complementary strands in all three reading frames have to be considered. Another factor to be considered is that different codon triplets can code for the same amino acids, so that a certain amino acid sequence can be derived from several different nucleotide sequences possibly having only minimal identity (degenerateness of the genetic code). In addition, different organisms show differences in the use of this codon. For these reasons, both amino acid sequences and nucleotide sequences have to be included in the consideration of the scope of protection and disclosed nucleotide sequences should only be regarded as an exemplary coding for a certain amino acid sequence.

The unit of information corresponding to a protein is also referred to as a gene in the present specification.

With the help of methods now generally known, such as for example chemical synthesis or the polymerase chain reaction (PCR), in conjunction with molecular-biological and/or protein-chemical standard methods, the expert is able to produce the corresponding nucleic acids up to and including complete genes on the basis of known DNA and/or amino acid sequences. Such methods are known, for example, from the "Lexikon der Biochemie", Spektrum Akademischer Verlag, Berlin, 1999, Vol. 1, pp. 267-271 and Vol. 2., pp. 227-229.

Changes in the nucleotide sequence, which can be produced for example by molecular-biological methods known per se, are referred to as mutations. Depending on the type of change, mutations are known, for example, as deletion, insertion or substitution mutations or mutations where various genes or parts of genes are fused together ("shuffling"); these are gene mutations. The associated organisms are known as mutants. The proteins derived from mutated nucleic acids are referred to as variants. For example, deletion, insertion or substitution mutations or fusions lead to deletion-, insertion-, substitution-mutated or fusion genes and, at the protein level, to corresponding deletion, insertion or substitution variants or fusion proteins.

Fragments are understood to be any proteins or peptides which are smaller than natural proteins or those which correspond to completely translated genes and which, for example, can also be synthetically obtained. On the basis of their amino acid sequences, they can be assigned to the particular complete proteins. For example, they may assume identical structures or may perform proteolytic activities or partial activities such as, for example, the complexing of a substrate. Fragments and deletion variants of starting proteins are basically the same. Whereas fragments are relatively small pieces, deletion mutants lack only short regions and hence only individual partial functions.

In the context of the present invention, chimeral or hybrid proteins are proteins made up of elements which naturally emanate from different polypeptide chains from the same organism or from different organisms. This procedure is also known as shuffling or fusion mutagenesis. The object of such a fusion can be, for example, to produce or modify a certain enzymatic function with the aid of the fused-on part of the protein.

Proteins obtained by insertion mutation are understood to be variants which have been obtained by methods known per se by insertion of a nucleic acid or protein fragment into the starting sequences. Because they are basically the same, they may be assigned to the chimeral proteins from which they differ solely in the size ratio of the unchanged part of the protein to the size of the entire protein. In insertion-mutated proteins, the proportion of foreign protein is lower than in chimeral proteins.

Inversion mutagenesis, i.e. partial sequence inversion, may be regarded as a special form of both deletion and insertion. The same applies to a regrouping of various parts of the molecule which differs from the original amino acid sequence. They may be regarded as a deletion variant, as an insertion variant and as a shuffling variant of the original protein.

Derivatives in the context of the present invention are proteins of which the pure amino acid chain has been chemically modified. Such derivatizations can be carried out, for example, biologically in connection with protein biosynthesis by the host organism. Molecular-biological methods may be used for this purpose. They may also be carried out chemically, for example by the chemical conversion of a side chain of an amino acid or by covalent bonding of another compound to the protein. This compound may be, for example, another protein which is bound to proteins according to the invention, for example by bifunctional chemical compounds. Derivatization is also understood to include covalent bonding to a macromolecular carrier.

In the context of the invention, all enzymes, proteins, fragments and derivatives come under the collective heading of proteins unless they need to be explicitly referred to as such.

Vectors in the context of the invention are understood to be elements consisting of nucleic acids which contain an interesting gene as a characteristic nucleic acid region. They are able to establish this in a species or a cell line over several generations or cell divisions as a stable genetic element which replicates independently of the rest of the genome. Vectors are special plasmids, i.e. circular genetic elements, particularly where they are used in bacteria. In genetic engineering, a distinction is drawn between, on the one hand, vectors which are used for storage hence also for genetic work so to speak (the so-called cloning vectors) and, on the other hand, vectors which perform the function of producing the interesting gene in the host cell, i.e. facilitating the expression of the particular protein. These vectors are known as expression vectors.

By comparison with known enzymes, which are lodged for example in generally accessible data banks, characteristic molecule parts such as structural elements, for example, or the enzymatic activity of a studied enzyme can be deduced from the amino acid or nucleotide sequence. Such a comparison is made by assigning similar sequences in the nucleotide or amino acid sequences of the studied proteins to one another. This is known as homologizing. A tabular assignment of the particular positions is known as alignment. In the analysis of nucleotide sequences, both complementary strands and all three possible reading frames have to be taken into consideration, as do the degenerateness of the genetic code and the organism-specific codon usage. Alignments are now produced by computer programs, for example by the FASTA or BLAST algorithms; this procedure is described, for example, by D. J. Lipman and W. R. Pearson (1985) in Science, Vol. 227, pp. 1435-1441. A compilation of all positions in accord in the compared sequences is known as a consensus sequence.

Such a comparison also provides information on the similarity or homology of the compared sequences to one another. This is expressed in percent identity, i.e. the proportion of identical nucleotides or amino acid residues at the same positions. A more broadly defined notion of homology includes the conserved amino acid exchanges in this value. Percent identity then becomes percent similarity. Such assertions can be made about whole proteins or genes or only about individual regions.

Homologous regions of different proteins are generally those with the same structural elements and/or functions which can be recognized by accordances in the primary amino acid sequence. It extends to complete identities in very small regions, so-called boxes, which comprise only a few amino acids and which generally perform essential functions for the overall activity. By functions of the homologous regions are meant very small partial functions of the function performed by the protein as a whole, such as for example the formation of individual hydrogen bridge bonds for complexing a substrate or transition complex.

The enzymatic activity can be qualitatively or quantitatively modified by other regions of the protein which do not take part in the actual reaction. This concerns, for example, the enzyme stability, activity, reaction conditions or substrate specificity.

Accordingly, the definition of an amylolytic protein according to the invention does not apply just to one with the pure function of carrying out the hydrolysis of a α-1,4-glycosidic bonds which are attributable to the few amino acid residues of a probable catalytically active center. It also encompasses all the functions supporting the hydrolysis of an α-1,4-glycosidic bond. Such functions can be performed, for example, by individual peptides and by one or more individual parts of a protein by acting on the actual catalytically active regions. The definition of the amylolytic function also encompasses such modifying functions alone. This is because, on the one hand, it is not known exactly which amino acid residues of the protein according to the invention actually catalyze the hydrolysis and, on the other hand, certain individual functions cannot be definitively excluded from the outset from participation in the catalysis. The auxiliary functions or partial activities include, for example, the binding of a substrate, an intermediate or end product, the activation or the inhibition or imparting of a controlling effect on the hydrolytic activity. This can also involve, for example, the formation of a structural element which lies far from the active center or a signal peptide of which the function concerns the release of the protein formed from the cell and/or its correct folding and without which no enzyme capable of functioning is generally formed in vivo. Overall, however, α-1,4-glycosidic bonds of starch or starch-like polymers must be hydrolyzed.

The performance of an enzyme is understood to be its effectiveness in the technical field under consideration. This is based on the actual enzymatic activity, but is also dependent on other factors relevant to the particular process. These include, for example, stability, substrate binding, interaction with the material carrying the substrate or interactions with other ingredients, more particularly synergisms. For example, consideration of whether an enzyme is suitable for use in detergents will also include an assessment of its contribution to the washing or cleaning performance of a detergent or cleaner formulated with other constituents. An enzyme can be further developed and optimized for various technical applications using molecular-biological techniques known per se, more particularly those mentioned in the foregoing.

Under the Budapest Treaty over the international recognition of the lodging of microorganisms of 28 Apr. 1977, *Bacil-* lus sp. A 7-7 was deposited for the present invention on 5 Aug. 1998 in the Deutsche Sammlung von Mikroorganismen and Zellkulturen GmbH (German Collection of Microorganisms and Cell Cultures GmbH), Inhoffenstralβe 7 B, 38124 Braunschweig, Germany (DSMZ). The deposited *Bacillus* sp. A 7-7 carries the registration number DSM 12368 (DSM 98-587). The deposit was made in accordance with the terms and provisions of the Budapest Treaty relating to deposit of microorganisms and was made for a term of at least thirty (30) years and at least (5) years after the most recent request for the furnishing of a sample of the deposit is received by the depository, or for the enforceable life of the patent, whichever is longer, and will be replaced if it becomes non-viable during that period. The key data relating to the features of this biological material, as determined by the DSMZ on the lodgement date, are set out in Table 1 below.

TABLE 1

Microbiological properties of *Bacillus* sp. A 7-7 (DSM 12368) (as determined by the DSMZ on the Sep. 10, 1998)

| Property | Result |
| --- | --- |
| Cell form | Rodlets |
| width [μm] | 3.0-4.5 |
| length [μm] | 0.8-1.0 |
| Spores | Positive/oval |
| Sporangium | Slight swollen |
| Oxidase | Positive |
| Catalase | Positive |
| Anaerobic growth | Positive |
| VP reaction | Negative |
| pH in VP medium | 9.1 |
| Growth at 40° C. | Positive/weak |
| Growth at 50° C. | Negative |
| Growth in | |
| medium pH 7.0 | Negative |
| NaCl 2% | Positive |
| NaCl 5% | Positive |
| NaCl 7% | Positive |
| NaCl 10% | Positive |
| NaCl 12% | Negative |
| NaCl 16% | Negative |
| lysozyme medium | Positive |
| Acid from | |
| D-glucose | Negative |
| L-arabinose | Negative |
| D-xylose | Negative |
| D-mannitol | Positive |
| D-fructose | Positive |
| Hydrolysis of | |
| starch | Positive |
| gelatin | Positive |
| casein | Positive |
| tyrosine | Weak |
| Tween 80 | Positive |
| Tween 60 | Positive |
| Tween 40 | Positive |
| Tween 20 | Negative |
| Lecithinase | Positive |
| Pullulan | Positive |
| Hydrolysis of hippurate | Positive |
| Esculin | Positive |
| Utilization of | |
| citrate | Positive |
| Propionate | Positive |
| NO$_2$ from NO$_3$ | Positive |
| Indole reaction | Negative |
| Phenyl alanine desaminase | Negative |
| RESULT | *Bacillus* sp. (RNA group VI, alcaliphilic) |
| Remarks | The physiological test results point to the species *B. alcalophilus* or *B. horikoshii*, but cannot clearly identify any of the species mentioned. The strain showed 2 colony forms which were determined as variants of one and the same species by fatty acid analysis. Partial sequencing of the 16S rDNA produced 94.8% accordance with *B. alcalophilus*. Strain A 7-7 is probably the representative of a new species. |

Now, as has been surprisingly found over and above this characterization, the amylolytic enzyme produced by this strain has properties which predestine it for use in a number of industrial processes. In addition, the strain has properties which favorably affect cultivatability.

As shown in detail in Example 2, the amylolytic enzyme according to the invention of the strain *Bacillus* sp. A 7-7 (DSM 12368) may be biochemically characterized as follows: as a mature protein, it has an apparent molecular weight of 58 kD in denaturing SDS polyacrylate gel electrophoresis whereas a molecular weight of around 59 kD can be derived from the protein sequence of 516 amino acids (SEQ ID NO. 2) and one of 55.5 kD after removal of the signal peptide comprising 31 amino acids. According to isoelectric focussing, the isoelectric point of the mature protein is 6.0. It has amylolytic activity. It is stable to incubation for 10 mins. at pH 10/50° C. 50% residual activity is observed at 60° C. The enzyme is largely stable to incubation for 10 minutes at 40° C./pH 5-12, the best stability being observed at pH 9. In the presence of 0.1% SDS, the enzyme shows 98% residual activity after incubation for 15 minutes at pH 10/50° C. In the presence of an additional 10 HPE/ml protease activity and after incubation for 15 mins. at pH 10/50° C., the enzyme still has 74% residual activity.

Accordingly, the present invention provides a naturally occurring enzyme which must be regarded as α-amylase on the strength of its sequence homologies to the hitherto known enzymes and its enzymatic activity. In principle, it may be used for any applications which require an amylolytic function. It is particularly suitable for applications involving alkaline pH values and medium temperature ranges, more particularly pH values above 9 and/or temperatures above 40° C. The application spectrum is extended by the comparatively high stability of the enzyme to detergents and proteases. Accordingly, it appears to be particularly suitable for use in detergents/cleaners.

The nucleotide sequence of this enzyme is shown in the sequence protocol under the heading SEQ ID NO. 1. Accordingly, it is available, for example, for further developments using molecular-biological methods known per se. The amino acid sequence of the enzyme is shown in the sequence protocol under the heading SEQ ID NO. 2.

Comparable amylolytic proteins are also embodiments of the present invention and are claimed insofar as they have protein or DNA sequences which lie within the range of similarity to the sequences shown in SEQ ID NO. 1 and/or SEQ ID NO. 2. This similarity range encompasses all proteins of which the amino acid sequence is at least 96%, 96.5%, 97%, 97.5%, 98%, 98.5%, 99%, 99.5% or 100% identical with the amino acid sequence shown in SEQ ID NO. 2. The similarity range also encompasses all proteins of which the nucleotide sequence is at least 85%, 87.5%, 90%, 92.5%, 95%, 96%, 97%, 98%, 99% or 100% identical with the nucleotide sequence shown in SEQ ID NO. 1. This applies in particular to those partial ranges of the protein which relate to amino acids 32 to 516.

The nearest similar protein known on Mar. 17, 2000 is the α-amylase from *Bacillus alcalophilus* with the registration number P 19571 in the Swiss-Prot data bank (Geneva Bioinformatics (GeneBio) S.A., Geneva, Switzerland). This protein has a sequence homology of 93.4% identity at protein level to the amylolytic enzyme according to the invention from *Bacillus* sp. A 7-7 (DSM 12368). The protein according to the invention is clearly characterized as α-amylase through the homologous regions. Representative related proteins are presented in the alignment in FIG. 1.

On the basis of this alignment, largely the same secondary and tertiary structures may be assumed for proteins according to the invention as for the proteins used for homologizing. Their structural elements may be retrieved from generally accessible data banks such as, for example, the EMBL European Bioinformatics Institute (EBI) in Cambridge, UK, Swiss-Prot or GenBank (National Center for Biotechnology Information NCBI, National Institutes of Health, Bethesda, Md., USA). If differing structures should appear or if it should turn out that there are various folding variants with varying amylolytic properties, for example so far as the optimal reaction conditions or the substrate specificity is concerned, these are all included in the scope of protection of the present invention. This is because, firstly, the folding can depend upon the production conditions, for example in the presence or absence of the leader peptide. Secondly, these variants can turn out to be particularly suitable for various potential applications, for example for the quantitative liquefaction of starch, for the hydrolysis of cyclodextrins or for use in detergents/cleaners.

Particular interest attaches to the partial sequence corresponding to amino acids 32 to 516 from the sequence shown in SEQ ID NO. 2. This is because, as can be concluded from the amino acid sequence, the first 31 amino acids represent a signal peptide which, in the case of production in corresponding microorganisms, probably initiates the release of the protein from the cell interior into the medium surrounding the cells. After the release, this signal peptide is split off in vivo so that the actual amylolytic activity is developed by the remaining part of the protein.

Accordingly, for the actual amylolytic function, amino acids 1 to 31 are probably of little significance, but are of importance for production and particularly for the required folding. Because of this, they cannot be excluded from the scope of protection of the present invention.

Should it turn out that there are deviations in the length of the signal peptide and/or the mature protein during production, for example by one or other bacterial strain, the claims relating to positions 1 to 31 or 32 to 516 according to SEQ ID NO. 2 apply accordingly to the corresponding variants. For example, the transition of the protein from *Bacillus* sp. A 7-7 (DSM 12368) could use as many as six nucleotides before the nucleotide sequence shown in SEQ ID NO. 1. Before this probable beginning lie the six nucleotides ATG ACG. These could be translated as Met-Thr so that the signal peptide is N-terminally lengthened by two amino acids and a certain similarity to the amylase from *Bacillus* sp. # 707 shown in FIG. 1 under number 2 (SEQ ID NO: 3) is obtained. The splitting off the signal peptide also lends itself to variation.

Of the variants falling within the similarity range mentioned above, those which have optimized properties for the potential applications envisaged are particularly preferred. As explained at the beginning, such variants can be produced by methods, preferably molecular-biological methods, known per se. For example, it would also be possible to delete methionine, tryptophane, cysteine and/or tyrosine residues of proteins according to the invention and/or to replace them with less readily oxidizable amino acid residues in accordance with the teaching of WO 94/18314. Oxidation stability, the pH activity profile and/or thermal stability can be improved in this way. Further developments through point mutagenesis may also be carried, for example, in accordance with WO 99/09183 and WO 99/23211.

Fragments according to the invention are understood to be any proteins or peptides that are smaller than the proteins which correspond to those of SEQ ID NO. 1 or SEQ ID NO. 2, but are sufficiently homologous to them in the corresponding partial sequences. If they develop an amylolytic function or at least a function that supports the hydrolysis of an α-1, 4-glycosidic bond, they are regarded as amylolytically active fragments and represent embodiments of the present invention. This applies, for example, to fragments which contribute to the complexing of a substrate or to the formation of a structural element necessary for the hydrolysis. The fragments may be, for example, individual domains or fragments which do not accord with the domains. Such fragments can be produced relatively inexpensively, no longer have certain possibly unfavorable characteristics of the starting molecule, such as possibly an activity-reducing regulating mechanism, or may develop a more favorable activity profile. Such protein fragments can also be produced, for example, chemically rather than biosynthetically. Chemical synthesis can be advantageous, for example, when chemical modifications are to be made after the synthesis.

By virtue of their basic similarity, proteins obtainable by deletion mutation may also be assigned to the fragments. Such proteins may largely correspond biochemically to the starting molecules or no longer have individual functions. This appears particularly appropriate, for example, in the deletion of inhibiting regions. In the final analysis, the deletions may be used both for specialization and for extending the range of application of the protein. If an amylolytic function in the broadest sense is maintained, modified, specified or even achieved in the first place in this way, the deletion variants and the fragments are proteins according to the invention. The only additional requirement in this regard is that—over and above the homologous partial sequence still present—they should lie within the above-mentioned similarity range to the sequences SEQ ID NO. 1 and SEQ ID NO. 2.

For example, it is possible in accordance with WO 99/57250 to provide a protein according to the invention or parts thereof with binding domains from other proteins via peptidic or nonpeptidic linkers and thus to make hydrolysis of the substrate more effective. Such constructs fall within the scope of protection of the present invention when they develop amylolytic activities and those parts of the construct which perform this function are sufficiently similar to the stated sequences according to the invention. Equally, amylolytic proteins according to the invention may also be linked, for example, to proteases in order to perform a double function.

The proteins and signal peptides obtainable from preproteins by splitting off the N-terminal amino acids may also be regarded as naturally formed fragments or deletion-mutated proteins. A splitting mechanism such as this may also be used to predetermine specific cleavage sites in recombinant proteins with the aid of certain sequence regions that are recognized by signal peptidases. Proteins according to the invention can thus be activated and/or deactivated in vitro. The scope of protection of the present invention encompasses each of these proteins providing it falls within the claimed scope of protection and imparts amylolytic activity.

Chimeral or hybrid proteins according to the invention are understood to be proteins which are made up of elements emanating naturally from various polypeptide chains. This procedure is also known as shuffling or fusion mutagenesis. Proteins are chimeral proteins according to the invention when the proteins obtained by fusion have amylolytic activity in the broadest sense. This may be developed or modified by a part of the molecule which derives from a protein according to the invention and lies within the claimed similarity range. The object of such a fusion can be, for example, to produce or modify an amylolytic function or a function supporting the hydrolysis of α-1,4-glycosidic bonds with the aid of the fused-on part of the protein according to the invention. In the context of the invention, it does not matter whether such a chimeral protein consists of a single polypeptide chain or of several subunits among which various functions can be distributed. In order to realize the second alternative, it is possible, for example, to split a single chimeral polypeptide chain into several by controlled proteolytic cleavage either post-translationally or after a purification step. The present invention also relates to chimeral proteins which, by virtue of their construction, have an optionally lower identity over their entire amino acid and/or nucleotide sequence than defined above for the similarity range according to the invention, but may be assigned to it in at least one of the regions introduced by fusion and perform the same functions in this part as in an amylase which falls within the above-mentioned homology range over its entire length.

Proteins according to the invention obtainable by insertion mutation are variants of the proteins which fall over their entire sequence length into the designated range of protection of the SEQ ID NO. 1 or SEQ ID NO. 2 sequences and which have been obtained by insertion of a nucleic acid or protein fragment into the respective sequences. As with hybrid formation, the object of insertion mutagenesis can be to combine individual properties of proteins according to the invention with those of other proteins. Proteins are proteins according to the invention obtained by insertion mutation or chimeral proteins when the regions to be attributed through their homology to the SEQ ID NO. 1 or SEQ ID NO. 2 sequences have corresponding homology values and the protein has an amylolytic function in the broadest sense by virtue of those regions.

Accordingly, proteins obtained by inversion mutagenesis and those with a regrouping of various parts of the molecule which differs from the original amino acid sequence are included in the scope of protection of the present invention. It may be regarded as a deletion variant, an insertion variant or as a shuffling variant of the original protein.

Amylolytically active derivatives according to the invention are understood to be amylolytic proteins which have been modified, for example in connection with protein biosynthesis through processing by the host organism or chemically, for example by the transformation of a side chain of an amino acid or by covalent bonding of another compound to the protein. This compound may consist, for example, of other proteins which are bound to proteins according to the invention, for example by bifunctional chemical compounds. Such modifications can influence, for example, the substrate specificity or the strength of the bond to the substrate or can temporarily block the enzymatic activity where the coupled substance is an inhibitor. This may be appropriate, for example, for the duration of storage. Another embodiment are derivatives which have been obtained by covalent bonding to a macromolecular carrier such as, for example, polyethylene glycol or a polysaccharide.

Other solutions to the problem addressed by the invention are amylolytic proteins or derivatives which have at least one antigenic determinant in common with one of the above-mentioned proteins or derivatives.

This is because the development of enzymatic activities is critically determined not just by the pure amino acid sequence of a protein, but also by its secondary structural elements and its three-dimensional folding. Thus, domains differing clearly from one another in their primary structure can form spatially substantially corresponding structures and can thus provide for the same enzymatic behavior. Such common features in the secondary structure are normally recognized as corresponding antigenic determinants of antisera or pure or monoclonal antibodies. Structurally similar proteins or derivatives can therefore be detected and assigned through immunochemical cross reactions.

Accordingly, the scope of protection of the present invention also encompasses proteins or derivatives which have amylolytic activity and which can possibly be assigned to the above-defined proteins according to the invention or derivatives through their immunochemical relationship, but not through their homology values in the primary structure.

Proteins according to the invention which emanate from natural sources are preferred embodiments of the present invention, particularly where they originate from such microorganisms as single-cell fungi or bacteria. This is because such microorganisms are easier to handle than multicell organisms or cell cultures derived from them. These represent appropriate options for special embodiments.

Proteins or derivatives according to the invention from gram-positive bacteria are particularly preferred because they do not have an external membrane and therefore directly release secreted proteins into the surrounding medium.

Proteins or derivatives according to the invention from gram-positive bacteria of the genus *Bacillus* are most particularly preferred because they are established as production organisms with a particularly high production performance in industrial processes.

Of the proteins or derivatives according to the invention from *Bacillus* species, those from alcaliphilic *bacilli* are preferred, those from *Bacillus* sp. A 7-7 being particularly preferred and those from the strain *Bacillus* sp. A 7-7 (DSM 12368) most particularly preferred. This is because the embodiment of the enzyme according to the invention of which the associated sequences are shown in the sequence protocol and of which the enzymatic characteristics are described in the Examples was originally obtained from that strain.

Strains which release the amylolytic protein formed into the medium surrounding them are preferred for production reasons.

It is possible that, although naturally occurring producers can produce an amylolytic enzyme according to the invention, they only express it and/or release it into the surrounding medium to a minimal extent under the conditions initially determined. They still fall within the scope of protection of the present invention as long as it is possible experimentally to determine suitable environmental conditions or low molecular weight or other factors under whose influence they can be stimulated to produce the protein according to the invention on a level which makes economic utilization appear appropriate. A regulating mechanism such as this can be purposefully used for biotechnological production, for example for regulating the responsible promoters.

Depending on its isolation, working up or preparation, a protein can be associated with various other substances, particularly if it has been recovered from natural producers of the protein. Certain other substances may then—or even independently—have been purposefully added to it, for example to increase its stability in storage. Accordingly, the definition of the protein according to the invention also encompasses all preparations of the actual protein essential to the invention. This is also independent of whether or not it actually develops this enzymatic activity in a certain preparation because it can be desirable for the protein to have little or no activity in storage and only to develop its amylolytic activity at the time of use. This can depend, for example, on the folding status of the protein or can result from the reversible binding of one or more companion substances from the preparation or from another control mechanism.

Proteins according to the invention, particularly in storage, can be protected by stabilizers, for example against denaturing, disintegration or inactivation, for example by physical influences, oxidation or proteolytic cleavage. In the case of proteins obtained from microorganisms, inhibition of proteolysis is particularly critical because most microorganisms secrete various proteases as digestive enzymes into the surrounding media. Such enzymes can seriously damage the interesting proteins during the subsequent purification steps.

One group of stabilizers are reversible protease inhibitors such as, for example, benzamidine hydrochloride and leupeptin, borax, boric acids, boron acids, salts or esters thereof, peptide aldehydes or pure peptidic inhibitors, such as ovomucoid or specific subtilisin inhibitors. Other common enzyme stabilizers are aminoalcohols, such as mono-, di-, tri-ethanolamine and -propanolamine, aliphatic carboxylic acids up to $C_{12}$, dicarboxylic acids, lower aliphatic alcohols, but above all polyols such as, for example, glycerol, ethylene glycol, propylene glycol or sorbitol. Calcium salts such as, for example, calcium acetate or calcium formate, magnesium salts, various polymers, such as for example lignin, cellulose ethers, polyamides or water-soluble vinyl copolymers, are also used to stabilize the enzyme preparation, above all against physical influences or pH variations. Reducing agents and antioxidants, such as sodium sulfite or reducing sugars for example, increase the stability of the proteins against oxidative disintegration.

The present invention is also embodied in corresponding nucleic acids providing the nucleic acids in question code for an amylolytic protein in the broadest sense and show sufficient similarity—as defined above—to the SEQ ID NO. 1 sequence, more particularly in nucleic acids which code for a protein that corresponds to the partial range of amino acids 32 to 516 of the amino acid sequence shown in SEQ ID NO. 1.

Particularly preferred embodiments are nucleic acids which code for one of the above-described amylolytic proteins according to the invention. This also includes variants which do not fall within the similarity range defined in SEQ ID NO. 1 over their entire sequence length, but do so in individual regions. These include, for example, the nucleotide sequences which, as explained above, have been obtained by insertion or deletion mutation, chimeral proteins or protein fragments. However, so-called antisense constructs, for example through individual partial sections, also represent embodiments of the present invention because they can be used to regulate the amylolytic activity.

Nucleic acids form the starting point for molecular-biological investigations and further developments. Such methods are described, for example, in the manual by Fritsch, Sambrook and Maniatis "Molecular cloning: a laboratory manual", Cold Spring Harbour Laboratory Press, New York, 1989. All the genetic engineering and protein-biochemical methods which come under the heading of protein engineering in the prior art are also based on the gene, particularly the cloned gene. Proteins according to the invention can be further optimized for various uses by such methods, for example by point mutagenesis or by fusion with sequences from other genes.

The variants according to the invention of a protein obtainable by molecular-biological methods known per se include in particular those with individual, specific amino acid exchanges or randomized point mutations, deletions of individual amino acids or of partial sequences, fusions with other fragments or other enzymes, insertions or inversions, i.e. partial sequence inversions. Such mutations or modifications can represent preferred embodiments for specific applications. Such a mutagenesis can be carried out purposefully or by random methods. It can be combined, for example, with a subsequent activity-directed screening and selection process on the cloned genes. The genes obtained by mutation fall within the scope of protection of the present invention providing they code for amylolytic proteins in the broadest sense and fall within the similarity range defined above, at least in the homologous and functionally relevant regions.

Another solution to the problem addressed by the invention and hence another embodiment of the invention are the organisms which naturally form a protein according to the invention or derivative or contain nucleic acids which code for a protein according to the invention or derivative. This is because their discovery enables the inventive concept to be put into practice. Such organisms are obtainable by generally known techniques, for example by isolating strains from a natural habitat or by screening of gene banks. The nucleotide sequence shown in SEQ ID NO. 1 may be used, for example, as a screening probe or as an original for the construction of corresponding PCR primers. Analogously, short-chain or complete peptides with amino acid sequences according to SEQ ID NO. 2 may be used to form corresponding antisera with which corresponding organisms or the proteins released from them can be identified.

In accordance with the foregoing observations, microorganisms, preferably bacteria, especially gram-positive bacteria including those of the genus Bacillus, more particularly Bacillus sp. A 7-7 and most particularly Bacillus sp. A 7-7 (DSM 12368), are preferred above all by virtue of their cultivatability.

Another embodiment of the invention are vectors which contain one of the nucleic acid regions of the second embodiment.

This is because, to use nucleic acids, the DNA is suitably cloned in a vector. Such vectors include, for example, those which are derived from bacterial plasmids, from viruses or from bacteriophages or predominantly synthetic vectors or plasmids with elements of various origins. With the other genetic elements present, vectors are able to establish themselves as stable units in the respective host cells over several generations. In the context of the invention, it does not matter whether they establish themselves extrachromosomally as independent units or are integrated into a chromosome. Which of the many systems known from the prior art is selected will depend upon the particular individual case. Critical factors in this regard include, for example, the number of copies which can be made, the selection systems available, including above all resistances to antibiotics, and the cultivatability of the host cells capable of accommodating the vectors.

The vectors form suitable starting points for molecular-biological and biochemical investigations of the particular gene or associated protein and for further developments according to the invention and ultimately for the amplification and production of proteins according to the invention. They represent embodiments of the present invention insofar as the sequences of the nucleic acid regions according to the invention present lie within the homology range defined in detail in the foregoing.

Preferred embodiments of the present invention are cloning vectors. Besides storage, biological amplification and selection of the interesting gene, cloning vectors are suitable for the characterization of the particular gene, for example through the drawing up of a restriction map or sequencing. Cloning vectors are also preferred embodiments of the present invention because they represent a transportable and storable form of the claimed DNA. They are also preferred starting points for molecular-biological techniques which are not restricted to cells, such as the polymerase chain reaction for example.

Expression vectors have partial sequences which are capable of replicating in the host organisms optimized for the production of proteins and of expressing the gene present in the host organism. Preferred embodiments are expression vectors which themselves carry the genetic elements necessary for expression. Expression is influenced, for example, by promoters which regulate the transcription of the gene. Thus, expression can take place through the natural promoter originally located before the gene and also after genetically engineered fusion both through a promoter of the host cell provided on the expression vector and also through a modified promoter or a totally different promoter of another organism.

Preferred embodiments of the invention are expression vectors which can be regulated through changes in the culture conditions or by addition of certain compounds, such as for example the cell density or special factors. Expression vectors enable the associated protein to be heterologously produced, i.e. in an organism other than that from which it can naturally be obtained. Homologous protein production from a host organism naturally expressing the gene via a suitable vector also lies within the scope of protection of the present invention. This can have the advantage that natural modification reactions associated with the translation can be carried out as well on the protein formed as they would take place naturally.

Other embodiments of the present invention can be cell-free expression enzymes where protein biosynthesis is completed in vitro. Expression systems such as these are also established in the prior art.

Another embodiment of the present invention are cells which contain one of the above-defined vectors, more particularly a cloning or expression vector. This is because, in the course of molecular-biological works as required, for example, for mutagenesis, sequencing or storage of the vectors, they are transformed into corresponding cells. Depending on the method, gram-positive bacteria for example, but especially gram-negative bacteria, can be suitable for this purpose.

Another embodiment are host cells which express a protein or derivative of the first embodiment or can be stimulated to express that protein or derivative, preferably using an expression vector of the type defined above.

This is because the preferred in vivo synthesis of an amylolytic enzyme according to the invention requires the transfer of the associated gene into a host cell. Suitable host cells are, in principle, any organisms, i.e. prokaryotes, eukaryotes or cyanophyta. Preferred host cells are those which are easy to handle genetically, for example as far as transformation with the expression vector and its stable establishment are concerned, for example single-cell fungi or bacteria. In addition, preferred host cells are distinguished by easy microbiological and biotechnological handling. This includes, for example, easy cultivation, high growth rates, minimal fermentation media requirements and good production and secretion rates for foreign proteins. The optimal expression systems for the particular individual case often have to be experimentally determined from the large number of different systems available in the prior art. In this way, each protein according to the invention can be obtained from a large number of host organisms.

Preferred embodiments are host cells which can be regulated in their activity through genetic regulation elements which are available, for example, on the expression vector but which can also be present from the outset in these cells. The host cells in question can be stimulated to express, for example by controlled addition of chemical compounds serving as activators, by changing the cultivation conditions or on reaching a certain cell density. This provides for very economical production of the interesting proteins.

A variant of this experimental principle are expression systems where additional genes, for example those made available on other vectors, influence the production of proteins according to the invention. They may be modifying gene products or those which are to be purified together with the protein according to the invention, for example to influence its amylolytic function. These may be, for example, other proteins or enzymes, inhibitors or elements which influence the interaction with various substrates.

Preferred host cells are prokaryotic or bacterial cells. Bacteria are generally distinguished from eucaryotes by shorter generation times and less demanding cultivation conditions. Inexpensive processes for the production of proteins according to the invention can thus be established.

Host cells and particularly bacteria which secrete the protein or derivative formed into the surrounding medium, so that the expressed proteins according to the invention can be directly purified, are particularly preferred.

One embodiment of the present invention uses *Bacillus* sp. A 7-7 (DSM 12368) itself for homologously expressing proteins according to the invention. This can be done, for example, via an introduced vector which introduces the already endogenously present gene or modifications thereof according to the invention into these cells, for example in a multiple number of copies. This can be particularly advantageous if, after its synthesis, the protein is to be subjected to modifications which are suitably carried out by the cells in question themselves.

By contrast, heterologous expression is preferred. Gram-positive bacteria, such as actinomycetes or *bacilli* for example, have no outer membrane so that they release secreted proteins directly into the medium surrounding them. Accordingly, bacteria preferred for heterologous expression include those of the genus *Bacillus*, more particularly those of the species *Bacillus licheniformis, Bacillus amyloliquefaciens, Bacillus subtilis* or *Bacillus alcalophilus*.

Gram-negative bacteria may also be used for heterologous expression. In their case, a large number of proteins are secreted into the periplasmatic space, i.e. into the compartment between the two membranes surrounding the cells. This can be advantageous for special applications. Gram-negative bacteria include, for example, those of the genus *Klebsiella* or

*Escherichia*, preferably the species *Escherichia coil* and more preferably the strains *E. coli* JM 109, *E. coli* DH 100B or *E. coli* DH 12S.

Eukaryotic cells are also suitable for the production of amylolytic proteins according to the invention. Examples include yeasts, such as *Saccharomyces* or *Kluyveromyces*. This can be particularly advantageous, for example, when the proteins are to be subjected in connection with their synthesis to modifications which such systems allow. These include, for example, the binding of low molecular weight compounds, such as membrane anchors or oligosaccharides.

All the elements discussed above may be combined into processes for producing proteins according to the invention. For each protein according to the invention, there are a number of possible combinations of process steps. They are all practical embodiments of the idea on which the present invention is based, namely quantitatively producing representatives of a protein type—defined through the amylolytic function and, at the same time, through the high homology to the sequences shown in the sequence protocols—with the aid of the associated genetic information. The optimal process has to be experimentally determined for each actual individual case.

In principle, the following procedure is adopted: nucleic acids according to the invention, i.e. those which fall within the above-defined similarity range to the SEQ ID NO. 1 sequence, are suitably ligated in the form of the DNA in a suitable expression vector. This is transformed into the host cell, for example into cells of an easy-to-cultivate bacterial strain, which releases the proteins, of which the genes are under the control of corresponding genetic elements, into the surrounding nutrient medium; regulating elements for this can be made available, for example, by the expression vector. The protein according to the invention can be purified from the surrounding medium by several purification steps such as, for example, precipitation or chromatography. The expert is able to scale up a system that has been experimentally optimized in the laboratory to industrial-scale production.

The most important industrial applications for proteins according to the invention are listed in the following. Many established industrial applications for amylolytic enzymes are described in manuals, such as for example the book by H. Uhlig entitled "Industrial enzymes and their applications", Wiley, New York, 1998. The following list is by no means complete and merely represents a selection of the many theoretically possible applications. If it should turn out that individual proteins according to the invention are suitable for additional applications not expressly claimed herein, those applications are hereby included in the scope of protection of the present invention.

An important application for amylolytic enzymes is their use as active components in detergents/cleaners for cleaning textiles or hard surfaces. In such applications, the amylolytic activity is used for hydrolytically dissolving carbohydrate-containing, more especially starch-like, soils and/or removing them from the substrate. To this end, the enzymes may be used on their own, in suitable media or even in detergents/cleaners. These compositions are distinguished by the fact that the amylolytic enzymes and the other components synergistically effect the elimination of the soils, for example by the hydrolysis products of the amylolytic proteins being solubilized by other ingredients of the compositions, such as surfactants for example. A protein according to the invention can be used both in compositions for institutional or industrial users and in products for the domestic consumer.

Accordingly, another embodiment of the invention are any detergents/cleaners which are characterized in that they contain an amylolytic protein according to the invention or derivative thereof.

By this is meant all possible types of cleaning compositions, both concentrates and compositions to be used without dilution; for use on a commercial scale, in washing machines or in hand washing or cleaning. Such compositions include, for example, detergents for textiles, carpets or natural fibers for which the term detergent is used in the present specification. They also include, for example detergents for dishwashers or manual dishwashing or cleaners for hard surfaces, such as metals, glass china, ceramic, tiles, stone, painted surfaces, plastics, wood or leather; for these, the term cleaner is used in the present specification. Any type of cleaning composition represents an embodiment of the present invention providing it is enriched by a protein according to the invention.

Embodiments of the present invention encompass all supply forms of the compositions according to the invention established in the prior art and/or all appropriate supply forms of the compositions according to the invention. These include, for example, solid, powder-form, liquid, gel-form or paste-form compositions, optionally consisting of several phases, compressed or non-compressed. The supply forms also include extrudates, granules, tablets and pouches packed both in large containers and in portions.

Besides an enzyme essential to the invention, the composition according to the invention optionally contains other ingredients, such as surfactants, for example nonionic, anionic and/or amphoteric surfactants, and/or bleaching agents and/or builders and optionally other typical ingredients.

Preferred nonionic surfactants are alkoxylated, advantageously ethoxylated, more particularly primary alcohols preferably containing 8 to 18 carbon atoms and an average of 1 to 12 mmol ethylene oxide (EO) per mol alcohol, in which the alcohol residue may be linear or, preferably, 2-methyl-branched or may contain linear and methyl-branched residues in the form of the mixtures typically present in oxoalcohol residues. However, alcohol ethoxylates containing linear residues of alcohols of native origin with 12 to 18 carbon atoms, for example coconut oil alcohol, palm oil alcohol, tallow alcohol or oleyl alcohol, and an average of 2 to 8 EO per mol alcohol are particularly preferred. Preferred ethoxylated alcohols include, for example, $C_{12-14}$ alcohols containing 3 EO or 4 EO, $C_{9-11}$ alcohol containing 7 EO, $C_{13-15}$ alcohols containing 3 EO, 5 EO, 7 EO or 8 EO, $C_{12-18}$ alcohols containing 3 EO, 5 EO or 7 EO and mixtures thereof, such as mixtures of $C_{12-14}$ alcohol containing 3 EO and $C_{12-18}$ alcohol containing 5 EO. The degrees of ethoxylation mentioned are statistical mean values which, for a special product, may be either a whole number or a broken number. Preferred alcohol ethoxylates have a narrow homolog distribution (narrow range ethoxylates, NRE). In addition to these nonionic surfactants, fatty alcohols containing more than 12 EO may also be used. Examples of such fatty alcohols are tallow alcohols containing 14 EO, 25 EO, 30 EO or 40 EO.

Another class of preferred nonionic surfactants which are used either as sole nonionic surfactant or in combination with other nonionic surfactants are alkoxylated, preferably ethoxylated or ethoxylated and propoxylated, fatty acid alkyl esters preferably containing 1 to 4 carbon atoms in the alkyl chain, more particularly fatty acid methyl esters.

Another class of nonionic surfactants which may be used with advantage are the alkyl polyglycosides (APGs). Suitable alkyl polyglycosides correspond to the general formula $RO(G)_z$ where R is a linear or branched, more particularly 2-methyl-branched, saturated or unsaturated aliphatic radical containing 8 to 22 and preferably 12 to 18 carbon atoms, G is a glycose unit containing 5 or 6 carbon atoms, preferably glucose. The degree of glycosidation z is between 1.0 and 4.0, preferably between 1.0 and 2.0 and more preferably between 1.1 and 1.4. Linear alkyl polyglucosides, i.e. alkyl polyglycosides in which the polyglycosyl moiety is a glucose unit and the alkyl moiety is an n-alkyl group, are preferably used.

Nonionic surfactants of the amine oxide type, for example N-cocoalkyl-N,N-dimethylamine oxide and N-tallowalkyl-N,N-dihydroxyethyl amine oxide, and the fatty acid alkanolamide type are also suitable. The quantity in which these nonionic surfactants are used is preferably no more, in particular no more than half, the quantity of ethoxylated fatty alcohols used.

Other suitable surfactants are polyhydroxyfatty acid amides corresponding to formula (II):

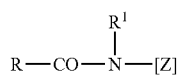

(II)

in which RCO is an aliphatic acyl radical containing 6 to 22 carbon atoms, $R^1$ is hydrogen, an alkyl or hydroxyalkyl radical containing 1 to 4 carbon atoms and [Z] is a linear or branched polyhydroxyalkyl radical containing 3 to 10 carbon atoms and 3 to 10 hydroxyl groups. The polyhydroxyfatty acid amides are known substances which may normally be obtained by reductive amination of a reducing sugar with ammonia, an alkylamine or an alkanolamine and subsequent acylation with a fatty acid, a fatty acid alkyl ester or a fatty acid chloride.

The group of polyhydroxyfatty acid amides also includes compounds corresponding to formula (III):

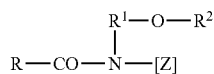

(II)

in which R is a linear or branched alkyl or alkenyl group containing 7 to 12 carbon atoms, $R^1$ is a linear, branched or cyclic alkyl group or an aryl group containing 2 to 8 carbon atoms and $R^2$ is a linear, branched or cyclic alkyl group or an aryl group or an oxyalkyl group containing 1 to 8 carbon atoms, $C_{1-4}$ alkyl or phenyl groups being preferred, and [Z] is a linear polyhydroxyalkyl group, of which the alkyl chain is substituted by at least two hydroxyl groups, or alkoxylated, preferably ethoxylated or propoxylated, derivatives of that group.

[Z] is preferably obtained by reductive amination of a reduced sugar, for example glucose, fructose, maltose, lactose, galactose, mannose or xylose. The N-alkoxy- or N-aryloxy-substituted compounds may then be converted into the required polyhydroxyfatty acid amides by, for example, reaction with fatty acid methyl esters in the presence of an alkoxide as catalyst.

Suitable anionic surfactants are, for example, those of the sulfonate and sulfate type. Suitable surfactants of the sulfonate type are preferably $C_{9-13}$ alkyl benzenesulfonates, olefin sulfonates, i.e. mixtures of alkene and hydroxy-alkane sulfonates, and the disulfonates obtained, for example, from $C_{12-18}$ monoolefins with an internal or terminal double bond by sulfonation with gaseous sulfur trioxide and subsequent alkaline or acidic hydrolysis of the sulfonation products. Other suitable surfactants of the sulfonate type are the alkane sulfonates obtained from $C_{12-18}$ alkanes, for example by sulfochlorination or sulfoxidation and subsequent hydrolysis or neutralization. The esters of α-sulfofatty acids (ester sulfonates), for example the α-sulfonated methyl esters of hydrogenated coconut oil, palm kernel oil or tallow fatty acids, are also suitable.

Other suitable anionic surfactants are sulfonated fatty acid glycerol esters. Fatty acid glycerol esters in the context of the present invention are the monoesters, diesters and triesters and mixtures thereof which are obtained where production is carried out by esterification of a monoglycerol with 1 to 3 mol fatty acid or in the transesterification of triglycerides with 0.3 to 2 mol glycerol. Preferred sulfonated fatty acid glycerol esters are the sulfonation products of saturated fatty acids containing 6 to 22 carbon atoms, for example caproic acid, caprylic acid, capric acid, myristic acid, lauric acid, palmitic acid, stearic acid or behenic acid.

Preferred alk(en)yl sulfates are the alkali metal salts and, in particular, the sodium salts of the sulfuric acid semiesters of $C_{12-18}$ fatty alcohols, for example cocofatty alcohol, tallow fatty alcohol, lauryl, myristyl, cetyl or stearyl alcohol, or $C_{10-20}$ oxoalcohols and the corresponding semiesters of secondary alcohols with the same chain length. Other preferred alk(en)yl sulfates are those with the chain length mentioned which contain a synthetic, linear alkyl chain based on a petrochemical and which are similar in their degradation behavior to the corresponding compounds based on oleochemical raw materials. $C_{12-16}$ alkyl sulfates, $C_{12-15}$ alkyl sulfates and $C_{14-15}$ alkyl sulfates are preferred from the point of view of washing technology. Other suitable anionic surfactants are 2,3-alkyl sulfates.

The sulfuric acid monoesters of linear or branched $C_{7-21}$ alcohols ethoxylated with 1 to 6 mol ethylene oxide, such as 2-methyl-branched $C_{9-11}$ alcohols containing on average 3.5 mol ethylene oxide (EO) or $C_{12-18}$ fatty alcohols containing 1 to 4 EO, are also suitable. In view of their high foaming capacity, they are only used in relatively small quantities, for example in quantities of 1 to 5% by weight, in cleaners.

Other suitable anionic surfactants are the salts of alkyl sulfosuccinic acid which are also known as sultosuccinates or as sulfosuccinic acid esters and which represent monoesters and/or diesters of sulfosuccinic acid with alcohols, preferably fatty alcohols and, more particularly, ethoxylated fatty alcohols. Preferred sulfosuccinates contain $C_{8-18}$ fatty alcohol residues or mixtures thereof. Particularly preferred sulfosuccinates contain a fatty alcohol moiety derived from ethoxylated fatty alcohols which, considered in isolation, represent nonionic surfactants (for a description, see below). Of these sulfosuccinates, those of which the fatty alcohol moieties are derived from narrow-range ethoxylated fatty alcohols are particularly preferred. Alk(en)yl succinic acid preferably containing 8 to 18 carbon atoms in the alk(en)yl chain or salts thereof may also be used.

Other suitable anionic surfactants are, in particular, soaps. Suitable soaps are saturated fatty acid soaps, such as the salts of lauric acid, myristic acid, palmitic acid, stearic acid, hydrogenated erucic acid and behenic acid, and soap mixtures derived in particular from natural fatty acids, for example coconut oil, palm kernel oil or tallow fatty acids.

The anionic surfactants, including the soaps, may be present in the form of their sodium, potassium or ammonium salts and as soluble salts of organic bases, such as mono-, di- or triethanolamine. The anionic surfactants are preferably present in the form of their sodium or potassium salts and, more preferably, in the form of their sodium salts.

The surfactants may be present in the detergents according to the invention in a total quantity of preferably 5% by weight to 50% by weight and more particularly 8% by weight to 30% by weight, based on the final detergent.

Bleaching agents may be present in accordance with the invention. Among the compounds yielding $H_2O_2$ in water which serve as bleaching agents, sodium percarbonate, sodium perborate tetrahydrate and sodium perborate monohydrate and are particularly important. Other useful bleaching agents are, for example, peroxypyrophosphates, citrate perhydrates and $H_2O_2$-yielding peracidic salts or peracids, such as persulfates or persulfuric acid. The urea peroxohydrate percarbamide, which may be described by the formula $H_2N$—$CO$—$NH_2.H_2O_2$, may also be used. If desired, the compositions may also contain bleaching agents from the group of organic bleaches, particularly where they are used for cleaning hard surfaces, for example in dishwashing machines, although in principle organic bleaches may also be used in laundry detergents. Typical organic bleaching agents are diacyl peroxides, such as dibenzoyl peroxide for example. Other typical organic bleaching agents are the peroxy acids, of which alkyl peroxy acids and aryl peroxy acids are particularly mentioned as examples. Preferred representatives are peroxybenzoic acid and ring-substituted derivatives thereof, such as alkyl peroxybenzoic acids, but also peroxy-α-naphthoic acid and magnesium monoperphthalate, aliphatic or substituted aliphatic peroxy acids, such as peroxylauric acid, peroxystearic acid, ε-phthalimidoperoxycaproic acid [phthaloiminoperoxyhexanoic acid (PAP)], o-carboxybenzamidoperoxycaproic acid, N-nonenylamidoperadipic acid and N-nonenylamidopersuccinates and aliphatic and araliphatic peroxydicarboxylic acids, such as 1,12-diperoxycarboxylic acid, 1,9-diperoxyazelaic acid, diperoxysebacic acid, diperoxybrassylic acid, diperoxyphthalic acids, 2-decyldiperoxybutane-1,4-dioic acid, N,N-terephthaloyl-di(6-aminopercaproic acid).

The content of bleaching agents can be from 1 to 40% by weight and, in a particular embodiment, is from 10 to 20% by weight, perborate monohydrate or percarbonate advantageously being used. A synergistic use of amylase with percarbonate or amylase with percarboxylic acid is disclosed in WO 99/63036 and WO 99/63037.

In order to obtain an improved bleaching effect where washing is carried out at temperatures of 60° C. or lower and particularly in the pretreatment of laundry, the compositions may also contain bleach activators. Suitable bleach activators are compounds which form aliphatic peroxocarboxylic acids containing preferably 1 to 10 carbon atoms and more preferably 2 to 4 carbon atoms and/or optionally substituted perbenzoic acid under perhydrolysis conditions. Substances bearing O- and/or N-acyl groups with the number of carbon atoms mentioned and/or optionally substituted benzoyl groups are suitable. Preferred bleach activators are polyacylated alkylenediamines, more particularly tetraacetyl ethylenediamine (TAED), acylated triazine derivatives, more particularly 1,5-diacetyl-2,4-dioxohexa-hydro-1,3,5-triazine (DADHT), acylated glycolurils, more particularly 1,3,4,6-tetraacetyl glycoluril (TAGU), N-acylimides, more particularly N-nonanoyl succinimide (NOSI), acylated phenol sulfonates, more particularly n-nonanoyl or isononanoyloxybenzenesulfonate (n- or iso-NOBS), acylated hydrocarboxylic acids, such as triethyl-O-acetyl citrate (TEOC), carboxylic anhydrides, more particularly phthalic anhydride, isatoic anhydride and/or succinic anhydride, carboxylic acid amides, such as N-methyl diacetamide, glycolide, acylated polyhydric alcohols, more particularly triacetin, ethylene glycol diacetate, isopropenyl acetate, 2,5-diacetoxy-2,5-dihydrofuran and the enol esters known from German patent applications DE 196 16 693 and DE 196 16 767, acetylated sorbitol and mannitol and the mixtures thereof (SORMAN) described in European patent application EP 0 525 239, acylated sugar derivatives, more particularly pentaacetyl glucose (PAG), pentaacetyl fructose, tetraacetyl xylose and octaacetyl lactose, and acetylated, optionally N-alkylated glucamine and gluconolactone, triazole or triazole derivatives and/or particulate caprolactams and/or caprolactam derivatives, preferably N-acylated lactams, for example N-benzoyl caprolactam and N-acetyl caprolactam, which are known from International patent applications WO-A-94/27970, WO-A-94/28102, WO-A-94/28103, WO-A-95/00626, WO-A-95/14759 and WO-A-95/17498. The substituted hydrophilic acyl acetals known from German patent application DE-A-196 16 769 and the acyl lactams described in German patent application DE-A-196 16 770 and in International patent application WO-A-95/14075 are also preferably used. The combinations of conventional bleach activators known from German patent application DE-A-44 43 177 may also be used. Nitrile derivatives, such as cyanopyridines, nitrile quats, for example N-alkyl ammonium acetonitriles, and/or cyanamide derivatives may also be used. Preferred bleach activators are sodium-4-(octanoyloxy)-benzene sulfonate, n-nonanoyl or isononanoyloxybenzenesulfonate (n- or iso-NOBS), undecenoyloxybenzenesulfonate (UDOBS), sodium dodecanoyloxybenzenesulfonate (DOBS), decanoyloxybenzoic acid (DOBA, OBC 10) and/or dodecanoyloxybenzenesulfonate (OBS 12) and N-methyl morpholiium acetonitrile (MMA). Bleach activators such as these are present in the usual quantities of 0.01 to 20% by weight, preferably in quantities of 0.1% by weight to 15% by weight and more preferably in quantities of 1% by weight to 10% by weight, based on the composition as a whole.

In addition to or instead of the conventional bleach activators mentioned above, so-called bleach catalysts may also be incorporated. Bleach catalysts are bleach-boosting transition metal salts or transition metal complexes such as, for example, manganese-, iron-, cobalt-, ruthenium- or molybdenum-salen complexes or carbonyl complexes. Manganese, iron, cobalt, ruthenium, molybdenum, titanium, vanadium and copper complexes with nitrogen-containing tripod ligands and cobalt-, iron-, copper- and ruthenium-ammine complexes may also be used as bleach catalysts, the compounds described in DE 197 09 284 A1 preferably being used. According to WO 99/63038, acetonitrile derivatives and, according to WO 99/63041, bleach-activating transition metal compounds are also capable of developing a bleach-activating effect in combination with amylases.

Compositions according to the invention generally contain one or more builders, more particularly zeolites, silicates, carbonates, organic co-builders and—providing there are no objections to their use on ecological grounds—the phosphates. Phosphates are particularly preferred builders in dishwasher detergents.

Suitable crystalline layered sodium silicates correspond to the general formula $NaMSi_xO_{2x+1} \cdot y H_2O$, where M is sodium or hydrogen, x is a number of 1.6 to 4 and y is a number of 0 to 20, preferred values for x being 2, 3 or 4. Crystalline layered silicates such as these are described, for example, in European patent application EP-A-0 164 514. Preferred crystalline layered silicates corresponding to the above formula are those in which M is sodium and x assumes the value 2 or 3. Both β- and δ-sodium disilicates $Na_2Si_2O_5 \cdot y H_2O$ are particularly preferred. Such compounds are commercially available, for example, as SKS® (Clariant). Thus SKS-6® is mainly a δ-sodium disilicate with the formula $Na_2Si_2O_5.yH_2O$ while SKS-7® is mainly the β-sodium disilicate. By reaction with acids (for example citric acid or carbonic acid), the δ-sodium disilicate gives kanemite $NaHSi_2O_5.H_2O$ which is marketed as SKS-9® and SKS-10® (Clariant). It can also be of advantage to use chemical modifications of these layered silicates. For example, the alkalinity of the layered silicates can be suitably influenced. Compared with the δ-sodium disilicate, phosphate- or carbonate-doped layered silicates have modified crystal morphologies, dissolve more quickly and show increased an calcium binding capacity in relation to δ-sodium disilicate. Layered silicates with the general empirical formula $x\ Na_2O.y\ H_2O.z\ P_2O_5$, in which the ratio of x to y corresponds to a number of 0.35 to 0.6, the ratio of x to z corresponds to a number of 1.75 to 1200 and the ratio of y to z corresponds to a number of 4 to 2,800, are described in patent application DE 19601063. The solubility of the layered silicates can also be increased by using particularly fine-particle layered silicates. Compounds of the crystalline layered silicates with other ingredients may also be used. Particular mention is made of compounds with cellulose derivatives, which have advantages in the disintegrating effect and are used in particular in detergent tablets, and compounds with polycarboxylates, for example citric acid, or polymeric polycarboxylates, for example copolymers of acrylic acid.

Other useful builders are amorphous sodium silicates with a modulus ($Na_2O:SiO_2$ ratio) of 1:2 to 1:3.3, preferably 1:2 to 1:2.8 and more preferably 1:2 to 1:2.6 which dissolve with delay and exhibit multiple wash cycle properties. The delay in dissolution in relation to conventional amorphous sodium silicates can have been obtained in various ways, for example by surface treatment, compounding/compacting or by overdrying. In the context of the invention, the term "amorphous" is also understood to encompass "X-ray amorphous". In other words, the silicates do not produce any of the sharp X-ray reflexes typical of crystalline substances in X-ray diffraction experiments, but at best one or more maxima of the scattered X-radiation which have a width of several degrees of the diffraction angle. However, particularly good builder properties may even be achieved where the silicate particles produce crooked or even sharp diffraction maxima in electron diffraction experiments. This may be interpreted to mean that the products have microcrystalline regions between 10 and a few hundred nm in size, values of up to at most 50 nm and, more particularly, up to at most 20 nm being preferred. Compacted amorphous silicates, compounded amorphous silicates and overdried X-ray-amorphous silicates are particularly preferred.

The finely crystalline, synthetic zeolite containing bound water used in accordance with the invention is preferably zeolite A and/or zeolite P. Zeolite MAP® (Crosfield) is a particularly preferred P-type zeolite. However, zeolite X and mixtures of A, X and/or P are also suitable. According to the invention, it is preferred to use, for example, a commercially obtainable co-crystallizate of zeolite X and zeolite A (ca. 80% by weight zeolite X) which is marketed by CONDEA Augusta S.p.A. under the name of VEGOBOND AX® and which may be described by the following formula:

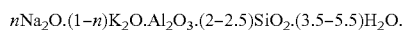

$nNa_2O.(1-n)K_2O.Al_2O_3.(2-2.5)SiO_2.(3.5-5.5)H_2O.$

Suitable zeolites have a moan particle size of less than 10 μm (volume distribution, as measured by the Coulter Counter Method) and contain preferably 18 to 22% by weight and more preferably 20 to 22% by weight of bound water.

The generally known phosphates may of course also be used as builders providing their use should not be avoided on ecological grounds. Among the large number of commercially available phosphates, alkali metal phosphates have the greatest importance in the detergent industry, pentasodium triphosphate and pentapotassium triphosphate (sodium and potassium tripolyphosphate) being particularly preferred.

"Alkali metal phosphates" is the collective term for the alkali metal (more particularly sodium and potassium) salts of the various phosphoric acids, including metaphosphoric acids $(HPO_3)_n$ and orthophosphoric acid $(H_3PO_4)$ and representatives of higher molecular weight. The phosphates combine several advantages: they act as alkalinity sources, prevent lime deposits on machine parts and lime incrustations in fabrics and, in addition, contribute towards the cleaning effect.

Sodium dihydrogen phosphate $(NaH_2PO_4)$ exists as the dihydrate (density 1.91 $gcm^{-3}$, melting point 60°) and as the monohydrate (density 2.04 $gcm^{-3}$). Both salts are white readily water-soluble powders which, on heating, lose the water of crystallization and, at 200° C., are converted into the weakly acidic diphosphate (disodium hydrogen diphosphate, $Na_2H_2P_2O_7$) and, at higher temperatures, into sodium trimetaphosphate $(Na_3P_3O_9)$ and Maddrell's salt (see below). $NaH_2PO_4$ shows an acidic reaction. It is formed by adjusting phosphoric acid with sodium hydroxide to a pH value of 4.5 and spraying the resulting "mash". Potassium dihydrogen phosphate (primary or monobasic potassium phosphate, potassium biphosphate, KDP), $KH_2PO_4$, is a white salt with a density of 2.33 $gcm^{-3}$, has a melting point of 253° [decomposition with formation of potassium polyphosphate $(KPO_3)_x$] and is readily soluble in water.

Disodium hydrogen phosphate (secondary sodium phosphate), $Na_2HPO_4$, is a colorless, readily water-soluble crystalline salt. It exists in water-free form and with 2 mol (density 2.066 $gcm^{-3}$, water loss at 95°), 7 mol (density 1.68 $gcm^{-3}$, melting point 48° with loss of $5H_2O$) and 12 mol of water (density 1.52 $gcm^{-3}$, melting point 35° with loss of $5H_2O$), becomes water-free at 100° and, on fairly intensive heating, is converted into the diphosphate $Na_4P_2O_7$. Disodium hydrogen phosphate is prepared by neutralization of phosphoric acid with soda solution using phenolphthalein as indicator. Dipotassium hydrogen phosphate (secondary or dibasic potassium phosphate), $K_2HPO_4$, is an amorphous white salt which is readily soluble in water.

Trisodium phosphate, tertiary sodium phosphate, $Na_3PO_4$, consists of colorless crystals which have a density of 1.62 $gcm^{-3}$ and a melting point of 73-76° C. (decomposition) as the dodecahydrate, a melting point of 100° C. as the decahydrate (corresponding to 19-20% $P_2O_5$) and a density of 2.536 $gcm^{-3}$ in water-free form (corresponding to 39-40% $P_2O_5$). Trisodium phosphate is readily soluble in water through an alkaline reaction and is prepared by concentrating a solution of exactly 1 mole of disodium phosphate and 1 mole of NaOH by evaporation. Tripotassium phosphate (tertiary or tribasic potassium phosphate), $K_3PO_4$, is a white deliquescent granular powder with a density of 2.56 $gcm^{-3}$, has a melting point of 1340° and is readily soluble in water through an alkaline reaction. It is formed, for example, when Thomas slag is heated with coal and potassium sulfate. Despite their higher price, the more readily soluble and therefore highly effective potassium phosphates are often preferred to corresponding sodium compounds in the detergent industry.

Tetrasodium diphosphate (sodium pyrophosphate), $Na_4P_2O_7$, exists in water-free form (density 2.534 $gcm^{-3}$, melting point 988°, a figure of 880° has also been mentioned) and as the decahydrate (density 1.815-1.836 gcm$^{-3}$, melting point 94° with loss of water). Both substances are colorless crystals which dissolve in water through an alkaline reaction. $Na_4P_2O_7$ is formed when disodium phosphate is heated to >200° or by reacting phosphoric acid with soda in a stoichiometric ratio and spray-drying the solution. The decahydrate complexes heavy metal salts and hardness salts and, hence, reduces the hardness of water. Potassium diphosphate (potassium pyrophosphate), $K_4P_2O_7$, exists in the form of the trihydrate and is a colorless hygroscopic powder with a density of 2.33 gcm$^{-3}$ which is soluble iii water, the pH value of a 1% solution at 25° being 10.4.

Relatively high molecular weight sodium and potassium phosphates are formed by condensation of $NaH_2PO_4$ or $KH_2PO_4$. They may be divided into cyclic types, namely the sodium and potassium metaphosphates, and chain types, the sodium and potassium polyphosphates. The chain types in particular are known by various different names: fused or calcined phosphates, Graham's salt, Kurrol's salt and Maddrell's salt. All higher sodium and potassium phosphates are known collectively as condensed phosphates.

The industrially important pentasodium triphosphate, $Na_5P_3O_{10}$ (sodium tripolyphosphate), is a non-hygroscopic white water-soluble salt which crystallizes without water or with $6H_2O$ and which has the general formula NaO—[P(O)(ONa)—O]$_n$—Na where n=3. Around 17 g of the salt free from water of crystallization dissolve in 100 g of water at room temperature, around 20 g at 60° and around 32 g at 100°. After heating of the solution for 2 hours to 100° around 8% orthophosphate and 15% diphosphate are formed by hydrolysis. In the preparation of pentasodium triphosphate, phosphoric acid is reacted with soda solution or sodium hydroxide in a stoichiometric ratio and the solution is spray-dried. Similarly to Graham's salt and sodium diphosphate, pentasodium triphosphate dissolves many insoluble metal compounds (including lime soaps, etc.). Pentapotassium triphosphate, $K_5P_3O_{10}$ (potassium tripolyphosphate), is marketed for example in the form of a 50% by weight solution (>23% $P_2O_5$, 25% $K_2O$). The potassium polyphosphates are widely used in the detergent industry. Sodium potassium tripolyphosphates, which may also be used in accordance with the invention, also exist. They are formed for example when sodium trimetaphosphate is hydrolyzed with KOH:

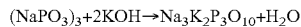
$(NaPO_3)_3 + 2KOH \rightarrow Na_3K_2P_3O_{10} + H_2O$

According to the invention, they may be used in exactly the same way as sodium tripolyphosphate, potassium tripolyphosphate or mixtures thereof. Mixtures of sodium tripolyphosphate and sodium potassium tripolyphosphate or mixtures of potassium tripolyphosphate and sodium potassium tripolyphosphate or mixtures of sodium tripolyphosphate and potassium tripolyphosphate and sodium potassium tripolyphosphate may also be used in accordance with the invention.

Organic cobuilders which may be used in the detergents/cleaners according to the invention include, in particular, polycarboxylates or poly-carboxylic acids, polymeric polycarboxylates, polyaspartic acid, polyacetals, optionally oxidized dextrins, other organic cobuilders (see below) and phosphonates. These classes of substances are described in the following.

Useful organic builders are for example, the polycarboxylic acids usable in the form of their sodium salts, polycarboxylic acids in this context being understood to be carboxylic acids which carry more than one acid function. These include, for example, citric acid, adipic acid, succinic acid, glutaric acid, malic acid, tartaric acid, maleic acid, fumaric acid, sugar acids, aminocarboxylic acids, nitrilotriacetic acid (NTA), providing its use is not ecologically unsafe, and mixtures thereof. Preferred salts are the salts of the polycarboxylic acids, such as citric acid, adipic acid, succinic acid, glutaric acid, tartaric acid, sugar acids and mixtures thereof.

The acids per se may also be used. Besides their building effect, the acids also typically have the property of an acidifying component and, hence, also serve to establish a relatively low and mild pH value in detergents or cleaners unless the pH value obtained by mixing of the other components is required. System-compatible and environmentally safe acids, such as citric acid, acetic acid, tartaric, maleic acid, lactic acid, glycolic acid, succinic acid, glutaric acid, adipic acid, gluconic acid and mixtures thereof, are particularly mentioned in this regard. However, mineral acids, particularly sulfuric acid, or bases, particularly ammonium or alkali metal hydroxides, may also be used as pH adjusters. Such adjusters are present in the compositions according to the invention in quantities of not more than 20% by weight and more particularly in quantities of 1.2% by weight to 17% by weight.

Other suitable builders are polymeric polycarboxylates, i.e. for example the alkali metal salts of polyacrylic or polymethacrylic acid, for example those with a relative molecular weight of 500 to 70,000 g/mol.

The molecular weights mentioned in this specification for polymeric polycarboxylates are weight-average molecular weights $M_w$ of the particular acid form which, basically, were determined by gel permeation chromatography (GPC) using a UV detector. The measurement was carried out against an external polyacrylic acid standard which provides realistic molecular weight values by virtue of its structural similarity to the polymers investigated. These values differ distinctly from the molecular weights measured against polystyrene sulfonic acids as standard. The molecular weights measured against polystyrene sulfonic acids are generally higher than the molecular weights mentioned in this specification.

Particularly suitable polymers are polyacrylates which preferably have a molecular weight of 2,000 to 20,000 g/mol. By virtue of their superior solubility, preferred representatives of this group are the short-chain polyacrylates which have molecular weights of 2,000 to 10,000 g/mol and, more particularly, 3,000 to 5,000 g/mol.

Also suitable are copolymeric polycarboxylates, particularly those of acrylic acid with methacrylic acid and those of acrylic acid or methacrylic acid with maleic acid. Acrylic acid/maleic acid copolymers containing 50 to 90% by weight of acrylic acid and 50 to 10% by weight of maleic acid have proved to be particularly suitable. Their relative molecular weights, based on the free acids, are generally in the range from 2,000 to 70,000 g/mol, preferably in the range from 20,000 to 50,000 g/mol and more preferably in the range from 30,000 to 40,000 g/mol. The (co)polymeric polycarboxylates may be used either in powder form or in the form of an aqueous solution. The content of (co)polymeric polycarboxylates in the detergents can be from 0.5 to 20% by weight and, more particularly, is from 1 to 10% by weight.

In order to improve solubility in water, the polymers may also contain allyl sulfonic acids such as, for example, allyloxybenzene sulfonic acid and methallyl sulfonic acid as monomer.

Other particularly preferred polymers are biodegradable polymers of more than two different monomer units, for example those which contain salts of acrylic acid and maleic acid and vinyl alcohol or vinyl alcohol derivatives as monomers or those which contain salts of acrylic acid and 2-alkylallyl sulfonic acid and sugar derivatives as monomers.

Other preferred copolymers are those which preferably contain acrolein and acrylic acid/acrylic acid salts or acrolein and vinyl acetate as monomers.

Other preferred builders are polymeric aminodicarboxylic acids, salts or precursors thereof. Polyaspartic acids or salts and derivatives thereof which have a bleach-stabilizing effect besides their cobuilder properties are particularly preferred.

Other suitable builders are polyacetals which may be obtained by reaction of dialdehydes with polyol carboxylic acids containing 5 to 7 carbon atoms and at least three hydroxyl groups. Preferred polyacetals are obtained from dialdehydes, such as glyoxal, glutaraldehyde, terephthalaldehyde and mixtures thereof and from polyol carboxylic acids, such as gluconic acid and/or glucoheptonic acid.

Other suitable organic builders are dextrins, for example oligomers or polymers of carbohydrates which may be obtained by partial hydrolysis of starches. The hydrolysis may be carried out by standard methods, for example acid- or enzyme-catalyzed methods. The end products are preferably hydrolysis products with average molecular weights of 400 to 500,000 g/mol. A polysaccharide with a dextrose equivalent (DE) of 0.5 to 40 and, more particularly, 2 to 30 is preferred, the DE being an accepted measure of the reducing effect of a polysaccharide by comparison with dextrose which has a DE of 100. Both maltodextrins with a DE of 3 to 20 and dry glucose sirups with a DE of 20 to 37 and also so-called yellow dextrins and white dextrins with relatively high molecular weights of 2,000 to 30,000 g/mol may be used.

The oxidized derivatives of such dextrins are their reaction products with oxidizing agents which are capable of oxidizing at least one alcohol function of the saccharide ring to the carboxylic acid function. Particularly preferred organic builders for compositions according to the invention are oxidized starches or derivatives thereof according to EP 472 042, WO 97/25399 and EP 755 944.

Other suitable co-builders are oxydisuccinates and other derivatives of disuccinates, preferably ethylenediamine disuccinate. Ethylenediamine-N,N'-disuccinate (EDDS) is preferably used in the form of its sodium or magnesium salts. Glycerol disuccinates and glycerol trisuccinates are also preferred in this connection. The quantities used in zeolite-containing and/or silicate-containing formulations are from 3 to 15% by weight.

Other useful organic co-builders are, for example, acetylated hydroxycarboxylic acids and salts thereof which may optionally be present in lactone form and which contain at least 4 carbon atoms, at least one hydroxy group and at most two acid groups.

Another class of substances with co-builder properties are the phosphonates, more particularly hydroxyalkane and aminoalkane phosphonates. Among the hydroxyalkane phosphonates, 1-hydroxyethane-1,1-diphosphonate (HEDP) is particularly important as a co-builder. It is preferably used in the form of the sodium salt, the disodium salt showing a neutral reaction and the tetrasodium salt an alkaline reaction (pH 9). Preferred aminoalkane phosphonates are ethylenediamine tetramethylene phosphonate (EDTMP), diethylenetriamine pentamethylenephosphonate (DTPMP) and higher homologs thereof. They are preferably used in the form of the neutrally reacting sodium salts, for example as the hexasodium salt of EDTMP or as the hepta- and octasodium salts of DTPMP. Of the phosphonates, HEDP is preferably used as a builder. In addition, the aminoalkane phosphonates have a pronounced heavy metal binding capacity. Accordingly, it can be of advantage, particularly where the foams also contain bleach, to use aminoalkane phosphonates, more particularly DTPMP, or mixtures of the phosphonates mentioned.

In addition, any compounds capable of forming complexes with alkaline earth metal ions may be used as co-builders.

The compositions according to the invention may optionally contain builders in quantities of up to 90% by weight and preferably in quantities of up to 75% by weight. Detergents according to the invention have builder contents of in particular 5% by weight to 50% by weight. In hard surface cleaners according to the invention, particularly dishwasher detergents, the builder content is in particular from 5% by weight to 88% by weight. In a preferred embodiment, such compositions are free from water-soluble builders. In another preferred embodiment, compositions according to the invention, particularly dishwasher detergents, contain 20% by weight to 40% by weight water-soluble organic builders, more particularly alkali metal citrate, 5% by weight to 15% by weight alkali metal carbonate and 20% by weight to 40% by weight alkali metal disilicate.

Solvents which may be used in the liquid or gel-form compositions of detergents/cleaners belong, for example, to the group of monohydric or polyhydric alcohols, alkanolamines or glycolethers providing they are miscible with water in the concentration range indicated. The solvents are preferably selected from ethanol, n- or i-propanol, butanols, ethylene glycol methyl ether, ethylene glycol ethyl ether, ethylene glycol propyl ether, ethylene glycol moo-n-butyl ether, diethylene glycol methyl ether, diethylene glycol diethyl ether, propylene glycol methyl, ethyl or propyl ether, dipropylene glycol monomethyl or monoethyl ether, diisopropylene glycol monomethyl or monoethyl ether, methoxy, ethoxy or butoxy triglycol, 1-butoxyethoxy-2-propanol, 3-methyl-3-methoxybutanol, propylene glycol t-butyl ether and mixtures of these solvents.

Solvents may be present in the liquid or gel-form detergents/cleaners according to the invention in quantities of 0.1 to 20% by weight, preferably in quantities below 15% by weight and more particularly in quantities below 10% by weight.

One or more thickeners, for example thickening systems, may be added to the composition according to the invention in order to adjust its viscosity. These high molecular weight substances, which are also known as swelling agents, generally absorb the liquids and swell in the process before finally changing into viscous, true or colloidal solutions.

Suitable thickeners are inorganic or polymeric organic compounds. The inorganic thickeners include, for example, polysilicic acids, clay minerals, such as montmorillonites, zeolites, silicas and bentonites. The organic thickeners belong to the groups of natural polymers, modified natural polymers and fully synthetic polymers. Examples of naturally occurring polymers are agar agar, carrageen, tragacanth, gum arabic, alginates, pectins, polyoses, guar gum, locust bean gum, starch, dextrins, gelatin and casein. Modified natural substances which may be used as thickeners belong, above all, to the group of modified starches and celluloses and include, for example, carboxymethyl cellulose and other cellulose ethers, hydroxyethyl and hydroxypropyl cellulose and gum ethers. Fully synthetic thickeners include polymers, such as polyacrylic and polymethacrylic compounds, vinyl polymers, polycarboxylic acids, polyethers, polyimines, polyamides and polyurethanes.

The thickeners may be used in a quantity of up to 5% by weight, preferably in a quantity of 0.05 to 2% by weight and more particularly in a quantity of 0.1 to 1.5% by weight, based on the final composition.

The detergents/cleaners according to the invention may optionally contains sequestering agents, electrolytes and other auxiliaries, such as optical brighteners, redeposition inhibitors, silver corrosion inhibitors, dye transfer inhibitors, foam inhibitors, abrasives, dyes and/or perfumes, and microbial agents and/or UV absorbers as further ingredients.

Laundry detergents according to the invention may contain derivatives of diaminostilbenedisulfonic acid or alkali metal salts thereof as optical brighteners. Suitable optical brighteners are, for example, salts of 4,4'-bis-(2-anilino-4-morpholino-1,3,5-triazinyl-6-amino)-stilbene-2,2'-disulfonic acid or compounds of similar composition which contain a diethanolamino group, a methylamino group, an anilino group or a 2-methoxyethylamino group instead of the morpholino group. Brighteners of the substituted diphenyl styryl type, for example alkali metal salts of 4,4'-bis-(2-sulfostyryl)-diphenyl, 4,4'-bis-(4-chloro-3-sulfostyryl)-diphenyl or 4-(4-chlorostyryl)-4'-(2-sulfostyryl)-diphenyl, may also be present. Mixtures of the brighteners mentioned above may also be used.

The function of redeposition inhibitors is to keep the soil detached from the fibers suspended in the wash liquor. Suitable redeposition inhibitors are water-soluble, generally organic colloids, for example starch, glue, gelatin, salts of ether carboxylic acids or ether sulfonic acids of starch or cellulose or salts of acidic sulfuric acid esters of cellulose or starch. Water-soluble polyamides containing acidic groups are also suitable for this purpose. Starch derivatives other than those mentioned above, for example aldehyde starches, etc., may also be used. Cellulose ethers, such as carboxymethyl cellulose (sodium salt), methyl cellulose, hydroxyalkyl cellulose, and mixed ethers, such as methyl hydroxyethyl cellulose, methyl hydroxypropyl cellulose, methyl carboxymethyl cellulose and mixtures thereof, are preferably used, for example in quantities of 0.1 to 5% by weight, based on the composition.

In order to protect silverware against corrosion, silver corrosion inhibitors may be used in dishwashing detergents according to the invention. Silver corrosion inhibitors are known from the prior art and include, for example, benzotriazoles, iron (III) chloride and $CoSO_4$. As known from European patent EP 0 736 084 B1, for example, silver corrosion inhibitors particularly suitable for use together with enzymes are manganese, titanium, zirconium, hafnium, vanadium, cobalt or cerium salts and/or complexes in which the metals mentioned are present in one of the oxidation numbers II, II, IV, V or VI. Examples of such compounds are $MnSO_4$, $V_2O_5$, $V_2O_4$, $VO_2$, $TIOSO_4$, $K_2TiF_6$, $K_2ZrF_6$, $Co(NO_3)_2$, $Co(NO_3)_3$ and mixtures thereof.

Soil release agents or soil repellents are generally polymers which, when used in a laundry detergent, provide the laundry fibers with soil-repelling properties and/or support the soil suspending capacity of the other ingredients of the detergent. A comparable effect can also be observed where they are used in hard surface cleaners.

Particularly effective and long-established soil release agents are copolyesters containing dicarboxylic acid, alkylene glycol and polyalylene glycol units. Examples are copolymers or copolymers of polyethylene terephthalate and polyoxyethylene glycol (DT 16 17 141 or DT 22 00 911). DE-OS 2253063 mentions acidic compositions containing inter alia a copolymer of a dibasic carboxylic acid and an alkylene or cycloalkylene polyglycol. Polymers of ethylene terephthalate and polyethylene oxide terephthalate and their use in detergents is described in DE-PS 28 57 292 and DE-PS 33 24 258 and in EP 0 253 567. European patent EP 066 944 relates to compositions containing a copolyesters of ethylene glycol, polyethylene glycol, aromatic dicarboxylic acid and sulfonated aromatic dicarboxylic acid in certain molar ratios. European patent EP 0 185 427 describes methyl- or ethyl-terminated polyesters containing ethylene and/or propylene terephthalate units and polyethylene oxide terephthalate units and detergents which contain such a soil-release polymer. European patent relates to a polyester which, besides oxyethylene groups and terephthalic acid units, also contains substituted ethylene units and glycerol units. European patent EP 0 241 985 describes polyesters which, besides oxyethylene groups and terephthalic acid units, contain 1,2-propylene, 1,2-butylene and/or 3-methoxy-1,2-propylene groups and glycerol units and which are terminated by $C_{1-4}$ alkyl groups. European patent application EP 0 272 033 describes at least partly $C_{1-4}$ alkyl- or acyl-terminated polyesters containing polypropylene terephthalate and polyoxyethylene terephthalate units. European patent EP 0 274 907 describes sulfoethyl-terminated terephthalate-containing soil-release polyesters. According to European patent application EP 0 357 280, soil-release polyesters containing terephthalate, alkylene glycol and poly-$C_{2-4}$-glycol units are produced by sulfonation of unsaturated terminal groups. International patent application WO 95/32232 relates to acidic aromatic soil-release polyesters. International patent application WO 97/31085 describes soil repellents for cotton fabrics which contain several functional units: a first unit, which may be cationic for example, is capable of adsorption onto the cotton surface by electrostatic interaction, and a second unit which is hydrophobic is responsible for the active substance remaining at the water/cotton interface.

Dye transfer inhibitors suitable for use in laundry detergents according to the invention include, in particular, polyvinyl pyrrolidones, polyvinyl imidazoles, polymeric N-oxides, such as poly-(vinylpyridine-N-oxide) and copolymers of vinyl pyrrolidone with vinyl imidazole.

Where the compositions are used in machine cleaning processes, it can be of advantage to add typical foam inhibitors to them. Suitable foam inhibitors are, for example, soaps of natural or synthetic origin which have a high percentage content of $C_{18-24}$ fatty acids. Suitable non-surface-active foam inhibitors are, for example, organopolysiloxanes and mixtures thereof with microfine, optionally silanized, silica and also paraffins, waxes, microcrystalline waxes and mixtures thereof with silanized silica or bis-stearyl ethylenediamide. Mixtures of different foam inhibitors, for example mixtures of silicones, paraffins and waxes, may also be used with advantage. The foam inhibitors, more particularly silicone- and/or paraffin-containing foam inhibitors, are preferably fixed to a granular water-soluble or water-dispersible support. Mixtures of paraffins and bis-stearyl ethylenediamides are particularly preferred.

In addition, a hard surface cleaner according to the invention may contain abrasive constituents, more particularly from the group consisting of silica flours, wood flours, plastic powders, chalks and glass microbeads and mixtures thereof. Abrasives are present in the cleaners according to the invention is quantity of preferably not more than 20% by weight and more particularly in quantities of 5% to 15% by weight.

Dyes and perfumes are added to the detergents/cleaners according to the invention to improve the aesthetic impression created by the products and to provide the consumer not only with the required washing and cleaning performance but also with a visually and sensorially "typical and unmistakable" product. Suitable perfume oils or fragrances include individual perfume compounds, for example synthetic products of the ester, ether, aldehyde, ketone, alcohol and hydrocarbon type. Perfume compounds of the ester type are, for example, benzyl acetate, phenoxyethyl isobutyrate, p-tert.butyl cyclohexyl acetate, linalyl acetate, dimethyl benzyl carbinyl acetate, phenyl ethyl acetate, linalyl benzoate, benzyl formate, ethyl methyl phenyl glycinate, allyl cyclohexyl propionate, styrallyl propionate and benzyl salicylate. The ethers include, for example, benzyl ethyl ether; the aldehydes include, for example, the linear alkanals containing 8 to 18 carbon atoms, citral, citronellal, citronellyloxyacetaldehyde, cyclamen aldehyde, hydroxycitronellal, lilial and bourgeonal; the ketones include, for example, the ionones, $\alpha$-isomethyl ionone and methyl cedryl ketone; the alcohols include anethol, citronellol, eugenol, geraniol, linalool, phenyl ethyl alcohol and terpineol and the hydrocarbons include, above all, the terpenes, such as limonene and pinene. However, mixtures of various perfumes which together produce an attractive perfume note are preferably used. Perfume oils such as these may also contain natural perfume mixtures obtainable from vegetable sources, for example pine, citrus, jasmine, patchouli, ruse or ylang-ylang oil. Also suitable are clary oil, chamomile oil, clove oil, melissa oil, mint oil, cinnamon leaf oil, lime blossom oil, juniper berry oil, vetiver oil, olibanum oil, galbanum oil and ladanum oil and orange blossom oil, neroli oil, orange peel oil and sandalwood oil. The dye content of detergents/cleaners is usually below 0.01% by weight while perfumes can make up as much as 2% by weight of the formulation as a whole.

The perfumes may be directly incorporated in the detergents/cleaners, although it can also be of advantage to apply the fragrances to supports which strengthen the adherence of the perfume to the articles being washed/cleaned and which provide treated textiles in particular with a long-lasting fragrance through a slower release of the perfume. Suitable support materials are, for example, cyclodextrins, the cyclodextrin/perfume complexes optionally being coated with other auxiliaries. Another preferred support for perfumes is the described zeolite X which is also capable of absorbing perfumes instead of or in admixture with surfactants. Accordingly, detergents/cleaners containing the described zeolite X and perfumes preferably absorbed at least partly on the zeolite are preferred.

Preferred dyes which the expert will find no difficulty in selecting have high stability in storage, are unaffected by the other ingredients of the composition and by light and do not show pronounced substantivity towards textile fibers so as not to color them.

To control microorganisms, detergents/cleaners may contain antimicrobial agents. Depending on the antimicrobial spectrum and the action mechanism, antimicrobial agents are classified as bacteriostatic agents and bactericides, fungistatic agents and fungicides, etc. Important representatives of these groups are, for example, benzalkonium chlorides, alkylaryl sulfonates, halophenols and phenol mercuriacetate. In the context of the teaching according to the invention, the expressions "antimicrobial activity" and "antimicrobial agent" have the usual meanings as defined, for example, by K. H. Wallhäußer in "*Praxis der Sterilisation, Desinfektion-Konservierung: Keimidentifizierung-Betriebshygiene*" (5th Edition, Stuttgart/New York: Thieme, 1995), any of the substances with antimicrobial activity described therein being usable. Suitable antimicrobial agents are preferably selected from the groups of alcohols, amines, aldehydes, antimicrobial acids and salts thereof, carboxylic acid esters, acid amides, phenols, phenol derivatives, diphenyls, diphenylalkanes, urea derivatives, oxygen and nitrogen acetals and formals, benzamidines, isothiazolines, phthalimide derivatives, pyridine derivatives, antimicrobial surface-active compounds, guanidines, antimicrobial amphoteric compounds, quinolines, 1,2-dibromo-2,4-dicyanobutane, iodo-2-propyl butyl carbamate, iodine, iodophores, peroxo compounds, halogen compounds and mixtures of the above.

The antimicrobial agent may be selected from ethanol, n-propanol, i-propanol, butane-1,3-diol, phenoxyethanol, 1,2-propylene glycol, glycerol, undecylenic acid, benzoic acid, salicylic acid, dihydracetic acid, o-phenylphenol, N-methyl morpholine acetonitrile (MMA), 2-benzyl-4-chlorophenol, 2,2'-dimethylene-bis-(6-bromo-4-chlorophenol), 4,4'-dichloro-2'-hydroxydiphenyl ether (Dichlosan), 2,4,4'-trichloro-2'-hydroxydiphenyl ether (Triclosan), chlorhexidine, N-(4-chlorophenyl)-N-3,4-dichlorophenyl)-urea, N,N'-(1,10-decanediyldi-1-pyridinyl-4-ylidene)-bis-(1-octanamine)-dihydrochloride, N,N'-bis-(4-chlorophenyl)-3,12-diimino-2,4,11,13-tetraazatetradecane diimidoamide, glucoprotamines, antimicrobial surface-active quaternary compounds, guanidines, including the bi- and polyguanidines such as, for example, 1,6-bis-(2-ethylhexyl-biguanidohexane)-dihydrochloride, 1,6-di-($N_1,N_1$'-phenyl-diguanido-$N_5,N_5$')-hexane tetrahydrochloride, 1,6-di-($N_1$, $N_1$'-phenyl-$N_1,N_1$-methyldiguanido-$N_5$, $N_5$')-hexane dihydrochloride, 1,6-di-($N_1,N_1$'-o-chlorophenyldiguanido-$N_5$, $N_5$')-hexane dihydrochloride, 1,6-di-($N_1,N_1$'-2,6-dichlorophenyldiguanido-$N_5,N_5$')-hexane dihydrochloride, 1,6-di-[$N_1N_1$'-β-(p-methoxyphenyl)-diguanido-$N_5,N_5$']-hexane dihydrochloride, 1,6-di-($N_1N_1$'-α-methyl-β-phenyl-diguanido-$N_5,N_5$')-hexane dihydrochloride, 1,6-di-($N_1,N_1$'-p-nitrophenyldiguanido-$N_5,N_5$')-hexane dihydrochloride, ω:ω-di-($N_1,N_1$'-phenyldiguanido-$N_5,N_5$')-di-n-propyl ether dihydrochloride, ω:ω'-di-($N_1,N_1$'-p-chlorophenyldiguanido-$N_5,N_5$')-di-n-propyl ether tetrahydrochloride, 1,6-di-($N_1,N_1$'-2,4-dichlorophenyldiguanido-$N_5,N_5$')-hexane tetrahydrochloride, 1,6-di-($N_1,N_1$'-p-methylphenyldiguanido-$N_5,N_5$')-hexanedihydrochloride, 1,6-di-($N_1,N_1$'-2,4,5-trichlorophenyldiguanido-$N_5,N_5$')-hexane tetrahydrochloride, 1,6-di-[$N_1,N_1$'-α-(p-chlorophenyl)-ethyldiguanido-$N_5,N_5$']-hexane dihydrochloride, ω:ω-di-($N_1$, $N_1$'-p-chlorophenyldiguanido-$N_5,N_5$')-m-xylene dihydrochloride, 1,12-di-($N_1,N_1$'-p-chlorophenyldiguanido-$N_5,N_5$')-dodecane dihydrdochloride, 1,10-di-($N_1,N_1$'-phenyldiguanido-$N_5,N_5$')-decane tetrahydrochloride, 1,12-di-($N_1,N_1$'-phenyldiguanido-$N_5,N_5$')-dodecane tetrahydrochloride, 1,6-di-($N_1,N_1$'-o-chlorophenyl-diguanido-$N_5,N_5$')-hexane dihydrochloride, 1,6-di-($N_1,N_1$'-o-chlorophenyldiguanido-$N_5,N_5$')-hexane tetrahydrochloride, ethylene-bis-(1-tolylbiguanide), ethylene-bis-(p-tolylbiguanide), ethylene-bis-(3,5-dimethylphenylbiguanide), ethylene-bis-(p-tert.amylphenylbiguanide), ethylene-bis-(nonylphenylbiguanide), ethylene-bis-(phenylbiguanide), ethylene-bis-(N-butylphenylbiguanide), ethylene-bis-(2,5-diethoxyphenylbiguanide), ethylene-bis-(2,4-dimethylphenylbiguanide), ethylene-bis-(o-diphenylbiguanide), ethylene-bis-(mixed-amylnaphthylbiguanide), N-butylethylene-bis-(phenylbiguanide), trimethylene-bis-(o-tolylbiguanide), N-butyltrimethylene-bis-(phenylbiguanide) and the corresponding salts, such as acetates, gluconates, hydrochlorides, hydrobromides, citrates, bisulfites, fluorides, polymaleates, N-cocoalkyl sarcosinates, phosphites, hypophosphites, perfluorooctanoates, silicates, sorbates, salicylates, maleates, tartrates, fumarates, ethylenediamine tetraacetates, iminodiacetates, cinnamates, thiocyanates, arginates, pyromellitates, tetracarboxybutyrates, benzoates, glutarates, monofluorophosphates, perfluoropropionates and mixtures thereof. Halogenated xylene and cresol derivatives, such as p-chloro-m-cresol or p-chloro-m-xylene, and natural antimicrobial agents of vegetable origin (for example from spices or herbs), animal and microbial origin are also suitable. Preferred antimicrobial agents are antimicrobial surface-active quaternary compounds, a natural antimicrobial agent of vegetable origin and/or a natural antimicrobial agent of animal origin and, most preferably, at least one natural antimicrobial agent of vegetable origin from the group comprising caffeine, theobromine and theophylline and essential oils, such as eugenol, thymol and geraniol, and/or at least one natural antimicrobial agent of animal origin from the group comprising enzymes, such as protein from milk, lysozyme and lactoperoxidase and/or at least one antimicrobial surface-active quaternary compound containing an ammonium, sulfonium, phosphonium, iodonium or arsonium group, peroxo compounds and chlorine compounds. Substances of microbial origin, so-called bacteriozines, may also be used.

The quaternary ammonium compounds (QUATS) suitable as antimicrobial agents have the general formula $(R^1)(R^2)(R^3)(R^4)N^+X^-$, in which $R^1$ to $R^4$ may be the same or different and represent $C_{1-22}$ alkyl groups, $C_{7-28}$ aralkyl groups or heterocyclic groups, two or—in the case of an aromatic compound, such as pyridine—even three groups together with the nitrogen atom forming the heterocycle, for example a pyridinium or imidazolinium compound, and $X^-$ represents halide ions, sulfate ions, hydroxide ions or similar anions. In the interests of optimal antimicrobial activity, at least one of the substituents preferably has a chain length of 8 to 18 and, more preferably, 12 to 16 carbon atoms.

QUATS can be obtained by reaction of tertiary amines with alkylating agents such as, for example, methyl chloride, benzyl chloride, dimethyl sulfate, dodecyl bromide and also ethylene oxide. The alkylation of tertiary amines with one long alkyl chain and two methyl groups is particularly simple. The quaternization of tertiary amines containing two long chains and one methyl group can also be carried out under mild conditions using methyl chloride. Amines containing three long alkyl chains or hydroxy-substituted alkyl chains lack reactivity and are preferably quaternized with dimethyl sulfate.

Suitable QUATS are, for example, benzalkonium chloride (N-alkyl-N,N-dimethylbenzyl ammonium chloride, CAS No. 8001-54-5), benzalkon B (m,p-dichlorobenzyl dimethyl-$C_{12}$-alkyl ammonium chloride, CAS No. 58390-78-6), benzoxonium chloride (benzyldodecyl-bis-(2-hydroxyethyl)-ammonium chloride), cetrimonium bromide (N-hexadecyl-N,N-trimethyl ammonium bromide, CAS No. 57-09-0), benzetonium chloride (N,N-dimethyl-N-[2-[2-[p-(1,1,3,3-tetramethylbutyl)-phenoxy]-ethoxy]-ethyl]-benzyl ammonium chloride, CAS No. 121-54-0), dialkyl dimethyl ammonium chlorides, such as di-n-decyldimethyl ammonium chloride (CAS No. 7173-51-5-5), didecyldimethyl ammonium bromide (CAS No. 2390-68-3), dioctyl dimethyl ammonium chloride, 1-cetylpyridinium chloride (CAS No. 123-03-5) and thiazoline iodide (CAS No. 15764-48-1) and mixtures thereof. Particularly preferred QUATS are the benzalkonium chlorides containing $C_{8-18}$ alkyl groups, more particularly $C_{12-14}$ alkyl benzyl dimethyl ammonium chloride.

Benzalkonium halides and/or substituted benzalkonium halides are commercially obtainable, for example, as Barquat® from Lonza, Marquat® from Mason, Variquat® from Witco/Sherex and Hyamine® from Lonza and as Bardac® from Lonza. Other commercially obtainable antimicrobial agents are N-(3-chloroallyl)-hexaminium chloride, such as Dowicide® and Dowicil® from Dow, benzethonium chloride, such as Hyamine® 1622 from Rohm & Haas, methyl benzethonium chloride, such as Hyamine® 10X from Rohm & Haas, cetyl pyridinium chloride, such as cepacolchloride from Merrell Labs.

The antimicrobial agents are used in quantities of 0.0001% by weight to 1% by weight, preferably in quantities of 0.001% by weight to 0.8% by weight, more preferably in quantities of 0.005 to 0.3% by weight and most preferably in quantities of 0.01 to 0.2% by weight.

In addition, the compositions may optionally contain UV absorbers which are absorbed onto the treated textiles and improve the light stability of the fibers and/or the light stability of the other formulation ingredients. UV absorbers are organic substances (light filters) which are capable of absorbing ultraviolet rays and of releasing the energy absorbed in the form of longer-wave radiation, for example heat.

Compounds which possess these desired properties are, for example, the compounds which act by radiationless deactivation and derivatives of benzophenone with substituents in the 2- and/or 4-position. Other suitable UV absorbers are substituted benzotriazoles, 3-phenyl-substituted acrylates (cinnamic acid derivatives, optionally with cyano groups in the 2-position), salicylates, organic Ni complexes and natural substances, such as umbelliferone and the body's own urocanic acid. Particular significance attaches to the biphenyl and, above all, stilbene derivatives described, for example, EP 0728740 A which are commercially available as Tinosorb® FD and Tinosorb® FR ex Ciba. Suitable UV-B absorbers include 3-benzylidene camphor or 3-benzylidene norcamphor and derivatives thereof, for example 3-(4-methylbenzylidene)-camphor as described in EP-B1 0693471; 4-aminobenzoic acid derivatives, preferably 4-(dimethylamino)-benzoic acid-2-ethylhexyl ester, 4-(dimethylamino)-benzoic acid-2-octyl ester and 4-(dimethylamino)-benzoic acid amyl ester; esters of cinnamic acid, preferably 4-methoxycinnamic acid-2-ethylhexyl ester, 4-methoxycinnamic acid propyl ester, 4-methoxycinnamic acid isoamyl ester, 2-cyano-3,3-phenylcinnamic acid-2-ethylhexyl ester (Octocrylene); esters of salicylic acid, preferably salicylic acid-2-ethylhexyl ester, salicylic acid-4-isopropylbenzyl ester, salicylic acid homomethyl ester; derivatives of benzophenone, preferably 2-hydroxy-4-methoxybenzophenone, 2-hydroxy-4-methoxy-4'-methylbenzophenone, 2,2'-dihydroxy-4-methoxybenzophenone; esters of benzalmalonic acid, preferably 4-methoxybenzmalonic acid di-2-ethylhexyl ester; triazine derivatives such as, for example, 2,4,6-trianilino-(p-carbo-2'-ethyl-1'-hexyloxy)-1,3,5-triazine and Octyl Triazone as described in EP 0818450 A1 or Dioctyl Butamido Triazone (Uvasorb® HEB): propane-1,3-diones such as, for example, 1-(4-tert.butylphenyl)-3-(4'-methoxyphenyl)-propane-1,3-dione; ketotricyclo(5.2.1.0)decane derivatives as described in EP 0694521 B1. Other suitable UV-B absorbers are 2-phenylbenzimidazole-5-sulfonic acid and alkali metal, alkaline earth metal, ammonium, alkylammonium, alkanolammonium and glucammonium salts thereof; sulfonic acid derivatives of benzophenones, preferably 2-hydroxy-4-methoxybenzophenone-5-sulfonic acid and salts thereof; sulfonic acid derivatives of 3-benzylidene camphor such as, for example, 4-(2-oxo-3-bornylidenemethyl)-benzene sulfonic acid and 2-methyl-5-(2-oxo-3-bornylidene)-sulfonic acid and salts thereof.

Typical UV-A filters are, in particular, derivatives of benzoyl methane such as, for example, 1-(4'-tert.butylphenyl)-3-(4'-methoxyphenyl)-propane-1,3-dione, 4-tert.butyl-4'-methoxydibenzoyl methane (Parsol 1789), 1-phenyl-3-(4'-isopropylphenyl)-propane-1,3-dione and the enamine compounds described in DE 19712033 A1 (BASF). The UV-A and UV-B filters may of course also be used in the form of mixtures. Besides the soluble substances mentioned, insoluble light-blocking pigments, i.e. finely dispersed, preferably "nanoized" metal oxides or salts, may also be used for this purpose. Examples of suitable metal oxides are, in particular, zinc oxide and titanium dioxide and also oxides of iron, zirconium oxide, silicon, manganese, aluminium and cerium and mixtures thereof. Silicates (talcum), barium sulfate and zinc stearate may be used as salts. The oxides and salts are used in the form of the pigments for skin-care and skin-protecting emulsions and decorative cosmetics. The particles should have a mean diameter of less than 100 nm, preferably between 5 and 50 nm and more preferably between 15 and 30 nm. They may be spherical in shape although ellipsoidal particles or other non-spherical particles may also be used. The pigments may also be surface-treated, i.e. hydrophilicized or hydrophobicized. Typical examples are coated titanium dioxides, for example Titandioxid T 805 (Degussa) and Eusolex® T2000 (Merck). Suitable hydrophobic coating materials are, above all, silicones and, among these, especially trialkoxyoctylsilanes or simethicones. Micronized zinc oxide is preferably used. Other suitable UV filters can be found in P. Finkel's review in SÖFW-Journal 122, 543 (1996).

The UV absorbers are normally used in quantities of 0.01% by weight to 5% by weight and preferably 0.03% by weight to 1% by weight.

Proteins according to the invention and/or other proteins may also require special protection in detergents and cleaners. Compositions according to the invention may contain stabilizers for this purpose.

One group of stabilizers is reversible protease inhibitors which dissociate off on dilution of the composition in the wash liquor. Benzamidine hydrochloride and leupeptin are established for this purpose. Borax, boric acids, boron acids or salts or esters thereof, including above all phenylboron acids orthosubstituted by aromatic groups, for example in accordance with WO 95/12655, metasubstituted by aromatic groups in accordance with WO 92/19707 and parasubstituted by aromatic groups in accordance with U.S. Pat. No. 5,972, 873 or salts or esters thereof, are often used for this purpose. WO 98/13460 and EP 583 534 disclose peptide aldehydes, i.e. oligopeptides with a reduced C-terminus, especially those of 2-50 monomers, for the reversible inhibition of detergent proteases. The peptidic reversible protease inhibitors include inter alia ovomucoid (WO 93/00418). WO 00/01826, for example, discloses specific reversible peptide inhibitors for the protease subtilisin for use in protease-containing compositions while WO 00/01831 discloses corresponding fusion proteins of protease and inhibitor.

Other enzyme stabilizers are aminoalcohols, such as mono-, di-, triethanol- and -propanolamine and mixtures thereof, aliphatic carboxylic acids up to $C_{12}$ as known, for example, from EP 0 378 261 and WO 97/05227, such as succinic acid, other dicarboxylic acids or salts of the acids mentioned. End-capped fatty acid amide alkoxylates are disclosed for this purpose in German patent application DE 19650537. Certain organic acids used as builders are additionally capable of stabilizing an enzyme present, as disclosed in WO 97/18287.

Lower aliphatic alcohols, but above all polyols such as, for example, glycerol, ethylene glycol, propylene glycol or sorbitol are other frequently used enzyme stabilizers. According to a more recent application (EP 0 965 268), diglycerophosphate also stabilizes against denaturing by physical influences. Calcium salts, for example calcium acetate or the calcium formate disclosed for this purpose in EP 0 028 865, and magnesium salts, for example according to European patent application EP 0 378 262, are also used.

Polyamide oligomers (WO 99/43780) or polymeric compounds, such as lignin (WO 97/00932), water-soluble vinyl copolymers (EP 828 762) or, as disclosed in EP 702 712, cellulose ethers, acrylic polymers and/or polyamides stabilize the enzyme preparation inter alia against physical influences or pH variations. Polymers containing polyamine-N-oxide (EP 587 550 and EP 581 751) simultaneously act as enzyme stabilizers and as dye transfer inhibitors. Other polymer stabilizers are the linear $C_{8-18}$ polyoxyalkylene disclosed besides other constituents in WO 97/05227. Alkyl polyglycosides could stabilize the enzymatic components of the composition according to the invention and even enhance their performance, as disclosed in WO 97/43377 and WO 98/45396. Crosslinked N-containing compounds, as disclosed in WO 98/17764, perform a dual role as soil release agents and as enzyme stabilizers. Hydrophobic nonionic polymer in admixture with other stabilizers according to WO 97/32958 has a stabilizing effect on a cellulase so that these or similar constituents could also be suitable for the enzyme essential to the invention.

Reducing agents and antioxidants, as disclosed inter alia in EP 780 466, increase the stability of the enzymes to oxidative disintegration. Sulfur-containing reducing agents are known, for example, from EP 0 080 748 and EP 0 080 223. Other examples are sodium sulfite (EP 533 239) and reducing sugars (EP 656 058).

In many cases, combinations of stabilizers are also used, for example the combination of polyols, boric acid and/or borax in WO 96/31589, the combination of boric acid or borate, reducing salts and succinic acid or other dicarboxylic acids in EP 126 505 or the combination of boric acid or borate with polyols or polyamino compounds and with reducing salts as disclosed in EP 080 223. According to WO 98/13462, the effect of peptide/aldehyde stabilizers is enhanced by combination with boric acid and/or boric acid derivatives and polyols and, according to WO 98/13459 is further enhanced by the additional use of calcium ions.

Compositions with stabilized enzyme activities represent preferred embodiments of the present invention. Compositions containing enzymes stabilized in several of the ways mentioned are particularly preferred.

Compositions according to the invention contain proteins or derivatives essential to the invention in quantities of preferably 0.000001% by weight to 5% by weight and, with increasing preference, in quantities of 0.00005 to 4% by weight, 0.00001 to 3% by weight, 0.0001 to 2% by weight and, in a most particularly preferred embodiment, in quantities of 0.001 to 1% by weight. The protein concentration can be determined by known methods, for example the BCA method (bicinchonic acid; 2,2'-biquinolyl-4,4'-dicarboxylic acid) or the biuret method (A. G. Gornall, C. S. Bardawill and M. M. David, J. Biol. Chem. 177, (1948), pp. 751-766).

Besides the protein essential to the invention, compositions according to the invention may contain other amylolytic enzymes, more particularly α-amylases. These may also include the enzymes established for use in detergents/cleaners which were mentioned at the beginning. Examples of commercially available amylases are BAN®, Termamyl®, Purastar®, Amylase-LT®, Maxamyl®, Duramyl® and/or Purafect® Ox-Am. This is advisable when the various enzymes are capable of complementing one another. Such complementing may occur, for example, in a regulatory sense, for example through mutual activation or inactivation. It may arise, for example, through at least a part of the enzyme essential to the invention, which is not homologous to the known α-amylases, having an influence on the amylolytic activities not essential to the invention.

However, the joint use can also be appropriate in view of differing substrate specificities. Both are embodiments of the present invention.

It can be of advantage, particularly with chemically diverse soils, to use amylolytic enzymes in detergents/cleaners together with other detersive enzymes and/or enzymes with cleaning activity. Accordingly, detergents/cleaners characterized by other enzymes besides a protein according to the invention represent preferred embodiments of the present invention.

Besides other amylases, for example proteases, these other enzymes include, for example, lipases, cutinases, esterases, pullulanases, cellulases, hemicellulases and/or xylanases and mixtures thereof. Proteases, lipases, β-glucanases and/or cellulases are particularly preferred. Other enzymes add to the cleaning performance of corresponding compositions through their particular specific enzymatic activity. These include, for example, oxidoreductases or peroxidases as components of enzymatic bleaching systems, laccases (WO 00/39306), β-glucanases (WO 99/06515 and WO 99/06516) or pectin-dissolving enzymes (WO 00/42145) which are used in particular in specialty detergents.

Examples of commercially obtainable enzymes for use in compositions according to the invention are proteases, such as subtilisin BPN', Properase®, BLAP®, Optimase®, Opticlean®, Maxatase®, Maxacal®, Maxapem®, Alcalase®, Esperase®, Savinase®, Durazym®, Everlase® and/or Purafect®G or Purafect®OxP, and lipases, such as Lipolase®, Lipomax®, Lumafast® and/or Lipozym®.

The protease activity in such compositions may be determined by the method described in Tenside, Vol. 7 (1970), pp. 125-132. It is expressed accordingly, in PU (protease units). The protease activity of preferred compositions can be as high as 1,500,000 protease units per gram preparation (PU, as determined by the method described in Tenside, Vol. 7 (1970), pp. 125-132).

So far as their isolation is concerned, suitable enzymes are, above all, those obtained from microorganisms, such as bacteria or fungi, for example from *Bacillus subtilis, Bacillus licheniformis, Streptomyces griseus, Humicola lanuginosa, Humicola insolens, Pseudomonas pseudoalcaligenes* or *Pseudomonas cepacia*, more particularly the enzyme mixtures formed naturally by these strains or mixtures with other strains. They are isolated in known manner by fermentation processes from suitable microorganisms which are described, for example, in German Offenlegungsschrifts DE 1940488 and DE 2121397, in US patents U.S. Pat. No. 3,623,957 and U.S. Pat. No. 4,264,738, in European patent application EP 006 638 and in International patent application WO 91/02792.

These optional additional enzymes may also be adsorbed onto carriers and/or encapsulated in membrane materials to protect them against premature inactivation, as described for example in European patent EP 0 564 476 or in International patent application WO 94/23006. They are present in detergents in quantities of preferably up to 10% by weight and more particularly from 0.2% by weight to 2% by weight, enzymes stabilized against oxidative degradation—as known, for example, from International patent application WO 94/18314—being particularly preferred.

Compositions according to the invention may consist of several phases, for example in order to release the active ingredients present separately from one another in time or space. The phases may be in various aggregate states but, in a particular embodiment, are two phases in the same aggregate state.

Compositions according to the invention which are made up of several solid components may readily be produced by mixing various powders or granules having various ingredients and/or different release behavior with one another in an overall loose form. The production of solid, single-phase or multi-phase compositions according to the invention can be carried out in known manner, for example by spray drying or granulation, the enzymes and optionally other heat-sensitive ingredients, such as bleaching agents for example, optionally being separately added at a later stage. Compositions according to the invention with a high bulk density, more particularly in the range from 650 to 950 g/l, are preferably produced by a process involving an extrusion step known from EP 0 486 592. Another preferred production process based on granulation is described in European patent EP 0 642 576.

Proteins can be used, for example, in dried, granulated, or encapsulated form or in encapsulated and additionally dried form for solid detergents/cleaners. They may be added separately, i.e. as a separate phase, or together with other constituents in the same phase without or without compacting. If microencapsulated enzymes are to be processed in solid form, the water can be removed from the aqueous solutions resulting from working up, for example by spray drying, centrifuging or resolubilization. The particles obtained in this way normally have a particle size of 50 to 200 μm.

The encapsulated form is appropriate for protecting the enzymes from other constituents, such as bleaching agents for example, or for facilitating controlled release. Depending on their size, the capsules are millicapsules, microcapsules or nanocapsules, microcapsules being particularly preferred for enzymes. Microcapsules are disclosed, for example, in patent applications WO 97/24177 and DE 19918267. In another possible encapsulation process which starts out from a mixture of the enzyme solution with a solution or suspension of starch or a starch derivative, the enzymes suitable for use in detergents or cleaners are encapsulated in starch or the starch derivative. One such encapsulation process is described in German application DE 19956382, "A process for the production of microencapsulated enzymes".

Another method of producing a solid composition according to the invention is tableting or compacting. The tablets produced may be single-phase or multi-phase tablets. Accordingly, this supply form also enables a solid composition according to the invention to be produced with two solid phases. To produce compositions according to the invention in the form of single-phase or multi-phase, single-color or multi-color tablets which may consist of several layers, all the constituents—optionally per layer—may be mixed together in a mixer and the resulting mixture may be tabletted in conventional tablet presses, for example eccentric presses or rotary presses, under applied pressures of about 50 to 100 kN·cm$^2$ and preferably 60 to 70 kN/cm$^2$. With multilayer tablets in particular, it can be of advantage for at least one layer to be pre-compressed. This is preferably done by applying pressures of 5 to 20 kN/cm$^2$ and more particularly 10 to 15 kN/cm$^2$. A tablet produced in this way preferably has a weight of 10 g to 50 g and more particularly 15 g to 40 g. The tablets may be of any shape, including round, oval or angular and variations thereof.

The enzymes and even a protein essential to the invention—starting from a conventionally performed protein isolation and preparation in concentrated aqueous or nonaqueous solution—may be added to liquid, gel-form or paste-form compositions according to the invention, for example, in liquid form, i.e. as a solution, suspension or emulsion, but also in gel form or in encapsulated form or as a dried powder. Such detergents or cleaners according to the invention in the form of solutions in typical solvents are generally prepared by simple mixing of the ingredients which may be introduced into an automatic mixer as such or in the form of a solution.

Embodiments of the invention are liquid, gel-form or paste-form compositions to which a protein essential to the invention and/or one of the other proteins present and/or one of the other ingredients present have been added in the form of microcapsules. Corresponding compositions containing capsules of amylase-sensitive material are particularly preferred. The use of amylase-sensitive materials and the amylolytic enzyme essential to the invention together in a detergent or cleaner can have synergistic effects, for example such that the starch-splitting enzyme supports the splitting of microcapsules and hence the release of the encapsulated ingredients so that they are only released at a certain time and not during storage and/or not at the beginning of the cleaning process. This mechanism can form the basis of complex detergent or cleaning systems containing various ingredients and various types of capsules which represent preferred embodiments of the present invention.

A comparable effect is observed when the ingredients of the detergent or cleaner are distributed among at least two different phases, for example two or more solid, joined-together phases of a tablet-form detergent or cleaner or various granules within the same powder-form detergent/cleaner. Two-phase or multi-phase cleaners for use both in dishwashers and in detergents are already known. The activity of an amylolytic enzyme in a previously activated phase is essential for the activation of a later phase where it is surrounded by an amylase-sensitive membrane or coating or the amylase sensitive material is an integral part of the solid phase during whose partial or complete hydrolysis the phase in question disintegrates. Accordingly, the use of the enzyme essential to the invention for this purpose is a preferred embodiment of the present invention.

The ingredients of detergents/cleaners are able suitably to support one another in their performance. The synergistic use of amylase and dye transfer inhibitors for increasing cleaning performance is disclosed, for example, in patent application WO 99/63035. It is also known that polymers which can simultaneously be used as co-builders, such as alkyl polyglycosides for example, can stabilize and increase the activity and the stability of enzymes present, cf. patent application WO 98/45396. An amylolytic activity essential to the invention can also be modified, more particularly stabilized and/or increased, by one of the other constituents mentioned above. Accordingly, correspondingly adapted formulations for compositions according to the invention represent particularly preferred embodiments of the present invention. This applies in particular when the washing or cleaning performance of the composition is increased in this way.

The basic concept of the present invention is also embodied in processes for cleaning textiles or hard surfaces which are characterized in that an amylolytic protein or derivative according to the invention becomes active in at least one of the process steps.

Machine cleaning processes are distinguished by multistage cleaning programs, i.e. by the fact that various components with cleaning activity are applied to the articles to be cleaned at different times from one another. Such processes are applied, for example, in the cleaning of institutional food preparation units. On the other hand, proteins essential to the invention, by virtue of their enzymatic activity, are themselves capable of attacking carbohydrate-containing soils, even in the partial or complete absence of detergents or other ingredients characteristic of detergents or cleaners. Accordingly, in one embodiment of the present invention, a machine cleaning process for textiles or hard surfaces may also be selected in which a protein essential to the invention acts on the soils for a certain period without other cleaning-active components.

Preferred embodiments of the present invention are any cleaning processes, including manual, but especially machine cleaning processes, which are characterized in that an amylolytic protein or derivative essential to the invention becomes active in at least one of the process steps. Such processes may be both process for cleaning textiles or comparable materials and processes for cleaning hard surfaces.

As shown in the Examples, the α-amylase from Bacillus sp. A 7-7 (DSM 12368) essential to the invention is suitable, when incorporated in appropriate detergents or cleaners, both for increasing the washing performance of machine detergents for textiles and for increasing the cleaning performance of dishwasher detergents.

Accordingly, other preferred embodiments of the present invention are any cleaning processes, including manual, but especially machine cleaning processes, which are characterized in that a composition according to the invention is used in at least one of the process steps. Such processes may be both processes for cleaning textiles or comparable materials and processes for cleaning hard surfaces.

Quantities of protein or fragment according to the invention particularly suitable for use in cleaning processes, for example in conventional domestic dishwashers or domestic washing machines, are 0.02 mg to 400 mg of the amylolytic protein or fragment, preferably 0.01 mg to 200 mg and more particularly 0.02 mg to 100 mg of the amylolytic enzyme or fragment per application.

In one possible embodiment of machine cleaning processes for textiles or hard surfaces, active concentrations of 0.0005 mg to 10 mg per liter wash liquid and preferably 0.005 mg to 8 mg per liter wash liquor have proved to be particularly suitable for a protein essential to the invention. Accordingly, they represent preferred embodiments of the present invention. In other suitable embodiments, the corresponding values may differ significantly from the above figures, particularly when it is taken into account that machines consuming between 5 and 50 liters of wash liquor for virtually the same quantity of detergent are used for machine cleaning processes.

The use of a protein according to the invention or a composition according to the invention represents another embodiment of the present invention. This use may take place by machine or in any other, more particularly manual, way. This concerns the cleaning of all kinds of materials, more particularly textiles or hard surfaces. The protein essential to the invention may be embedded in a formulation of other detersive substances or, depending on its nature, may even be largely unaccompanied by such compounds.

Another corresponding embodiment is the use of a protein according to the invention on its own for cleaning textiles or hard surfaces, more particularly in a multistage cleaning process.

Preferred embodiments are any potential applications where compositions according to the invention for cleaning textiles or hard surfaces are used.

An important use is characterized in that the amylolytic protein or fragment is used in a quantity of 0.02 mg to 400 mg, preferably 0.01 mg to 200 mg and more particularly 0.02 mg to 100 mg per application in a dishwasher or washing machine.

The use of proteins or derivatives according to the invention for completely or partly dissolving protective layers around constituents of solid detergents or cleaners or disintegrating solid phases with amylase-sensitive materials present in, or surrounding, them is another embodiment of the present invention. The same also applies to the embodiments where amylolytic proteins are present in one of these phases either on their own or together with at least one other detersive substance or an active substance which supports the cleaning effect. To this extent, the amylolytic protein is intended to activate the relevant phases or other phases in a detergent or cleaner consisting of more than one phase. The release of the ingredients to produce a cleaning effect of the ingredients on hard surfaces or a textile-like material is particularly preferred from this perspective also.

The use of the enzyme according to the invention to achieve the partial or complete dissolution of carbohydrate-containing capsules, more especially nanocapsules, microcapsules or millicapsules, in liquid, gel-form or paste-form compositions is an embodiment of the present invention of which the significance for the controlled release of the encapsulated ingredients of the compositions has already been discussed in the foregoing. This embodiment is a particularly preferred embodiment of the invention when the ingredients are released to produce a cleaning effect on a hard surface or a textile-like material.

Another embodiment is the use of a protein or derivative according to the invention for the treatment of raw materials or intermediate products in textile manufacture, more particularly for desizing cotton.

Raw materials and intermediate products for textile production, for example those based on cotton, are finished with starch during their production and further processing in order to facilitate better processing. This process, which is applied both to yarns and intermediate products and to textiles, is known as sizing. Amylolytic proteins according to the invention are suitable for removing the size, i.e. the starch-containing protective layer (desizing).

Another embodiment of the invention are processes for liquefying starch, more particularly for producing ethanol, which are characterized in that they use a protein or derivative according to the invention.

For liquefying starch, starch swollen in water or buffer is incubated with amylolytic enzymes so that the polysaccharide is split into smaller constituents, ultimately mainly into maltose. Enzymes according to the invention are preferably used for such a process or for one of the steps it involves where their biochemical properties allow them to be readily integrated into a corresponding production process. This may the case, for example, when they are to be introduced into a process step in addition to other enzymes which require the same reaction conditions. Amylolytic proteins according to the invention are particularly preferred where the products which they themselves form are the focus of interest. The liquefaction of starch may also represent one step in a multi-stage process for producing ethanol or derivatives thereof, for example acetic acid.

Another embodiment of the invention is the use of a protein or derivative according to the invention for the production of linear and/or short-chain oligosaccharides.

By virtue of their enzymatic activity, amylolytic proteins according to the invention mainly form relatively high molecular weight oligosaccharides, such as maltohexaose, maltoheptaose or maltooctaose for example, from starch-like polymers after a relatively short incubation period. After a relatively long incubation period, there is an increase in the proportion of lower oligosaccharides, such as maltose or maltotriose for example, among the reaction products. Where there is a particular interest in certain reaction products, corresponding variants of proteins according to the invention and/or the reaction conditions may be modified accordingly.

This is particularly attractive when pure compounds are not the main concern, but rather mixtures of similar compounds as, for example, in the formation of solutions, suspensions or gels having only certain physical properties.

Another embodiment is the use of a protein or derivative according to the invention for the hydrolysis of cyclodextrins.

Cyclodextrins are α-1,4-glycosidic cyclic oligosaccharides among which those of 6, 7 or 8 glucose monomers, the α-, β- and γ-cyclodextrins (or cyclohexa-, -hepta- or -octaamyloses), have the greatest economic importance. With hydrophobic guest molecules, such as perfumes, flavors or pharmaceutical active principles for example, they are capable of forming inclusion compounds from which the guest molecules can be released as required. Depending on the field of application of the ingredients, such inclusion compounds are of importance, for example, for the production of foods, pharmaceutical or cosmetic products, for example in corresponding products for the end consumer. Accordingly, the release of ingredients from cyclodextrins is a practical application for proteins according to the invention.

Another embodiment is the use of a protein or derivative according to the invention for the release of low molecular weight compounds from polysaccharide carriers or cyclodextrins.

By virtue of their enzymatic activity, amylolytic proteins according to the invention are also capable of releasing low molecular weight compounds from other α-1,4-glycosidic polysaccharides. As with the cyclodextrins, this can take place at the molecular level and even on larger systems such as, for example, ingredients encapsulated in the form of microcapsules. Starch, for example, is an established material for encapsulating such compounds as, for example, enzymes—which are to be introduced into reaction mixtures in defined quantities—during storage. The controlled release process from such capsules can be supported by amylolytic enzymes according to the invention.

Another embodiment is the use of a protein or derivative according to the invention for the production of foods and/or food ingredients.

The use of a protein or derivative for the production of animal feed and/or animal feed ingredients is another embodiment of the present invention.

Wherever starch or starch-derived carbohydrates play a role as ingredients of foods or animal feeds, an amylolytic activity may be used for the production of these articles. It increases the proportion of mono- or oligomers in relation to the polymeric sugar which can be to the benefit of the taste, digestibility or consistency of the food. This may be necessary for the production of certain animal feeds and also, for example, in the production of fruit juices, wine or other foods if the level of polymeric sugars is to be reduced and the level of sweet and/or more readily soluble sugars increased. The above-mentioned application for liquefying starch and/or producing ethanol may be regarded as an industrial variant of this principle.

In addition, amylases also counteract the loss of taste from bread and confectionery through staleness (anti-staling effect). To this end, they are suitably added to the dough before baking. Accordingly, preferred embodiments of the present invention are those in which proteins according to the invention are used for the production of bread and confectionery.

Another embodiment is the use of a protein or derivative according to the invention for dissolving starch-containing adhesive bonds.

Temporary bonding processes which are characterized in that they use a protein or derivative according to the invention represent another embodiment of the present invention Besides other natural materials, starch has been used for centuries as a binder in paper manufacture and in the bonding of different papers and paperboards. This applies, for example, to graphics and books. Over long periods, such papers can become wavy or can break under unfavorable influences, such as moisture for example, resulting in their complete destruction. To restore such papers and boards, it may be necessary to dissolve the adhesive layers which is made very much easier by the use of an amylolytic protein according to the invention. Vegetable polymers, such as starch or cellulose and water-soluble derivatives thereof, are used as adhesives or pastes. To this end, they first have to be swollen in water and then dried after application to the surface to be glued so that it is fixed to the substrate. The enzyme according to the invention may be added to such an aqueous suspension in order to influence the adhesive properties of the paste formed. However, instead of or in addition to this function, it may also be added to the paste in order to stay inactive on the surface for a long time after drying, for example for a few years. Controlled changes in the ambient conditions, for example through moistening, can be used to activate the enzyme at a later date and hence to induce dissolving of the paste. In this way, the glued surface is easier to separate from the substrate. In this process, the enzyme according to the invention, through its amylolytic activity, acts as a separating agent in a temporary bonding process or as a so-called "switch" for separating the glued article.

EXAMPLES

Example 1

The candidates for a microbiological screening for amylase-forming microorganisms with the selection criterion growth and halo formation on agar plates with starch as sole carbon source included the Bacillus strain Bacillus sp. (RNA group VI, alcaliphilic) A 7-7 which has been lodged at the DSMZ (DSM ID 98-587, lodgement DSM 12368).

The culture medium used was YPSS medium containing 15 g/l soluble starch, 4 g/l yeast extract, 1 g/l $K_2HPO_4$ and 0.5 g/l $MgSO_4 \times 7\ H_2O$. After autoclaving, the pH was adjusted to 10.3 with 20% sodium carbonate solution. Quantities of 25 ml medium were introduced into sterile 100 ml Erlenmeyer flasks with chicane and inoculated with a culture of Bacillus sp. A 7-7 (DSM 12368) which had been grown on a YPSS agar plate. Cultivation was carried out with shaking over 48 h at 30° C./200 r.p.m.

Example 2

A singular enzyme was obtained from the culture medium through the following purification steps: precipitation of the culture supernatant with ethanol; taking up the protein pellet in 50 mM tris/HCl buffer, pH 8.5; dialysis against 50 mM tris/HCl buffer, pH 8.5; cation exchange chromatography on Fast-flow-S-Sepharose® (Pharmacia-Amersham Biotech, Freiburg) with 50 mM tris/HCl buffer, pH 8.5 as eluent; rebuffering of the amylase-containing break-through against 20 mM glycine/NaOH buffer, pH 10, in PD10® columns (Pharmacia-Amersham Biotech); anion exchange chromatography on Mono-Q® (Pharmacia-Amersham Biotech) using the same buffer as eluent with an increasing salt gradient of 0 to 1 M NaCl. The amylase eluted at ca. 0.25 M NaCl.

2.6 mg of a protein were obtained in this way from 250 ml of culture medium, as determined by the BCA method (bicinchonic acid; 2,2'-biquinolyl-4,4'-dicarboxylic acid). The protein was shown to be pure by SDS gel electrophoresis and coloring with silver.

In denaturing SDS polyacrylic gel electrophoresis in an 8-25% gel in the PHAST® system (Pharmacia-Amersham) and in comparisons with relevant size markers, the amylolytic enzyme from Bacillus sp. A 7-7 (DSM 12368) has a molecular weight of 58 kD.

According to isoelectric focussing from pH 3 to 9 in the PHAST® system (Pharmacia-Amersham), its isoelectric point lies at 6.0.

The amylolytic activity of the purified enzyme was determined by the so-called DNS method, i.e. using dinitrosalicylic acid. To this end, the oligosaccharides disaccharides and glucose units released by the enzyme in the hydrolysis of starch are detected by oxidation of the reducing ends with dinitrosalicylic acid (DNS). The intensity of color development is proportional to the number of cleavage products formed. This test is carried out as follows: after incubation of 50 μl enzyme solution with 100 μl 1% soluble starch in tris/maleate buffer, pH 6.5 (12.11 g tris+11.61 g maleic acid to 1 liter, pH adjusted with 0.2 N NaOH) for 15 mins. at 50° C., the reduced saccharides are oxidized for 20 mins. at 100° C. with 300 μl DNS solution (8.8 g dinitrosalicylic acid, 915 ml distilled water, 250 g K—Na tartrate, 334 ml 4.5% NaOH, 6.3 g sodium disulfite). After cooling in an ice bath, absorption is photometrically detected at 540 nm against a blank value. The assay is calibrated via a maltose concentration series. The activity is expressed in μmol reducing sugars (based on maltose) per min. and ml.

According to this test, the protein of the Examples clearly has amylolytic activity. In the following, the activity determined in this way serves as a parameter for the stability of the enzyme under various conditions.

The temperature stability of the enzyme was measured in 10-minute incubations at a pH of 10. At room temperature, 30° C., 40° C. and 50° C., the activity is at least 85%. At 40° C., the amylase has its maximum of 90% residual activity. At 60° C., the enzyme has 50% activity. At temperatures above 60° C., it undergoes a serious loss of activity, but still has 10% residual activity at 80-90° C.

The amylolytic enzyme from Bacillus sp. A 7-7 (DSM 12368) is largely stable at pH values of 5 to 12 when incubated for 10 mins. at 40° C. At pH values of 8 to 9, the amylase is up to 100% stable. At higher and lower pH values, its activity slowly decreases although the enzyme still has more than 65% residual activity at pH 5 and pH 12.

For further characterization, the adverse effect on enzymatic activity of possibly disturbing factors, such as protease or detergents, is investigated. After exposure to 10 HPE/ml of the protease Savinase® (Novo Nordisk A/S, Bagsvaerd, Denmark; the HPE units can be determined by the method reported in Tenside 7 (1970), pp. 125-132) and 0.1% SDS for 15 minutes at pH 10/50° C., the enzyme shows 74% residual activity. After exposure to 0.1% SDS under the same conditions (pH 10, 15 minutes, 50° C.), the enzyme has 98% residual activity. Still under these conditions, it has 10% residual activity in the presence of 3 mM EDTA and 65% residual activity in the presence of 1 mM EDTA.

Example 3

All molecular-biological process steps follow standard methods which are described, for example, in manuals such as the manual by Fritsch, Sambrook and Maniatis entitled "Molecular cloning: a laboratory manual", Cold Spring Harbour Laboratory Press, New York, 1989.

In order to determine internal amino acid sequences, the protein obtained in accordance with Example 1 and purified in accordance with Example 2 was first precipitated with ethanol and then separated by denaturing SDS polyacrylamide gel electrophoresis. After the corresponding bands had been cut out from the SDS polyacrylamide gel, digestion was carried out tryptically in situ, the resulting peptides were separated by HPLC and analyzed by Edman degradation and MALDI-TOF analysis. The following two fragments D1 (SEQ ID NO: 6) and D6 (SEQ ID NO: 8) were selected from the many tryptic fragments obtained in this way:

```
D1: GITAVWIPPAWK                (SEQ ID NO: 6)

5'-GTN TGG ATH CCN CCN GCN TGG-3'   (SEQ ID NO: 7)

D6: QGYPSVFYGDYYGIPTH           (SEQ ID NO: 8)

5'-GGD ATN CCN TAN TAR TCN CC-3'    (SEQ ID NO: 9)
```

The corresponding degenerated PCR primers were constructed from their amino acid sequences (shown on the left). Their nucleotide sequences are shown on the right (N stands for any base; H stands for A or C or T; R stands for A or G; D stands for A, G or T).

From normally prepared chromosomal DNA of *Bacillus* sp. A 7-7 (DSM 12368) as matrix, a ca. 1,000 bp large fragment was amplified with this primer pair in a standard PCR. For storage, this PCR fragment was cloned in the vector pGEM-Teasy® (Promega, Madison, Wis., USA).

Example 4

Using the nonradioactive DIG-High-Prime® labeling kit of Boehringer Mannheim (Germany: product No. 1245832), the purified PCR fragment was labeled as directed as a DNA probe. For subsequent hybridization, chromosomal DNA of the strain *Bacillus* sp. A 7-7 (DSM 12368) was split with the restriction enzyme Xba 1 and separated via a 0.9% agarose gel. The DNA was transferred by a vacuum blotter to a positively charged nylon membrane (Roche, Mannheim). DNA hybridization and immunological detection of the PCR fragment used as probe were carried out according to the directions of the DIG-High-Prime® Labeling-and-Detection Starter Kits I® of Boehringer Mannheim. It was found that the target gene is present in an apparently ca. 3,000-4,000 large DNA section. The fragments of this size were purified via a 0.9% agarose gel and then ligated in the vector pCB56C (from *B. Subtilis* DB 104; described in application WO 91/02792) cut with the restriction enzymes Xba I and Nhe I. After transformation in an amylase-negative *Bacillus subtilis* strain, amylase-positive clones were identified through halo formation on starch-containing agar plates. A representative isolate carried the required insert.

Example 5

The sequencing of the plasmid obtained was carried out by standard chain termination methods. The plasmid contained an insert with a size of 2,015 bp. On top lies the 1,545 bp large gene for the interesting enzyme which is shown under SEQ ID NO. 1 in the sequence protocol of the present application. To this corresponds a polypeptide of 516 amino acids of which the sequence is shown in SEQ ID NO. 2 in the sequence protocol. The molecular weight derived from this amino acid sequence is 59 kD or—for the mature protein obtained by splitting off the signal peptide with 31 amino acids—55.5 kD.

Sequence comparisons by the BLAST method (S. F. Altschul et al., Nucl. Acids Res., 25 (1997), pp. 3389-3402) carried out on Mar. 17, 2000 characterize the enzyme as α-amylase. At the protein level, the homology of this protein to known proteins is between 71 and 95% identity, as shown in Table 2 below.

TABLE 2

Homology of the enzyme according to the invention from *Bacillus* sp. A 7-7 (DSM 12368) to the most similar and other representative proteins; expressed in % identity at protein level.

| Organism | ID | Identity [%] |
|---|---|---|
| B. alcalophilus | P 19571 | 95 |
| B. alcalophilus | WO 96/23873 | 91 |
| B. licheniformis | P 06278 | 72 |
| B. amyloliquefaciens | P 00692 | 72 |
| B. stearothermophilus | P 06297 | 71 |

ID stands for the entries at the Swiss Prot Data Bank (Geneva, Switzerland).

An alignment with representative proteins is shown in FIG. 1. All the proteins are α-amylases so that, on the basis of the substantial accords, it must be assumed that the enzyme according to the invention is also an α-amylase. This is in line with the original isolation of the gene from a starch-degrading microorganism (Example 1) and the discovery of the amylolytic activity of a transformant with the insert-carrying plasmid (Example 4). The properties of the amylolytic protein obtainable from this production strain correspond with those of the wild type strain (Example 2). Such a production strain can be produced in accordance with Example 4.

Example 6

Cotton fabrics were treated under standardized conditions with the four different soils A (chocolate mousse), B (oat flakes with cocoa), C (oat flakes with cocoa and a little milk) and D (potato starch) and, using the material thus prepared, various detergent formulations were launderometer-tested for washing performance. For the tests, a liquor ratio of 1:12 was adjusted and the fabrics were washed for 30 mins. at 30° C. The dosage was 5.88 g of the particular detergent per liter wash liquor. The water hardness was 16° German hardness.

The control detergent for A, B and C was a basic detergent with the following composition (in % by weight): 4% linear alkyl benzenesulfonate (sodium salt), 4% $C_{12-18}$ fatty alcohol sulfate (sodium salt), 5.5% $C_{12-18}$ fatty alcohol×7 EO, 1% sodium soap, 11% sodium carbonate, 2.5% amorphous sodium disilicate, 20% sodium perborate tetrahydrate, 5.5% TAED, 26% zeolite A, 4.5% polycarboxylate, 0.5% phosphonate, 2.5% granular foam inhibitor, 5% sodium sulfate, 1% protease granules, rest: water, optical brightener, perfume, salts. For the various test series, various amylases were added to the control detergent so that the final concentration was 44 TAU of amylolytic activity per liter wash liquor.

The amylolytic activity in TAU was determined using a modified p-nitrophenyl maltoheptaoside of which the terminal glucose unit is blocked by a benzylidene group which is split by amylase to free p-nitrophenyl oligosaccharide which in turn is reacted with the auxiliary enzymes glucoamylase and alpha-glucosidase to form glucose and p-nitrophenol. The quantity of p-nitrophenol released is thus proportional to the amylase activity. The measurement is carried out, for example, with an Abott Quick-Start® Testkit (Abott Park, Ill., USA). The increase in absorption (405 nm) in the test mixture is detected over 3 mins. at 37° C. against a blank value using a photometer. An enzyme standard of known activity is used for calibration (for example Maxamyl®/Purastar® of Genencor with an activity of 2,900 TAU/g). Evaluation is carried out by plotting the absorption difference dE (40 5 nm) per min. against the enzyme concentration of the standard.

The amylolytic enzyme according to the invention from *Bacillus* sp. A 7-7 (DSM 12368) was compared with Termamyl®, Duramyl® and BAN® (manufacturer: Novo Nordisk A/S, Bagsvaerd, Denmark). The detergent used for soil D was the same basic formulation, but without protease, used as control for A-C or with added amylases.

In the present Example, the whiteness of the fabrics in the CIELAB system was measured before and after washing with a Minolta CR 310 in comparison with a standard which was standardized to 100%. The differences in the results obtained are set out in Table 3 below for the respective tests. The average values of 5 measurements are shown. They are a direct indication of the contribution of the enzyme present to the washing performance of the detergent used.

TABLE 3

| Basic detergent containing | A | B | C | D |
|---|---|---|---|---|
| Amylase essential to the invention | 29.3 | 26.0 | 20.9 | 15.2 |
| Termamyl ® | 25.9 | 22.7 | 17.4 | 12.3 |
| Duramyl ® | 28.6 | 23.4 | 20.2 | 14.2 |
| BAN ® | 22.5 | 22.0 | 17.0 | 13.2 |
| Control without amylase | 22.9 | 22.2 | 11.9 | 10.0 |
| Standard deviation | 1.3 | 0.6 | 1.4 | 2.2 |

It can be seen that the α-amylase from *Bacillus* sp. A 7-7 (DSM 12368) produces distinctly better washing performances against soil B than any of the three reference enzymes. Against the other soils, it shows slightly improved washing performance (within the limit of error) although this is still well above the comparison values without amylolytic enzyme. This result is all the more conclusive insofar as all the detergent formulations tested contain a bleaching agent to which wild type enzymes are generally very sensitive.

Example 7

Cotton fabrics were treated under standardized conditions with soils B (oat flakes with cocoa) and C (oat flakes with cocoa and a little milk). Launderometer testing was carried out as in Example 1 using another detergent formulation, namely (in % by weight): 14% Na alkyl benzenesulfonate, 6% Na fatty alcohol sulfate, 6% 7x-ethoxylated $C_{12-18}$ fatty alcohol, 1% soap, 25% zeolite NaA, 10% Na carbonate, 5% polymeric polycarboxylate (Sokalan® CP5), 11% trisodium citrate dihydrate, 4% citric acid, 1% particulate foam inhibitor, 1% protease granules, 5% sodium sulfate, rest: water and salts. For the various test series, various amylases were added to this basic formation so that the final concentration was 33.5 TAU of amylolytic activity per liter of wash liquor, as determined by the method described in Example 1. The amylolytic enzyme essential to the invention from *Bacillus* sp. A 7-7 (DSM 12368) was compared with Termamyl®, Duramyl® and BAN® (manufacturer: Novo Nordisk A/S, Bagsvaerd, Denmark). The dosage was 4.45 g of the particular detergent per liter wash liquor.

After washing, the whiteness of the washed fabrics was determined in the same way as in the preceding Example. The differences obtained are set out in Table 4 and represent the average values of 5 measurements which, again, are a direct indication of the contribution of the particular enzyme to the washing performance of the detergent.

TABLE 4

| Basic detergent containing | B | C |
|---|---|---|
| Amylase essential to the invention | 30.6 | 17.5 |
| Termamyl ® | 29.3 | 15.0 |
| Duramyl ® | 29.2 | 16.7 |
| BAN ® | 28.9 | 15.6 |
| Control without amylase | 28.5 | 14.5 |
| Standard deviation | 0.6 | 1.2 |

It can be seen that the α-amylase from *Bacillus* sp. A 7-7 (DSM 12368) in this bleach-free detergent formulation produces better washing performance against soils B and C than any of the reference enzymes.

Example 8

Cotton fabrics were soiled under standardized conditions with two different types of commercially available milk cocoa (E and F). Launderometer testing was then carried out as described in Example 1. The control detergent used was the basic detergent formulation of Example 2, but without protease. For the various test series, the various amylases were added in the same way as in Example 2. The detergent was used in the same dosage.

After washing, the whiteness of the washed fabrics was measured in comparison with that of barium sulfate which was standardized to 100%. The measurement was carried out using a Datacolor SF500-2 spectrometer at 460 nm (UV blocking filter), 30 mm orifice, without gloss, light type D65, 10°, d/8°. The results obtained are set out as % reflectance, i.e. as percentages in comparison with barium sulfate, in Table 4 below which also shows the particular starting value. The values shown are the averages of 5 measurements and are a direct indication of the contribution of the amylolytic enzyme present to the washing performance of the detergent used.

TABLE 5

| Basic detergent containing | E | F |
|---|---|---|
| Amylase essential to the invention | 70.3 | 41.0 |
| Termamyl ® | 67.3 | 39.7 |
| Duramyl ® | 68.3 | 40.5 |
| BAN ® | 68.7 | 39.8 |
| Control without amylase | 61.1 | 31.4 |
| Starting value | 21.1 | 25.0 |
| Standard deviation | 1.0 | 1.2 |

It can be seen that the α-amylase from *Bacillus* sp. A 7-7 (DSM 12368) in this formulation produces distinctly better washing performance in the case of E than any of the reference systems tested and, in the case of F, comparable washing performance.

Example 9

For application-oriented cleaning tests, vessels with hard smooth surfaces were provided with the following soils under standardized conditions: A (DIN oat flakes), B (oat flakes swollen in water) and C (mixed starch), and were washed at 45° C. with the normal program of a domestic dishwasher (Miele® G 575). The detergent dosage was 20 g per cleaning cycle and the water hardness was 16° German hardness.

The following basic formulation was used as the detergent (all quantities in % by weight): 55% sodium tripolyphosphate (expressed as water-free), 4% amorphous sodium disilicate (expressed as water-free), 22% sodium carbonate, 9% sodium perborate, 2% TAED, 2% nonionic surfactant, 1.4% protease granules, rest: water, dyes, perfume. For the various tests, various amylases, namely Termamyl®, Duramyl®, BAN® (manufacturer: Novo Nordisk A/S, Bagsvaerd, Denmark), or the amylolytic enzyme from *Bacillus* sp. A 7-7 (DSM 12368) were added to the basic formulation in effective quantities of 150 TAU of amylolytic activity per cleaning cycle, as determined by the method described in Example 1.

After washing, the removal of soil A was evaluated after coloring with iodine by the iodine/starch reaction, evaluation being carried out visually on a scale of 0 (=unchanged, i.e. very pronounced soil) to 10 (=no soil discernible). The removal of soils B and C was determined gravimetrically in %. To this end, the difference between the weight of the soiled and then cleaned vessel and the starting weight of the vessel was related to the difference in weight between the uncleaned vessel and its starting weight. This relation may be regarded as percentage removal.

The results obtained are set out in Table 6 below where they are shown as the averages of 9 measurements for A and B and 18 measurements for C. They are a direct indication of the contribution of the enzyme present to the cleaning performance of the detergent used.

TABLE 6

| Basic detergent containing | A | B % removal | C % removal |
|---|---|---|---|
| Amylase essential to the invention | 6.2 | 91.2 | 95.8 |
| Termamyl ® | 3.7 | 53.9 | 15.7 |
| Duramyl ® | 2.2 | 78.8 | 35.5 |
| BAN ® | 3.7 | 69.1 | 34.2 |
| Control without amylase | 4.3 | 31.7 | 0.6 |

These results show that the α-amylase from *Bacillus* sp. A 7-7 (DSM 12368) is superior to all the other amylases tested in its cleaning performance against all three soils in dishwasher detergents at 45° C.

Example 10

Vessels with hard smooth surfaces were provided with the same soils as in the preceding Example and washed at 55° C. The cleaning conditions and the formulation of the detergents used also corresponded to those of the preceding Example.

After washing, the removal of soil A was visually evaluated as in Example 4 on a scale of 0 to 10 using the iodine/starch reaction. The removal of soils B and C was determined gravimetrically in %, again as in Example 4. The results obtained are set out in Table 6 below where they are shown as the averages of 9 measurements for A, 10 measurements for B and 18 measurements for C. They are a direct indication of the contribution of the enzyme present to the cleaning performance of the detergent used.

TABLE 6

| Basic detergent containing | A | B % removal | C % removal |
|---|---|---|---|
| Amylase essential to the invention | 8.3 | 97 | 99 |
| Termamyl ® | 6.7 | 95 | 53 |
| Duramyl ® | 6.9 | 95 | 89 |
| BAN ® | 6.2 | 92 | 77 |
| Control without amylase | 5.3 | 71 | 27 |

These results show that the α-amylase from *Bacillus* sp. A 7-7 (DSM 12368) is superior to all the other amylases tested in its cleaning performance against all three soils in dishwasher detergents, even at a dishwashing temperature of 55° C.

DESCRIPTION OF THE FIGURES

FIG. 1:

Alignment of the amylolytic enzyme according to the invention from *Bacillus* sp. A 7-7 (DSM 12368) with the three most similar amylases.

In FIG. 1,
1=amylase from *Bacillus* sp. A7-7 (DSM 12368) (SEQ ID NO: 2)
2=mature amylase from *Bacillus* sp. # 707 according to: Tsukamoto, Kimura, Ishii, Takano and Yamane, *Biochem. Biophys. Res. Common.* 151 (1988), pp. 25-31 (SEQ ID NO: 3)
3=amylase of SEQ ID NO. 1 from WO 96/23873 (SEQ ID NO: 4)
4=amylase of SEQ ID NO. 2 from WO 96/23873 (SEQ ID NO: 5)

The invention claimed is:

1. Bacteria characterized as a member of the genus *Bacillus* sp. A 7-7 (DSM 12368) and from which is isolated a polypeptide having amylolytic activity and comprising an amino acid sequence that is selected from the group consisting of a sequence that is at least 96% identical to SEQ ID NO:2 and a sequence that is at least 96% identical to residues 32 to 516 of SEQ ID NO:2.

* * * * *

SEQUENCE LISTING

<160> NUMBER OF SEQ ID NOS: 9

<210> SEQ ID NO 1
<211> LENGTH: 1551
<212> TYPE: DNA
<213> ORGANISM: Bacillus sp. A 7-7 (DSM 12368)
<220> FEATURE:
<221> NAME/KEY: CDS
<222> LOCATION: (1)..(1551)

<400> SEQUENCE: 1

```
atg aga aaa cgt aaa aat gga tta atc agt att cta ttg gca ttt ttg        48
Met Arg Lys Arg Lys Asn Gly Leu Ile Ser Ile Leu Leu Ala Phe Leu
    -30             -25                 -20 ttg gta ctt aca tca ata cct ttt act tca gca aac gta gaa gca cac        96
Leu Val Leu Thr Ser Ile Pro Phe Thr Ser Ala Asn Val Glu Ala His
-15                 -10                  -5              -1   1
```

-continued

```
cat aat ggc aca aat gga aca atg atg caa tat ttt gaa tgg tat ttg    144
His Asn Gly Thr Asn Gly Thr Met Met Gln Tyr Phe Glu Trp Tyr Leu
         5                  10                  15 cca aat gac ggt aat cat tgg aat aga tta aga tca gat gca agt aat    192
Pro Asn Asp Gly Asn His Trp Asn Arg Leu Arg Ser Asp Ala Ser Asn
        20                  25                  30 ctt aaa gat aaa ggg att aca gcg gtt tgg ata cca cct gct tgg aaa    240
Leu Lys Asp Lys Gly Ile Thr Ala Val Trp Ile Pro Pro Ala Trp Lys
    35                  40                  45 ggg gct tct caa aat gat gta ggg tat gga gcc tat gat ctg tat gat    288
Gly Ala Ser Gln Asn Asp Val Gly Tyr Gly Ala Tyr Asp Leu Tyr Asp
 50                  55                  60                  65 tta gga gaa ttc aat caa aaa gga acc gta cgt aca aag tac gga acc    336
Leu Gly Glu Phe Asn Gln Lys Gly Thr Val Arg Thr Lys Tyr Gly Thr
                 70                  75                  80 cgt aat caa tta caa gct gca gta acc gcc tta aaa agt aat ggt att    384
Arg Asn Gln Leu Gln Ala Ala Val Thr Ala Leu Lys Ser Asn Gly Ile
             85                  90                  95 caa gta tac gga gat gtc gta atg aat cat aag ggt gga gcg gat gcc    432
Gln Val Tyr Gly Asp Val Val Met Asn His Lys Gly Gly Ala Asp Ala
        100                 105                 110 act gag tgg gtt cga gcg gtt gaa gtg aac cca agt aat cgt aat caa    480
Thr Glu Trp Val Arg Ala Val Glu Val Asn Pro Ser Asn Arg Asn Gln
    115                 120                 125 gaa gtc tct ggt gat tat acg att gag gct tgg act aag ttt gat ttt    528
Glu Val Ser Gly Asp Tyr Thr Ile Glu Ala Trp Thr Lys Phe Asp Phe
130                 135                 140                 145 cct ggt cga ggt aat acc cac tct aac ttt aaa tgg aga tgg tat cat    576
Pro Gly Arg Gly Asn Thr His Ser Asn Phe Lys Trp Arg Trp Tyr His
                150                 155                 160 ttc gat ggt gta gat tgg gat cag tca cgt caa ttg cag aat cga atc    624
Phe Asp Gly Val Asp Trp Asp Gln Ser Arg Gln Leu Gln Asn Arg Ile
            165                 170                 175 tat aaa ttc aga gga gat gga aaa ggt tgg gac tgg gaa gtt gat aca    672
Tyr Lys Phe Arg Gly Asp Gly Lys Gly Trp Asp Trp Glu Val Asp Thr
        180                 185                 190 gag aac gga aac tat gac tat cta atg tac gcg gat att gat atg gat    720
Glu Asn Gly Asn Tyr Asp Tyr Leu Met Tyr Ala Asp Ile Asp Met Asp
    195                 200                 205 cac cct gaa gta gtg aat gaa ctc aga aac tgg ggt gta tgg tat acc    768
His Pro Glu Val Val Asn Glu Leu Arg Asn Trp Gly Val Trp Tyr Thr
210                 215                 220                 225 aat aca ctg ggg cta gac ggg ttc aga ata ggt gcg gta aaa cat ata    816
Asn Thr Leu Gly Leu Asp Gly Phe Arg Ile Gly Ala Val Lys His Ile
                230                 235                 240 aaa tat agc ttt act cgt gat tgg ctt act cac gtt aga aat acg aca    864
Lys Tyr Ser Phe Thr Arg Asp Trp Leu Thr His Val Arg Asn Thr Thr
            245                 250                 255 ggt aaa aat atg ttt gca gtt gca gag ttc tgg aag aat gac ata ggt    912
Gly Lys Asn Met Phe Ala Val Ala Glu Phe Trp Lys Asn Asp Ile Gly
        260                 265                 270 gca att gaa aat tac tta agt aaa aca aat tgg aat cat tca gtt ttt    960
Ala Ile Glu Asn Tyr Leu Ser Lys Thr Asn Trp Asn His Ser Val Phe
    275                 280                 285 gat gtg ccc ctg cat tat aac ctt tat aat gca tcg aga agt ggt ggc   1008
Asp Val Pro Leu His Tyr Asn Leu Tyr Asn Ala Ser Arg Ser Gly Gly
290                 295                 300                 305 aat tat gat atg agg caa ata ttt aat gga aca gtt gtt cag aga cat   1056
Asn Tyr Asp Met Arg Gln Ile Phe Asn Gly Thr Val Val Gln Arg His
```

```
                    310                 315                 320
cct aca cat gct gta aca ttt gtt gat aac cat gat tca cag ccg gaa      1104
Pro Thr His Ala Val Thr Phe Val Asp Asn His Asp Ser Gln Pro Glu
            325                 330                 335 gaa gcc cta gag tca ttt gtt gaa gag tgg ttc aaa ccg tta gcg tgt      1152
Glu Ala Leu Glu Ser Phe Val Glu Glu Trp Phe Lys Pro Leu Ala Cys
            340                 345                 350 gct ctc aca cta aca cgt gat caa gga tat cct tcc gtt ttt tat gga      1200
Ala Leu Thr Leu Thr Arg Asp Gln Gly Tyr Pro Ser Val Phe Tyr Gly
        355                 360                 365 gat tat tat ggg att ccg acg cat ggt gta cca gca atg aaa tct aag      1248
Asp Tyr Tyr Gly Ile Pro Thr His Gly Val Pro Ala Met Lys Ser Lys
370                 375                 380                 385 att gat ccg att tta gaa gca cgt caa aag tat gcg tac gga aaa caa      1296
Ile Asp Pro Ile Leu Glu Ala Arg Gln Lys Tyr Ala Tyr Gly Lys Gln
                390                 395                 400 aat gat tat ttg gat cac cat aat atg att ggc tgg acg cgt gaa ggt      1344
Asn Asp Tyr Leu Asp His His Asn Met Ile Gly Trp Thr Arg Glu Gly
            405                 410                 415 aat aca gca cat ccc aac tca gga cta gca act att atg tcg gat ggc      1392
Asn Thr Ala His Pro Asn Ser Gly Leu Ala Thr Ile Met Ser Asp Gly
            420                 425                 430 cca gga gga aat aaa tgg atg tat gtt ggg cgt aat aag gct gga caa      1440
Pro Gly Gly Asn Lys Trp Met Tyr Val Gly Arg Asn Lys Ala Gly Gln
        435                 440                 445 gtt tgg aga gat att aca gga aat cgc tca ggt acg gtg acg att aac      1488
Val Trp Arg Asp Ile Thr Gly Asn Arg Ser Gly Thr Val Thr Ile Asn
450                 455                 460                 465 gca gat ggg tgg ggt aat ttt tct gta aat ggt ggg tct gta tct ata      1536
Ala Asp Gly Trp Gly Asn Phe Ser Val Asn Gly Gly Ser Val Ser Ile
                470                 475                 480 tgg gta aat aat taa                                                  1551
Trp Val Asn Asn
            485

<210> SEQ ID NO 2
<211> LENGTH: 516
<212> TYPE: PRT
<213> ORGANISM: Bacillus sp. A 7-7 (DSM 12368)

<400> SEQUENCE: 2

Met Arg Lys Arg Lys Asn Gly Leu Ile Ser Ile Leu Leu Ala Phe Leu
  1               5                  10                  15

Leu Val Leu Thr Ser Ile Pro Phe Thr Ser Ala Asn Val Glu Ala His
             20                  25                  30

His Asn Gly Thr Asn Gly Thr Met Met Gln Tyr Phe Glu Trp Tyr Leu
         35                  40                  45

Pro Asn Asp Gly Asn His Trp Asn Arg Leu Arg Ser Asp Ala Ser Asn
     50                  55                  60

Leu Lys Asp Lys Gly Ile Thr Ala Val Trp Ile Pro Pro Ala Trp Lys
 65                  70                  75                  80

Gly Ala Ser Gln Asn Asp Val Gly Tyr Gly Ala Tyr Asp Leu Tyr Asp
                 85                  90                  95

Leu Gly Glu Phe Asn Gln Lys Gly Thr Val Arg Thr Lys Tyr Gly Thr
            100                 105                 110

Arg Asn Gln Leu Gln Ala Ala Val Thr Ala Leu Lys Ser Asn Gly Ile
        115                 120                 125

Gln Val Tyr Gly Asp Val Val Met Asn His Lys Gly Gly Ala Asp Ala
```

```
            130                 135                 140
Thr Glu Trp Val Arg Ala Val Glu Val Asn Pro Ser Asn Arg Asn Gln
145                 150                 155                 160

Glu Val Ser Gly Asp Tyr Thr Ile Glu Ala Trp Thr Lys Phe Asp Phe
                165                 170                 175

Pro Gly Arg Gly Asn Thr His Ser Asn Phe Lys Trp Arg Trp Tyr His
                180                 185                 190

Phe Asp Gly Val Asp Trp Asp Ser Arg Gln Leu Gln Asn Arg Ile
                195                 200                 205

Tyr Lys Phe Arg Gly Asp Gly Lys Gly Trp Asp Trp Glu Val Asp Thr
210                 215                 220

Glu Asn Gly Asn Tyr Asp Tyr Leu Met Tyr Ala Asp Ile Asp Met Asp
225                 230                 235                 240

His Pro Glu Val Val Asn Glu Leu Arg Asn Trp Gly Val Trp Tyr Thr
                245                 250                 255

Asn Thr Leu Gly Leu Asp Gly Phe Arg Ile Gly Ala Val Lys His Ile
                260                 265                 270

Lys Tyr Ser Phe Thr Arg Asp Trp Leu Thr His Val Arg Asn Thr Thr
                275                 280                 285

Gly Lys Asn Met Phe Ala Val Ala Glu Phe Trp Lys Asn Asp Ile Gly
290                 295                 300

Ala Ile Glu Asn Tyr Leu Ser Lys Thr Asn Trp Asn His Ser Val Phe
305                 310                 315                 320

Asp Val Pro Leu His Tyr Asn Leu Tyr Asn Ala Ser Arg Ser Gly Gly
                325                 330                 335

Asn Tyr Asp Met Arg Gln Ile Phe Asn Gly Thr Val Val Gln Arg His
                340                 345                 350

Pro Thr His Ala Val Thr Phe Val Asp Asn His Asp Ser Gln Pro Glu
                355                 360                 365

Glu Ala Leu Glu Ser Phe Val Glu Glu Trp Phe Lys Pro Leu Ala Cys
                370                 375                 380

Ala Leu Thr Leu Thr Arg Asp Gln Gly Tyr Pro Ser Val Phe Tyr Gly
385                 390                 395                 400

Asp Tyr Tyr Gly Ile Pro Thr His Gly Val Pro Ala Met Lys Ser Lys
                405                 410                 415

Ile Asp Pro Ile Leu Glu Ala Arg Gln Lys Tyr Ala Tyr Gly Lys Gln
                420                 425                 430

Asn Asp Tyr Leu Asp His His Asn Met Ile Gly Trp Thr Arg Glu Gly
                435                 440                 445

Asn Thr Ala His Pro Asn Ser Gly Leu Ala Thr Ile Met Ser Asp Gly
450                 455                 460

Pro Gly Gly Asn Lys Trp Met Tyr Val Gly Arg Asn Lys Ala Gly Gln
465                 470                 475                 480

Val Trp Arg Asp Ile Thr Gly Asn Arg Ser Gly Thr Val Thr Ile Asn
                485                 490                 495

Ala Asp Gly Trp Gly Asn Phe Ser Val Asn Gly Gly Ser Val Ser Ile
                500                 505                 510

Trp Val Asn Asn
        515

<210> SEQ ID NO 3
<211> LENGTH: 518
<212> TYPE: PRT
<213> ORGANISM: Bacillus sp. # 707
```

<400> SEQUENCE: 3

```
Met Lys Met Arg Thr Gly Lys Lys Gly Phe Leu Ser Ile Leu Leu Ala
1               5                   10                  15
Phe Leu Leu Val Ile Thr Ser Ile Pro Phe Thr Leu Val Asp Val Glu
                20                  25                  30
Ala His His Asn Gly Thr Asn Gly Thr Met Met Gln Tyr Phe Glu Trp
            35                  40                  45
Tyr Leu Pro Asn Asp Gly Asn His Trp Asn Arg Leu Asn Ser Asp Ala
    50                  55                  60
Ser Asn Leu Lys Ser Lys Gly Ile Thr Ala Val Trp Ile Pro Pro Ala
65                  70                  75                  80
Trp Lys Gly Ala Ser Gln Asn Asp Val Gly Tyr Gly Ala Tyr Asp Leu
                85                  90                  95
Tyr Asp Leu Gly Glu Phe Asn Gln Lys Gly Thr Val Arg Thr Lys Tyr
                100                 105                 110
Gly Thr Arg Ser Gln Leu Gln Ala Ala Val Thr Ser Leu Lys Asn Asn
            115                 120                 125
Gly Ile Gln Val Tyr Gly Asp Val Val Met Asn His Lys Gly Gly Ala
    130                 135                 140
Asp Ala Thr Glu Met Val Arg Ala Val Glu Val Asn Pro Asn Asn Arg
145                 150                 155                 160
Asn Gln Glu Val Thr Gly Glu Tyr Thr Ile Glu Ala Trp Thr Arg Phe
                165                 170                 175
Asp Phe Pro Gly Arg Gly Asn Thr His Ser Ser Phe Lys Trp Arg Trp
                180                 185                 190
Tyr His Phe Asp Gly Val Asp Trp Asp Gln Ser Arg Arg Leu Asn Asn
            195                 200                 205
Arg Ile Tyr Lys Phe Arg Gly His Gly Lys Ala Trp Asp Trp Glu Val
    210                 215                 220
Asp Thr Glu Asn Gly Asn Tyr Asp Tyr Leu Met Tyr Ala Asp Ile Asp
225                 230                 235                 240
Met Asp His Pro Glu Val Val Asn Glu Leu Arg Asn Trp Gly Val Trp
                245                 250                 255
Tyr Thr Asn Thr Leu Gly Leu Asp Gly Phe Arg Ile Asp Ala Val Lys
                260                 265                 270
His Ile Lys Tyr Ser Phe Thr Arg Asp Trp Ile Asn His Val Arg Ser
            275                 280                 285
Ala Thr Gly Lys Asn Met Phe Ala Val Ala Glu Phe Trp Lys Asn Asp
    290                 295                 300
Leu Gly Ala Ile Glu Asn Tyr Leu Gln Lys Thr Asn Trp Asn His Ser
305                 310                 315                 320
Val Phe Asp Val Pro Leu His Tyr Asn Leu Tyr Asn Ala Ser Lys Ser
                325                 330                 335
Gly Gly Asn Tyr Asp Met Arg Asn Ile Phe Asn Gly Thr Val Val Gln
                340                 345                 350
Arg His Pro Ser His Ala Val Thr Phe Val Asp Asn His Asp Ser Gln
            355                 360                 365
Pro Glu Glu Ala Leu Glu Ser Phe Val Glu Trp Phe Lys Pro Leu
    370                 375                 380
Ala Tyr Ala Leu Thr Leu Thr Arg Glu Gln Gly Tyr Pro Ser Val Phe
385                 390                 395                 400
Tyr Gly Asp Tyr Tyr Gly Ile Pro Thr His Gly Val Pro Ala Met Arg
```

```
                405                 410                 415
Ser Lys Ile Asp Pro Ile Leu Glu Ala Arg Gln Lys Tyr Ala Tyr Gly
            420                 425                 430

Lys Gln Asn Asp Tyr Leu Asp His His Asn Ile Ile Gly Trp Thr Arg
            435                 440                 445

Glu Gly Asn Thr Ala His Pro Asn Ser Gly Leu Ala Thr Ile Met Ser
            450                 455                 460

Asp Gly Ala Gly Gly Ser Lys Trp Met Phe Val Gly Arg Asn Lys Ala
465                 470                 475                 480

Gly Gln Val Trp Ser Asp Ile Thr Gly Asn Arg Thr Gly Thr Val Thr
            485                 490                 495

Ile Asn Ala Asp Gly Trp Gly Asn Phe Ser Val Asn Gly Gly Ser Val
            500                 505                 510

Ser Ile Trp Val Asn Lys
            515

<210> SEQ ID NO 4
<211> LENGTH: 485
<212> TYPE: PRT
<213> ORGANISM: Bacillus sp. NCIB 12512

<400> SEQUENCE: 4

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Asp Asp Ala Ala
            20                  25                  30

Asn Leu Lys Ser Lys Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65              70                  75                  80

Thr Arg Asn Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Gly Thr Glu Ile Val Asn Ala Val Glu Val Asn Arg Ser Asn Arg Asn
            115                 120                 125

Gln Glu Thr Ser Gly Glu Tyr Ala Ile Glu Ala Trp Thr Lys Phe Asp
        130                 135                 140

Phe Pro Gly Arg Gly Asn Asn His Ser Ser Phe Lys Trp Arg Trp Tyr
145                 150                 155                 160

His Phe Asp Gly Thr Asp Trp Asp Gln Ser Arg Gln Leu Gln Asn Lys
                165                 170                 175

Ile Tyr Lys Phe Arg Gly Thr Gly Lys Ala Trp Asp Trp Glu Val Asp
            180                 185                 190

Thr Glu Asn Gly Asn Tyr Asp Tyr Leu Met Tyr Ala Asp Val Asp Met
            195                 200                 205

Asp His Pro Glu Val Ile His Glu Leu Arg Asn Trp Gly Val Trp Tyr
        210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255
```

```
Thr Gly Lys Pro Met Phe Ala Val Ala Glu Phe Trp Lys Asn Asp Leu
            260                 265                 270

Gly Ala Ile Glu Asn Tyr Leu Asn Lys Thr Ser Trp Asn His Ser Ala
        275                 280                 285

Phe Asp Val Pro Leu His Tyr Asn Leu Tyr Asn Ala Ser Asn Ser Gly
    290                 295                 300

Gly Tyr Tyr Asp Met Arg Asn Ile Leu Asn Gly Ser Val Val Gln Lys
305                 310                 315                 320

His Pro Thr His Ala Val Thr Phe Val Asp Asn His Asp Ser Gln Pro
                325                 330                 335

Gly Glu Ala Leu Glu Ser Phe Val Gln Gln Trp Phe Lys Pro Leu Ala
            340                 345                 350

Tyr Ala Leu Val Leu Thr Arg Ile Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Leu Leu Gln Ala Arg Gln Thr Phe Ala Tyr Gly Thr
385                 390                 395                 400

Gln His Asp Tyr Phe Asp His His Asp Ile Ile Gly Trp Thr Arg Glu
                405                 410                 415

Gly Asn Ser Ser His Pro Asn Ser Gly Leu Ala Thr Ile Met Ser Asp
            420                 425                 430

Gly Pro Gly Gly Asn Lys Trp Met Tyr Val Gly Lys Asn Lys Ala Gly
        435                 440                 445

Gln Val Trp Arg Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Val Trp Val Lys Gln
                485

<210> SEQ ID NO 5
<211> LENGTH: 485
<212> TYPE: PRT
<213> ORGANISM: Bacillus sp. NCIB 12513

<400> SEQUENCE: 5

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Glu Ser Ala Ile His Ala Leu Lys Asn Asn Gly
                85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Ser Asn Arg Asn
        115                 120                 125

Gln Glu Ile Ser Gly Asp Tyr Thr Ile Glu Ala Trp Thr Lys Phe Asp
    130                 135                 140
```

```
Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
450                 455                 460

Asn Ala Asp Gly Trp Ala Asn Phe Ser Val Asn Gly Gly Ser Val Ser
465                 470                 475                 480

Ile Trp Val Lys Arg
                485

<210> SEQ ID NO 6
<211> LENGTH: 12
<212> TYPE: PRT
<213> ORGANISM: Unknown
<220> FEATURE:
<223> OTHER INFORMATION: peptide fragment (D1)

<400> SEQUENCE: 6

Gly Ile Thr Ala Val Trp Ile Pro Pro Ala Trp Lys
1               5                   10
```

<210> SEQ ID NO 7
<211> LENGTH: 21
<212> TYPE: DNA
<213> ORGANISM: Unknown
<220> FEATURE:
<223> OTHER INFORMATION: Degenerated PCR primer corresponding to peptide
      fragment D1
<220> FEATURE:
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: h is a or c or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (18)..(18)
<223> OTHER INFORMATION: n is a, c, g, or t

<400> SEQUENCE: 7
gtntggathc cnccngcntg g                                              21

<210> SEQ ID NO 8
<211> LENGTH: 17
<212> TYPE: PRT
<213> ORGANISM: Unknown
<220> FEATURE:
<223> OTHER INFORMATION: Peptide fragment D6

<400> SEQUENCE: 8

Gln Gly Tyr Pro Ser Val Phe Tyr Gly Asp Tyr Tyr Gly Ile Pro Thr
1               5                   10                  15

His

<210> SEQ ID NO 9
<211> LENGTH: 20
<212> TYPE: DNA
<213> ORGANISM: Unknown
<220> FEATURE:
<223> OTHER INFORMATION: Degenerated PCR primer corresponding to peptide
      fragment D6
<220> FEATURE:
<221> NAME/KEY: misc_feature
<222> LOCATION: (3)..(3)
<223> OTHER INFORMATION: d is a, g or t
<220> FEATURE:
<221> NAME/KEY: misc_feature
<222> LOCATION: (6)..(6)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t
<220> FEATURE:
<221> NAME/KEY: misc_feature
<222> LOCATION: (15)..(15)
<223> OTHER INFORMATION: r is a or g
<220> FEATURE:
<221> NAME/KEY: misc_feature

```
<222> LOCATION: (18)..(18)
<223> OTHER INFORMATION: n is a, c, g, or t

<400> SEQUENCE: 9
ggdatnccnt antartcncc                                              20
```